(12) United States Patent
Zhou et al.

(10) Patent No.: US 9,802,929 B2
(45) Date of Patent: *Oct. 31, 2017

(54) BENZO FIVE-MEMBERED NITROGEN HETEROCYCLIC PIPERIDINE OR PIPERAZINE DERIVATIVES AND PREPARATION METHODS AND PHARMACEUTICAL COMPOSITIONS THEREOF

(71) Applicant: Shenyang Haiwang Biotechnology Co., Ltd., Liaoning Prov. (CN)

(72) Inventors: Yan Zhou, Liaoning (CN); Lirong Zhang, Liaoning (CN); Jie Zhou, Liaoning (CN); Xin Zhou, Liaoning (CN)

(73) Assignee: SHENYANG HAIWANG BIOTECHNOLOGY CO., LTD., Shenyang, Liaoning Prov. (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/647,378

(22) PCT Filed: Nov. 25, 2013

(86) PCT No.: PCT/CN2013/001141
§ 371 (c)(1),
(2) Date: May 26, 2015

(87) PCT Pub. No.: WO2014/079154
PCT Pub. Date: May 30, 2014

(65) Prior Publication Data
US 2016/0009703 A1    Jan. 14, 2016

(30) Foreign Application Priority Data

| Nov. 26, 2012 | (CN) | .......................... 2012 1 0486619 |
| Nov. 26, 2012 | (CN) | .......................... 2012 1 0486659 |
| Nov. 26, 2012 | (CN) | .......................... 2012 1 0487756 |
| Sep. 10, 2013 | (CN) | .......................... 2013 1 0409084 |
| Sep. 10, 2013 | (CN) | .......................... 2013 1 0409567 |

(51) Int. Cl.

| C07D 249/18 | (2006.01) |
| C07D 417/12 | (2006.01) |
| A61K 31/496 | (2006.01) |
| C07D 401/06 | (2006.01) |
| C07D 403/12 | (2006.01) |
| C07D 405/12 | (2006.01) |
| C07D 413/14 | (2006.01) |
| C07D 417/14 | (2006.01) |
| C07D 401/14 | (2006.01) |
| C07D 405/14 | (2006.01) |
| A61K 31/454 | (2006.01) |
| C07D 235/08 | (2006.01) |

(Continued)

(52) U.S. Cl.
CPC .......... *C07D 417/14* (2013.01); *A61K 31/454* (2013.01); *A61K 31/496* (2013.01); *A61K 45/06* (2013.01); *C07D 235/04* (2013.01); *C07D 235/08* (2013.01); *C07D 235/14* (2013.01); *C07D 235/22* (2013.01); *C07D 235/24* (2013.01); *C07D 249/18* (2013.01); *C07D 401/06* (2013.01); *C07D 401/12* (2013.01); *C07D 401/14* (2013.01); *C07D 403/12* (2013.01); *C07D 405/12* (2013.01); *C07D 405/14* (2013.01); *C07D 413/12* (2013.01); *C07D 413/14* (2013.01); *C07D 417/12* (2013.01)

(58) Field of Classification Search
None
See application file for complete search history.

(56) References Cited

U.S. PATENT DOCUMENTS

| 3,188,313 A | 6/1965 | Archer |
| 3,362,956 A | 1/1968 | Archer |

(Continued)

FOREIGN PATENT DOCUMENTS

| CN | 1154693 A | 7/1997 |
| CN | 1944404 A | 4/2007 |

(Continued)

OTHER PUBLICATIONS

Chaudhary et al. European Journal of Medicinal Chemistry 42 (2007) 471-476.*
Non-Final Office Action dated Oct. 2, 2015 in U.S. Appl. No. 14/647,408 by Janet L. Coppins.
Boido, A., et al., "Synthesis and pharmacological evaluation of aryl/heteroaryl piperazinyl alkyl benzotriazoles as ligands for some serotonin and dopamine receptor subtypes", "IL Farmaco", Apr. 2001, pp. 263-275, vol. 56.
Boido, A., et al., "Alpha1- and alpha2-adrenoreceptor antagonist profiles of 1- and 2-[omega-(4-arylpiperazin-1-yl) alkyl]-1,2,3-benzotriazoles", "Chemistry & Biodiversity", Oct. 2005, pp. 1290-1304, vol. 2.

(Continued)

*Primary Examiner* — Emily Bernhardt
(74) *Attorney, Agent, or Firm* — Hultquist, PLLC; Steven J. Hultquist

(57) ABSTRACT

Compounds of formula (I) and its pharmaceutically acceptable salts are described

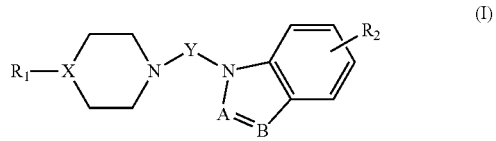

wherein $R_1$, $R_2$, X, Y, A, B are as defined in the specification. Also disclosed are methods for preparing the compounds of formula (I) or pharmaceutically acceptable salts thereof, and pharmaceutical compositions comprising the compounds of formula (I) or pharmaceutically acceptable salts thereof.

10 Claims, 11 Drawing Sheets

Figure 1:
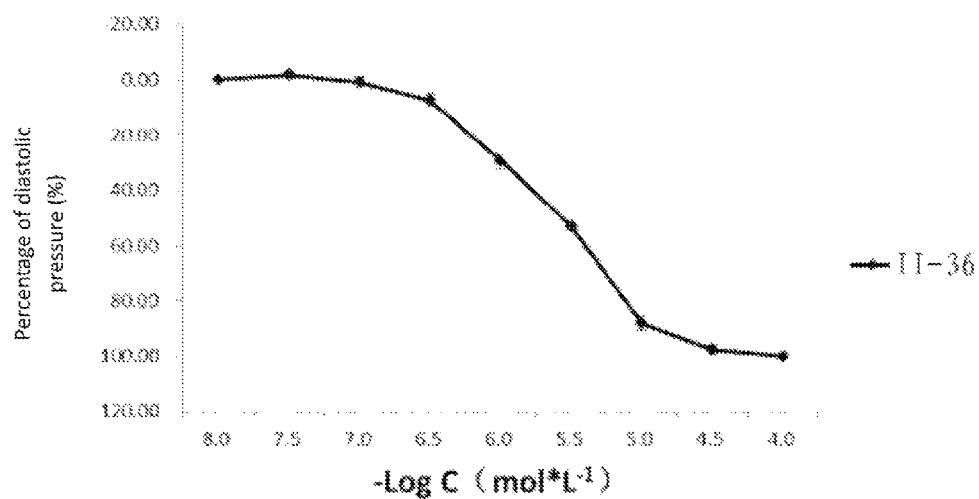

(51) Int. Cl.
  C07D 401/12    (2006.01)
  C07D 235/22    (2006.01)
  C07D 235/24    (2006.01)
  C07D 413/12    (2006.01)
  C07D 235/14    (2006.01)
  C07D 235/04    (2006.01)
  A61K 45/06     (2006.01)
  C07D 235/06    (2006.01)

(56) References Cited

U.S. PATENT DOCUMENTS

| | | | |
|---|---|---|---|
| 3,472,854 A | | 10/1969 | Archer |
| 5,227,486 A * | | 7/1993 | Merce-Vidal ...... C07D 207/325 544/295 |
| 5,382,586 A | | 1/1995 | Merce-Vidal et al. |
| 5,532,234 A * | | 7/1996 | Frigola-Constansa A61K 31/505 514/224.2 |
| 9,415,047 B2 * | | 8/2016 | Zhou .................. A61K 31/496 |
| 2010/0329978 A1 | | 12/2010 | McCurdy et al. |
| 2011/0306638 A1 | | 12/2011 | Li et al. |
| 2015/0297586 A1 | | 10/2015 | Zhou et al. |

FOREIGN PATENT DOCUMENTS

| CN | 101759693 A | 6/2010 |
|---|---|---|
| JP | 04312584 A | 11/1992 |
| JP | 09510706 | 10/1997 |
| WO | 9604250 A1 | 2/1996 |

OTHER PUBLICATIONS

Caliendo, G., et al., "Synthesis and biological activity of benzotriazole derivatives structurally related to trazodone", "European Journal of Medicinal Chemistry", Jan. 1, 1995, pp. 77-84, vol. 30.

Caliendo, G., et al., "Structureaffinity relationship studies on benzotriazole derivatives binding to 5-HT receptor subtypes", "European Journal of Medicinal Chemistry", 1996, pp. 207-213, vol. 31.

Hoyer, D., et al., "International Union of Pharmacology classification of receptors for 5-hydroxytryptamine (Serotonin)", "Pharmacological Reviews", Jun. 1994, pp. 157-203, vol. 46, No. 2.

Mesangeau, C., et al., "Synthesis and pharmacological evaluation of indole-based sigma receptor ligands", "European Journal of Medicinal Chemistry", Aug. 29, 2011, pp. 5154-5161, vol. 46.

Mokrosz, M., et al., "Structure-activity relationship studies of CNS agents, Part 32: Effect of structural modifications in 1-arylpiperazine derivatives on alpha(1)-adrenoreceptor affinity", "Arch. Pharm. (Weinheim).", Jun. 1997, pp. 177-180, vol. 330.

Caliendo, G., et al, "Derivatives as 5HT1A Receptor Ligands—Past and Present", "Current Medicinal Chemistry", 2005, pp. 1721-1753, vol. 12, No. 15.

Mokrosz, J.L., et al., "Structure-Activity Relationship Studies of Central Nervous System Agents. 13. 4-[3-(Benzotriazol-1-yl)propyl]-1-(2-methoxyphenyl)piperazine, a New Putative 5-HT1A Receptor Antagonist, and Its Analogs", "Journal of Medicinal Chemistry", 1994, pp. 2754-2760, vol. 37.

Paluchowska, M. H., et al., "Analogs of MP 3022 with a Different Number of Nitrogen Atoms in the Heteroaromatic Fragment—New 5-HT1A Receptor Ligands", "Archiv der Pharmazie—Pharmaceutical and Medicinal Chemistry", 1996, pp. 451-456, vol. 329.

Wang, G., et al., "Synthesis and biological activities of N-indolalkyl piperidine derivatives and their analogues", "Chinese Journal of Medicinal Chemistry", Jun. 2009, pp. 161-169, vol. 19, No. 3.

Note: For the non-patent literature citations that no month of publication is indicated, the year of publication is more than 1 year prior to the effective filing date of the present application.

* cited by examiner

BENZO FIVE-MEMBERED NITROGEN HETEROCYCLIC PIPERIDINE OR PIPERAZINE DERIVATIVES AND PREPARATION METHODS AND PHARMACEUTICAL COMPOSITIONS THEREOF

CROSS-REFERENCE TO RELATED APPLICATIONS

This application is a U.S. national phase under the provisions of 35 U.S.C. §371 of International Patent Application No. PCT/CN13/01441 filed Nov. 25, 2013, which in turn claims priority of Chinese Patent Application No. 201210487756.4 filed Nov. 26, 2012, Chinese Patent Application No. 201210486659.3 filed Nov. 26, 2012, Chinese Patent Application No. 201210486619.9 filed Nov. 26, 2012, Chinese Patent Application No. 201310409084.X filed Sep. 10, 2013, and Chinese Patent Application No. 201310409567.X filed Sep. 10, 2013. The disclosures of such international patent application and Chinese priority patent applications are hereby incorporated herein by reference in their respective entireties, for all purposes.

TECHNICAL FIELD

The invention relates to five-membered nitrogen heterocyclic piperidine or piperazine derivatives and processes for the preparation of the compound and pharmaceutically acceptable salts. The invention also relates to the pharmaceutical compositions comprising the compounds.

BACKGROUND INFORMATION

Currently, there are several classes of vasodilators for clinical use, for example, $\alpha_1$ receptor antagonists, including prazosin, doxazosin, terazosin, etc., but the significant first dose effect or postural hypotension of these drugs have limited their clinical application; $Ca^{2+}$ channel blockers have been widely used in clinical application, including amlodipine, nifedipine, felodipine etc. But they also show risk of cardiac suppression.

Thus, there remains a need to develop new vasodilators to improve efficacy and reduce side effects, and to meet different clinical needs.

SUMMARY OF THE INVENTION

The present invention provides a compound of the following formula (I) or a pharmaceutically acceptable salt:

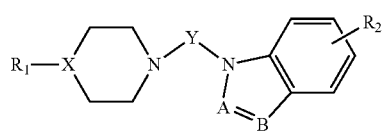

(I)

Where:

$R_1$ represents aromatic group or aliphatic cyclic group mono- or poly-substituted with $R_3$, wherein $R_3$ is H, halogen, CN, $C_1$-$C_6$ alkyl, $C_1$-$C_6$ alkoxy, CHO, CO($C_1$-$C_6$ alkyl), COO($C_1$-$C_6$ alkyl), COOH, $NO_2$, $NH_2$, NH($C_1$-$C_6$ alkyl), N($C_1$-$C_6$alkyl)$_2$, SH, S($C_1$-$C_6$ alkyl), —S(O) ($C_1$-$C_6$ alkyl), —S(O)$_2$H or —S(O)$_2$ ($C_1$-$C_6$ alkyl), and the alkyl of these substitution groups may be substituted with one or more halogens; for poly-substitution, $R_3$ is independently selected from H, halogen, CN, $C_1$-$C_6$ alkyl, $C_1$-$C_6$ alkoxy, CHO, CO($C_1$-$C_6$ alkyl), COO($C_1$-$C_6$ alkyl), COOH, $NO_2$, $NH_2$, NH($C_1$-$C_6$ alkyl), N($C_1$-$C_6$alkyl)$_2$, SH, S($C_1$-$C_6$ alkyl), —S(O)($C_1$-$C_6$ alkyl), —S(O)$_2$H or —S(O)$_2$ ($C_1$-$C_6$ alkyl), and the alkyls of these substitution groups are substituted with one or more halogens;

A, B and X represents CH or N independently;

wherein $R_2$ is H, halogen, CN, $C_1$-$C_6$ alkyl, $C_1$-$C_6$ alkoxy, CHO, CO($C_1$-$C_6$ alkyl, COO($C_1$-$C_6$ alkyl), COOH, $NO_2$, $NH_2$, NH($C_1$-$C_6$ alkyl), N($C_1$-$C_6$alkyl)$_2$, SH, S($C_1$-$C_6$ alkyl), —S(O)($C_1$-$C_6$ alkyl), —S(O)$_2$H or —S(O)$_2$ ($C_1$-$C_6$ alkyl), and the alkyl of these substitution groups may be substituted with one or more halogens; for poly-substitution, $R_2$ may be independently selected from H, halogen, CN, $C_1$-$C_6$ alkyl, $C_1$-$C_6$ alkoxy, CHO, CO($C_1$-$C_6$ alkyl), COO($C_1$-$C_6$ alkyl), COOH, $NO_2$, $NH_2$, NH($C_1$-$C_6$ alkyl), N($C_1$-$C_6$alkyl)$_2$, SH, S($C_1$-$C_6$ alkyl), —S(O) ($C_1$-$C_6$ alkyl), —S(O)$_2$H or —S(O)$_2$ ($C_1$-$C_6$ alkyl), and the alkyls of these substitution groups are substituted with one or more halogens;

Y represents saturated or unsaturated straight or branched 1-8 carbon hydrocarbon chains substituted with one or more halogen, wherein one or more carbon atoms are substituted with hetero-atoms of oxygen, sulfur or nitrogen.

In another aspect, the invention also related to the methods for preparing the compound of formula (I):

Method (I)

Wherein

Under 10-150° C., compound

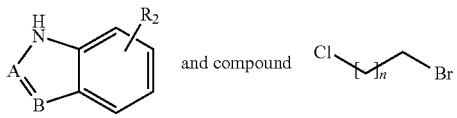 and compound 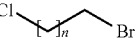

are reacted in reagent in the presence of an inorganic base and a phase transfer catalyst, and result in compound

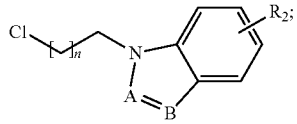

and then after reflux, the resulted compound react with

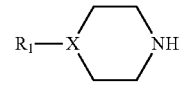

and react in reagent in the presence of an inorganic base and, and result in compound

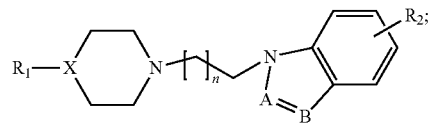

or

Method (II)

Wherein

Under 10-150° C., compound

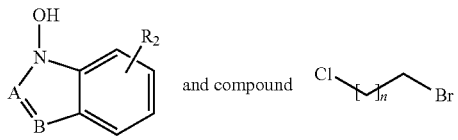

and compound are reacted in reagent in the presence of an inorganic base and a phase transfer catalyst, and result in compound

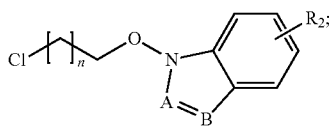

and then after reflux the resulted compound react with

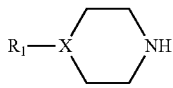

and react in reagent in the presence of an inorganic base and, and result in compound

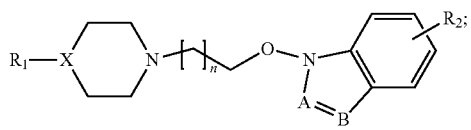

wherein, $R_1$ represents aromatic group or aliphatic cyclic group mono- or poly-substituted with $R_3$, $R_3$ is H, halogen, CN, $C_1$-$C_6$ alkyl, $C_1$-$C_6$ alkoxy, CHO, CO($C_1$-$C_6$ alkyl), COO($C_1$-$C_6$ alkyl), COOH, $NO_2$, $NH_2$, NH($C_1$-$C_6$ alkyl), N($C_1$-$C_6$alkyl)$_2$, SH, S($C_1$-$C_6$ alkyl), —S(O) ($C_1$-$C_6$ alkyl), —S(O)$_2$H or —S(O)$_2$($C_1$-$C_6$ alkyl), and the alkyl of the above groups may be substituted with one or more halogen atoms; if $R_3$ is a poly-substituted group, it is selected independently from the groups above;

A, B and X represent CH or N independently; preferably, A and B represent N;

$R_2$ is H, halogen, CN, $C_1$-$C_6$ alkyl, $C_1$-$C_6$ alkoxy, CHO, CO($C_1$-$C_6$ alkyl), COO($C_1$-$C_6$ alkyl), COOH, $NO_2$, $NH_2$, NH($C_1$-$C_6$ alkyl), N($C_1$-$C_6$alkyl)$_2$, SH, S($C_1$-$C_6$ alkyl), —S(O) ($C_1$-$C_6$ alkyl), —S(O)$_2$H or —S(O)$_2$($C_1$-$C_6$ alkyl), and the alkyl of the above groups may be substituted with one or more halogen atoms; if $R_2$ is a multi-substituted group, it is selected independently from the groups above;

Y represents saturated or unsaturated straight or branched 1-8 carbon hydrocarbon chains substituted with one or more halogen, wherein one or more carbon atoms are substituted with hetero-atoms of oxygen, sulfur or nitrogen.

In addition, this invention relates to the compound of formula (I) and/or its pharmaceutical compositions comprising the compound and its pharmaceutically acceptable salts.

BRIEF DESCRIPTIONS OF THE DRAWINGS

FIG. 1. Compound II-36 ($10^{-8}$-$10^{-4}$ mol·L$^{-1}$) cumulative concentration-response curves of vasodilating effect on rabbits blood vessels constricted by Adrenaline ($10^{-5}$ mol·L$^{-1}$) (Values represent the mean±SEM, shown as (—•—), n=7).

Figure 2:
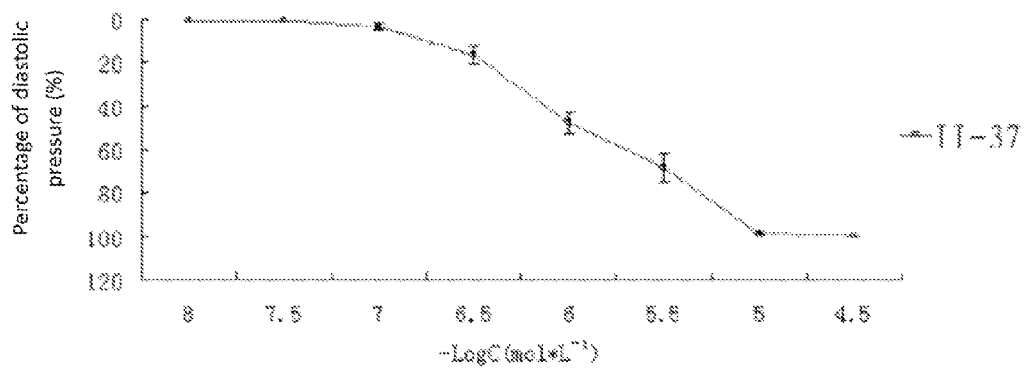

FIG. 2. Compound II-37 ($10^{-8}$-$3\times10^{-5}$ mol·L$^{-1}$) cumulative concentration-response curves of vasodilating effect on rabbits blood vessels constricted by epinephrine ($10^{-5}$ mol·L$^{-1}$) (Values represent the mean±SEM, shown as (—•—), n=6).

Figure 3:
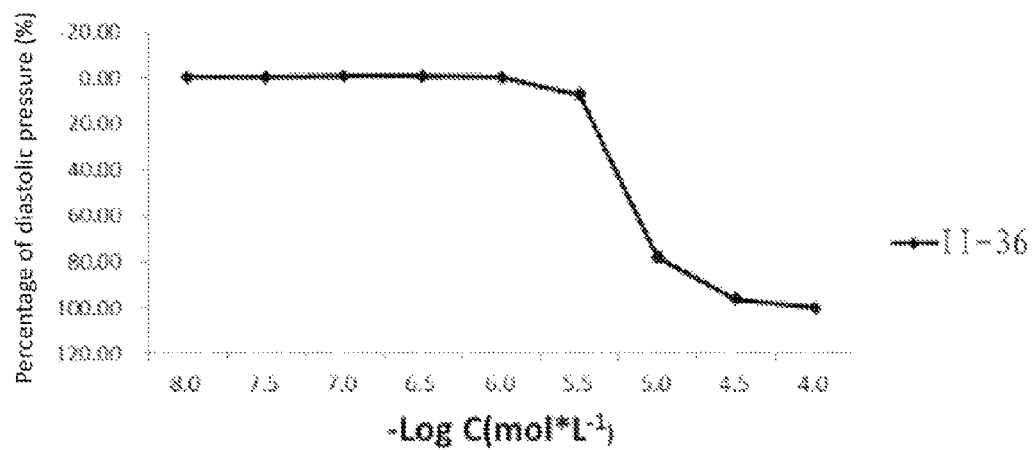

FIG. 3. Compound II-36 ($10^{-8}$-$10^{-4}$ mol·L$^{-1}$) cumulative concentration-response curves of vasodilating effect on rabbits blood vessels constricted by epinephrine ($10^{-5}$ mol·L$^{-1}$) (Values represent the mean±SEM, shown as (—•—), n=8).

Figure 4:
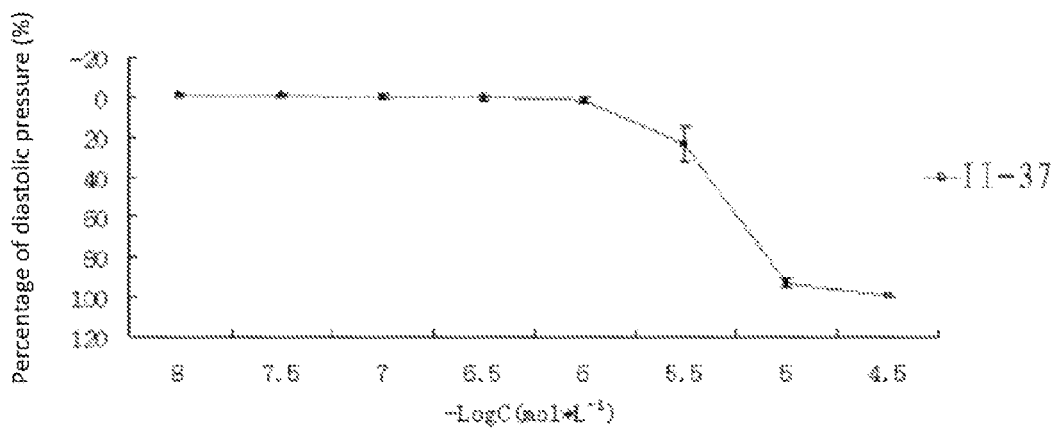

FIG. 4. Compound II-37 ($10^{-8}$-$3\times10^{-5}$ mol·L$^{-1}$) cumulative concentration-response curves of vasodilating effect on rabbits blood vessels constricted by high potassium solution (60 mmol·L$^{-1}$) (Values represent the mean±SEM, shown as (—•—) n=8).

Figure 5:
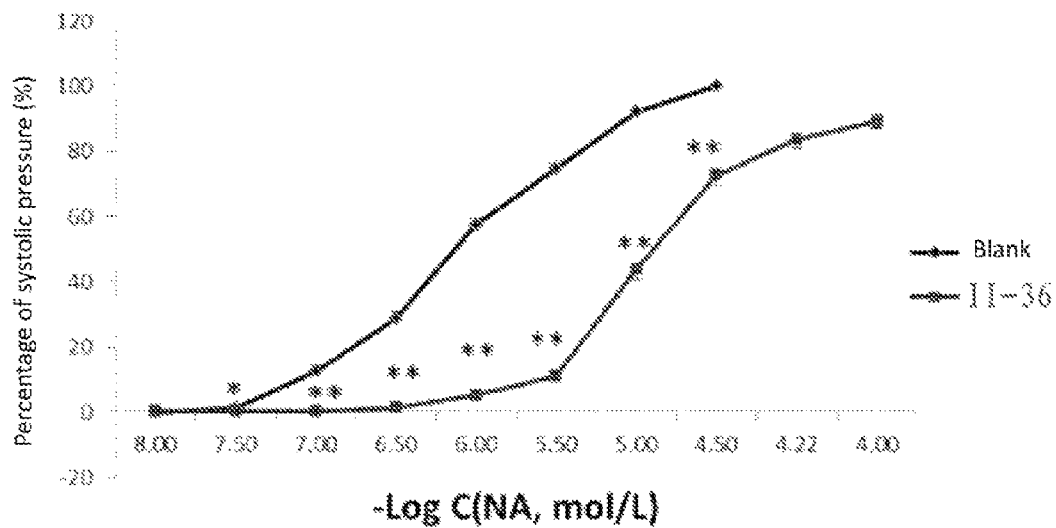

FIG. 5. Compound II-36 ($3\times10^{-7}$ mol/L) cumulative concentration-response curves of antagonistic effect against constriction on rabbits blood vessels by noradrenaline (NA) ($10^{-8}$-$10^{-4}$ mol/L)(Values represent the mean±SEM, shown as (—•—), *P<0.05, **P<0.01, n=8).

Figure 6:
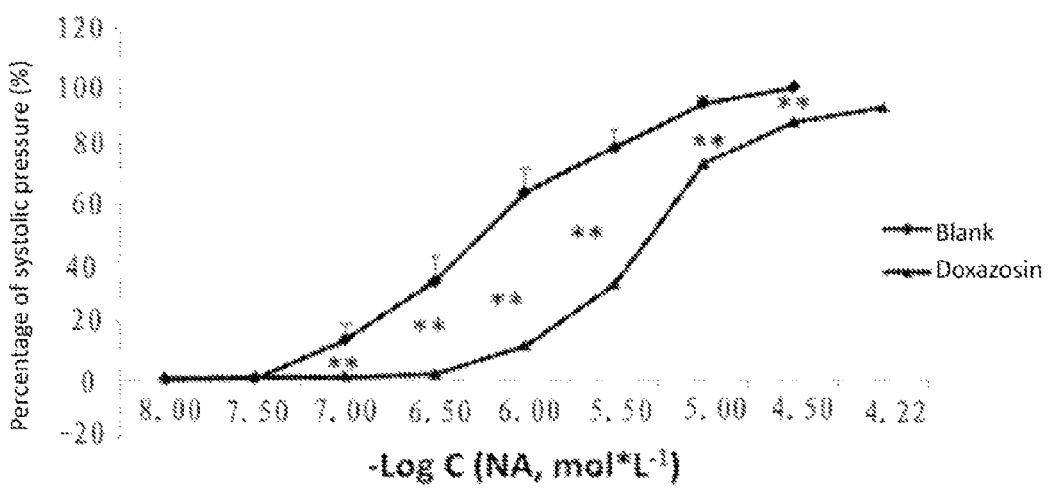

FIG. 6. Positive control Doxazosin ($10^{-7}$ mol/L) cumulative concentration-response curves of antagonistic effect against constriction on rabbits blood vessels by noradrenaline (NA) ($10^{-8}$-$6\times10^{-5}$ mol/L)(Values represent the mean±SEM, shown as (—•—), *P<0.05, **P<0.01, n=8).

Figure 7:
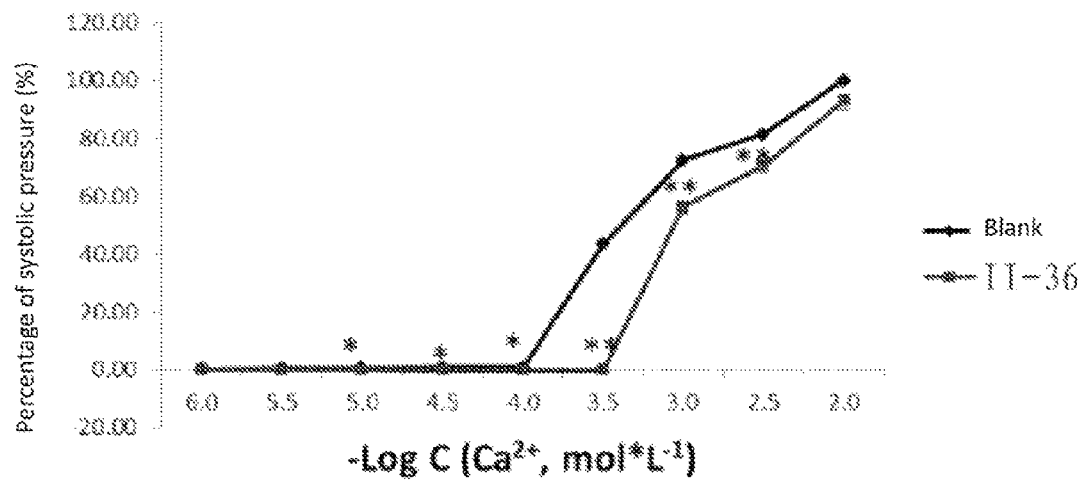

FIG. 7. Compound II-36 ($3\times10^{-6}$ mol/L) cumulative concentration-response curves of antagonistic effect against constriction of rabbits blood vessels by $CaCl_2$ ($10^{-6}$-$10^{-2}$ mol/L) (Values represent the mean±SEM, shown as (—•—), *P<0.05, **P<0.01, n=7).

Figure 8:
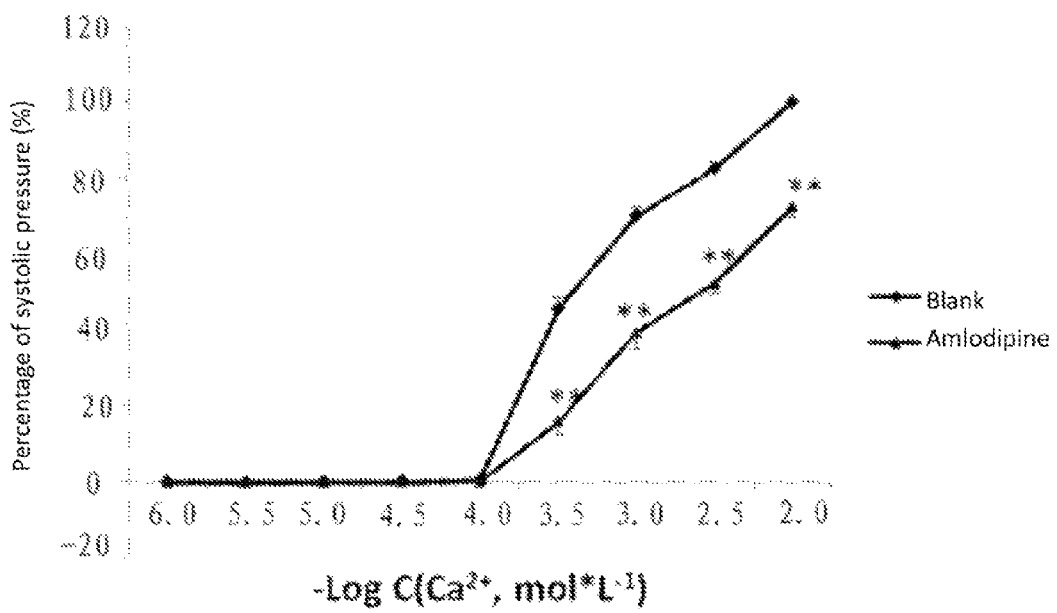

FIG. 8. Amlodipine ($10^{-7}$ mol/L) cumulative concentration-response curves of antagonistic effect against constriction of rabbits blood vessels by $CaCl_2$ ($10^{-6}$-$10^{-2}$ mol/L) (Values represent the mean±SEM, shown as (—•—), *P<0.05, **P<0.01, n=5).

Figure 9:
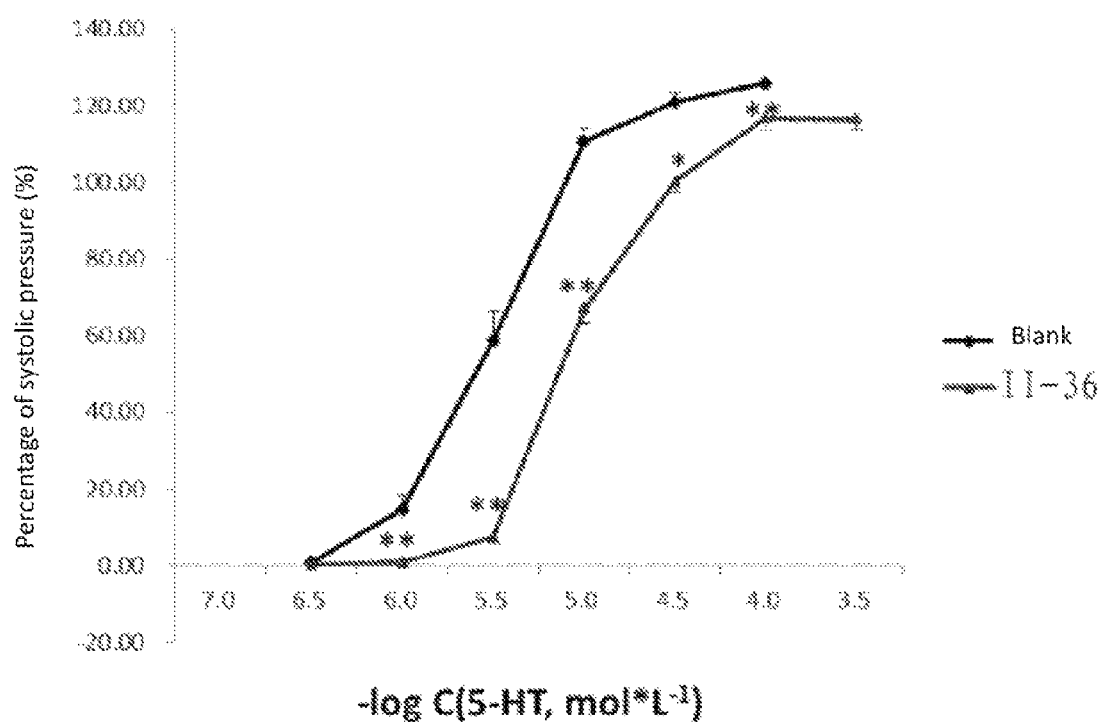

FIG. 9. Compound II-36 ($3\times10^{-6}$ mol/L) cumulative concentration-response curves of antagonistic effect against constriction of rabbits blood vessels by $CaCl_2$ ($10^{-6}$-$10^{-2}$ mol/L) (Values represent the mean±SEM, shown as (—•—), *P<0.05, **P<0.01, n=7).

Figure 10:
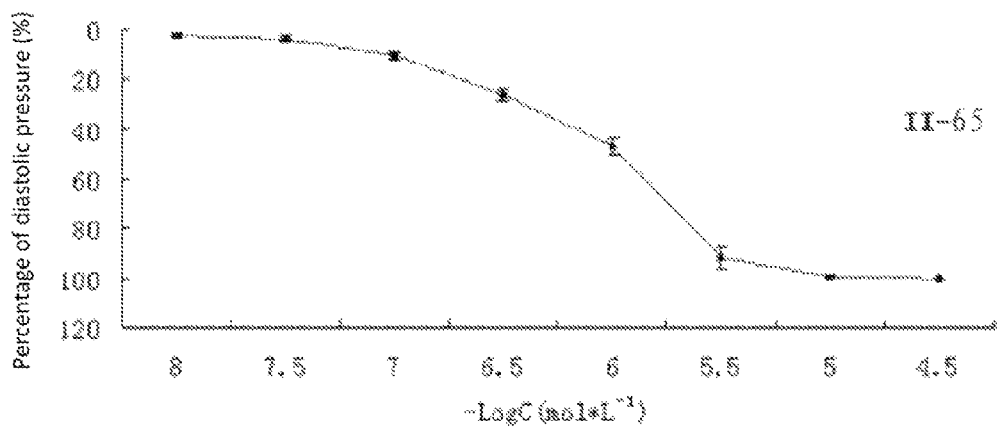

FIG. 10. Compound II-65 ($10^{-8}$-$10^{-5}$ mol·L$^{-1}$) cumulative concentration-response curves of vasodilating effect on rabbits blood vessels constricted by Adrenaline ($10^{-5}$ mol·L$^{-1}$) (Values represent the mean±SEM, shown as (—•—), n=8).

Figure 11:
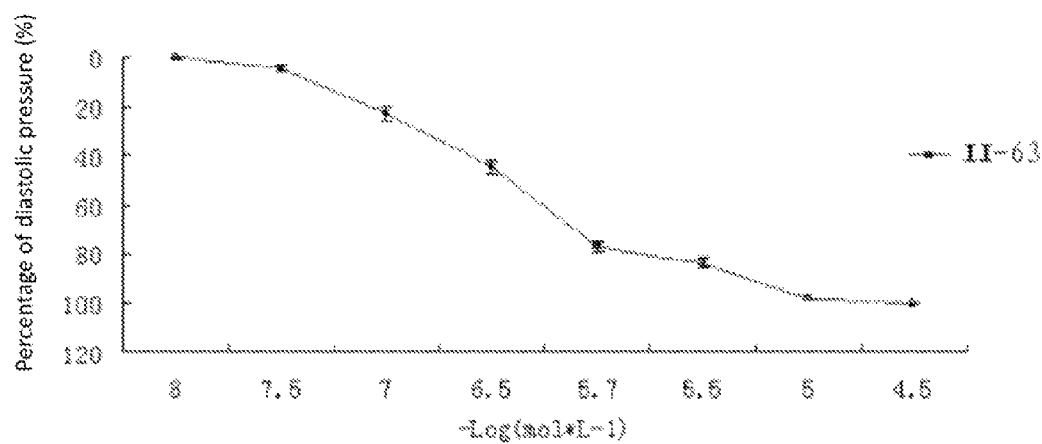

FIG. 11. Compound II-63 ($10^{-8}$-$3\times10^{-5}$ mol·L$^{-1}$) cumulative concentration-response curves of vasodilating effect on rabbits blood vessels constricted by Adrenaline ($10^{-5}$ mol·L$^{-1}$) (Values represent the mean±SEM, shown as (—•—), n=7).

Figure 12:
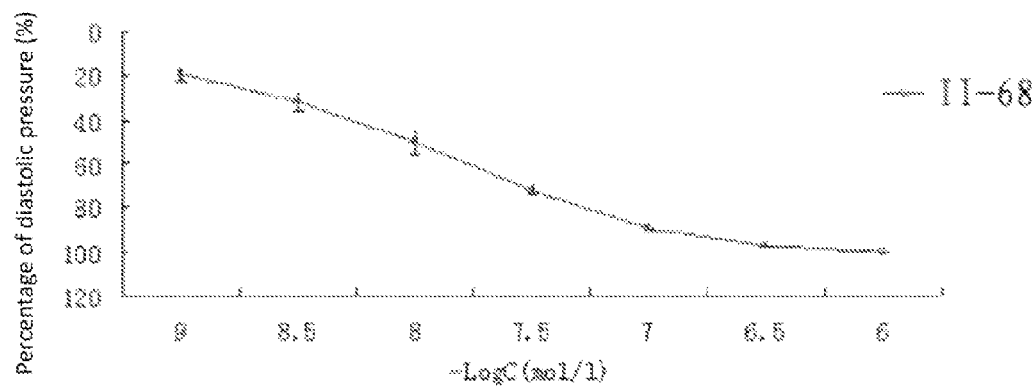

FIG. 12. Compound II-68 ($10^{-9}$-$10^{-6}$ mol/L) cumulative concentration-response curves of vasodilating effect on rabbits blood vessels constricted by Adrenaline ($10^{-5}$ mol·L$^{-1}$) (Values represent the mean±SEM, shown as (—•—), n=7).

Figure 13:
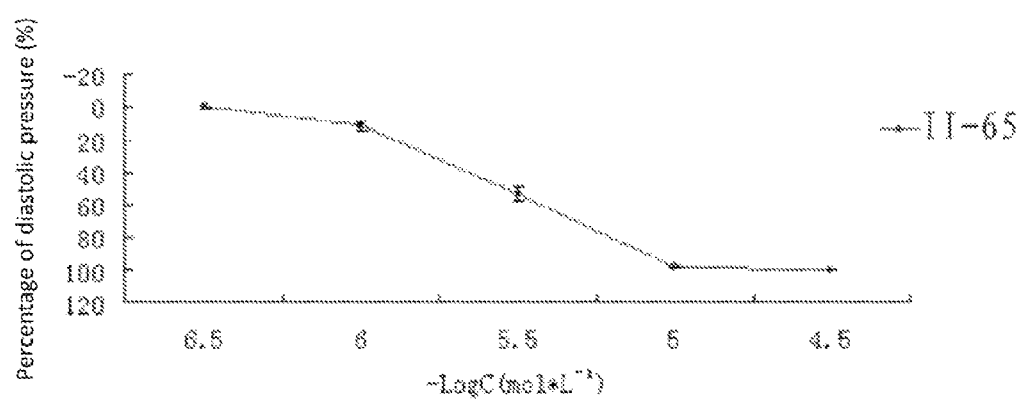

FIG. 13. Compound II-65 ($3\times10^{-7}$-$3\times10^{-5}$ mol·L$^{-1}$) cumulative concentration-response curves of vasodilating effect on rabbits blood vessels constricted by high potassium solution (60 mmol·L$^{-1}$) (Values represent the mean±SEM, shown as (—•—), n=8).

Figure 14:
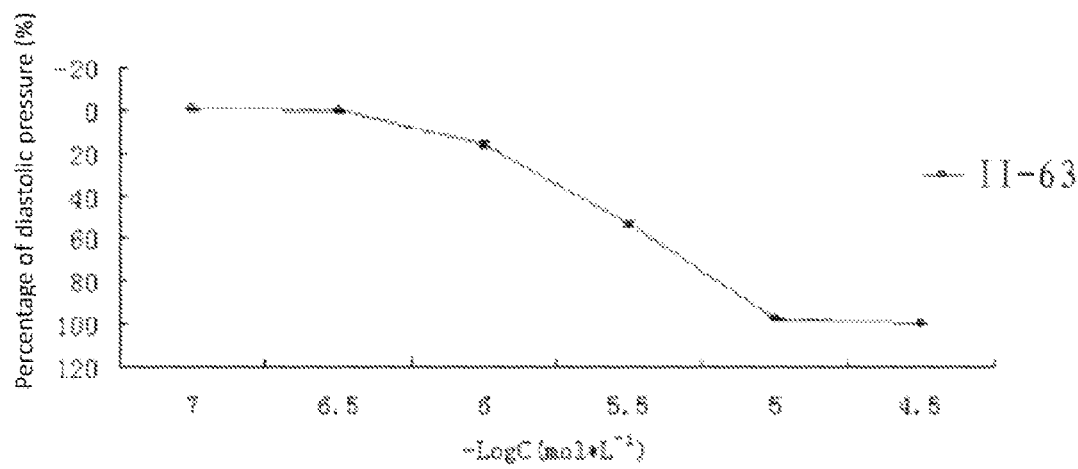

FIG. 14. Compound II-63 ($10^{-7}$-$3\times10^{-5}$ mol·L$^{-1}$) cumulative concentration-response curves of vasodilating effect on rabbits blood vessels constricted by high potassium solution (60 mmol·L$^{-1}$) (Values represent the mean±SEM, shown as (→), n=6).

Figure 15:
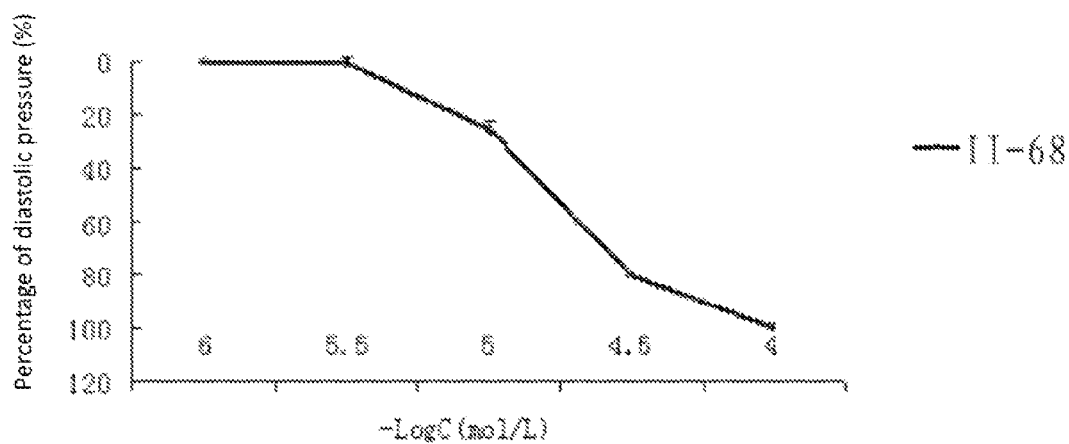

FIG. 15. Compound II-68 ($10^{-8}$-$10^{-4}$ mol/L) cumulative concentration-response curves of vasodilating effect on rabbits blood vessels constricted by high potassium solution (60 mmol·L$^{-1}$) (Values represent the mean±SEM, shown as (→), n=7).

Figure 16:
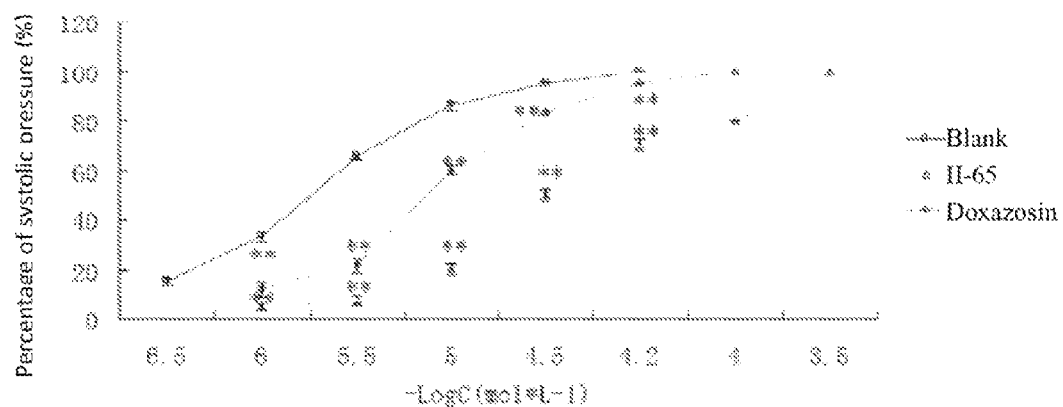

FIG. 16. Compound II-65 ($3\times10^{-6}$ mol/L) and positive control Doxazosin ($10^{-7}$ mol/L) cumulative concentration-response curves of antagonistic effect against constriction on rabbits blood vessels by noradrenaline (NA) ($3\times10^{-7}$-$10^{-4}$ mol/L)(Values represent the mean±SEM, shown as (→), *P<0.05, **P<0.01, n=6).

Figure 17:
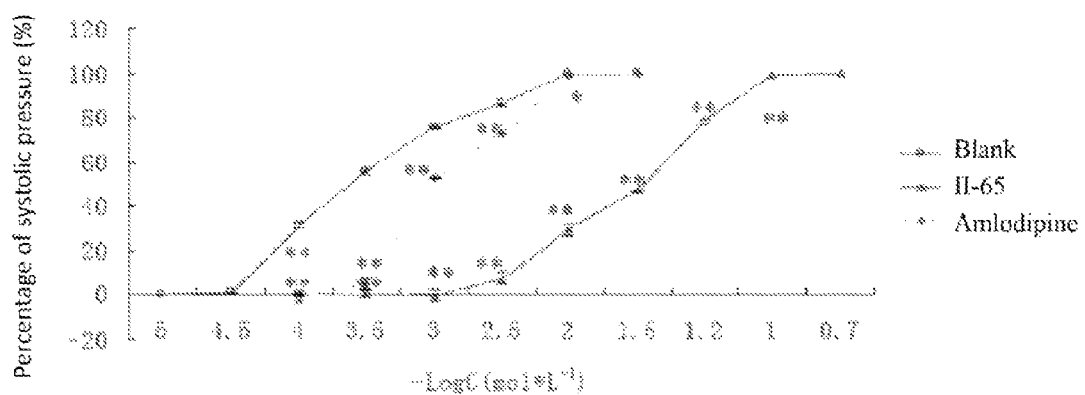

FIG. 17. Compound II-65 ($10^{-5}$ mol/L) and amlodipine ($10^{-7}$ mol/L) cumulative concentration-response curves of antagonistic effect against constriction of rabbits blood vessels by CaCl$_2$ ($10^{-5}$-$3\times10^{-1}$ mol/L) (Values represent the mean±SEM, shown as (→), *P<0.05, **P<0.01, n=7).

Figure 18:
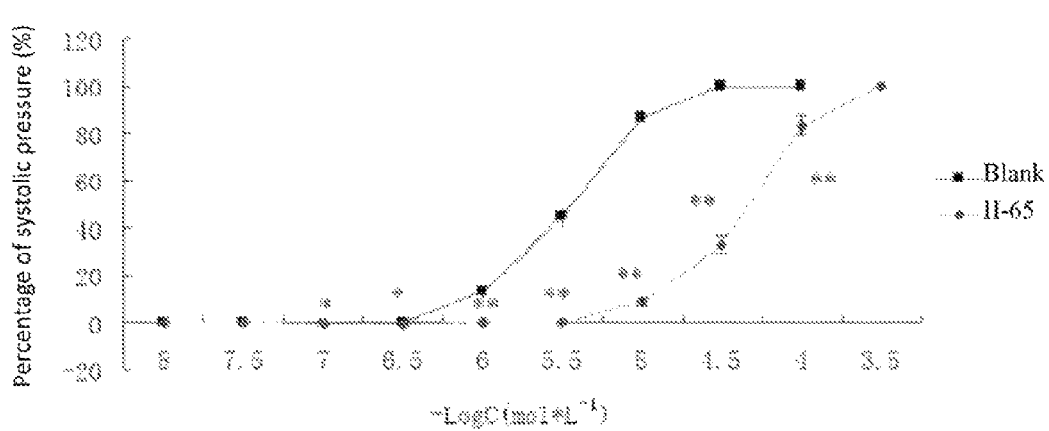

FIG. 18. Compound II-65 ($3\times10^{-6}$ mol/L) cumulative concentration-response curves of antagonistic effect against constriction of rabbits blood vessels by Serotonin ($10^{-8}$-$3\times10^{-4}$ mol/L)(Values represent the mean±SEM, shown as (→), *P<0.05, **P<0.01, n=5).

Figure 19:
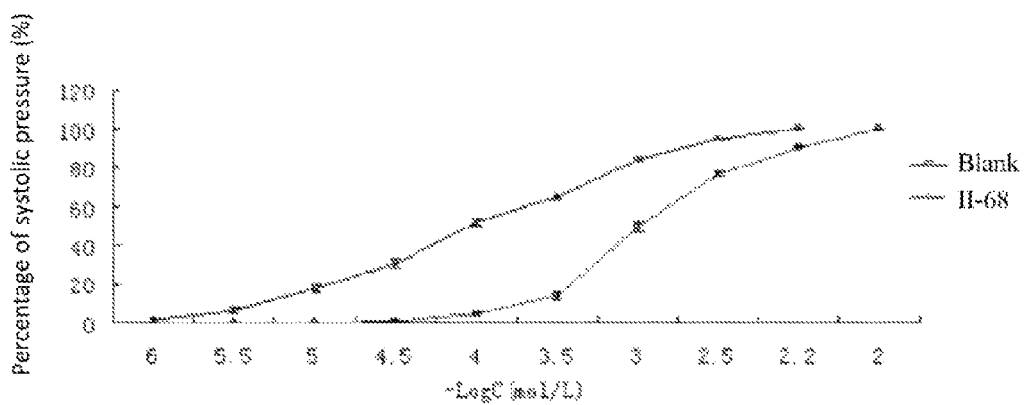

FIG. 19. Compound II-68 ($3\times10^{-8}$ mol/L) cumulative concentration-response curves of antagonistic effect against constriction of rabbits blood vessels by Phenylephrine ($10^{-6}$-$6\times10^{-3}$ mol/L) (Values represent the mean±SEM, shown as (→), *P<0.05, **P<0.01, n=8).

Figure 20:
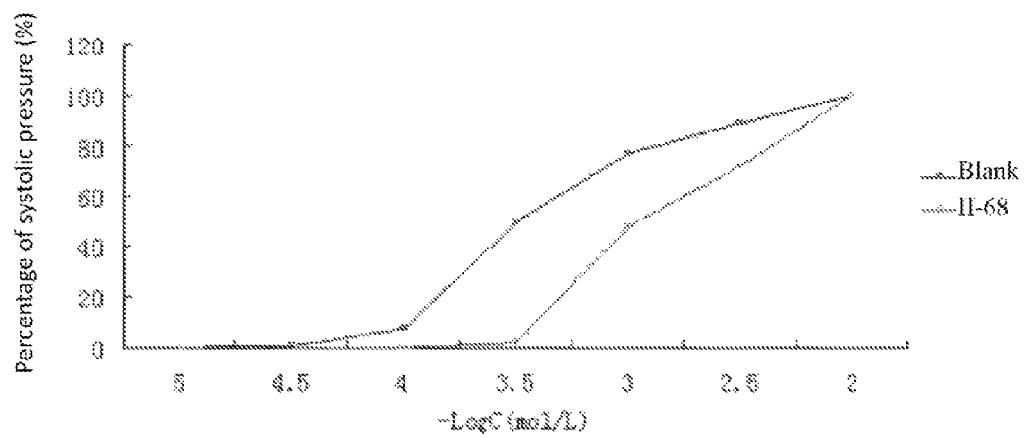

FIG. 20. Compound II-68 ($10^{-5}$ mol/L) cumulative concentration-response curves of antagonistic effect against constriction of rabbits blood vessels by CaCl$_2$ ($10^{-5}$-$10^{-2}$ mol/L) (Values represent the mean±SEM, shown as (→), *P<0.05, **P<0.01, n=7).

Figure 21:
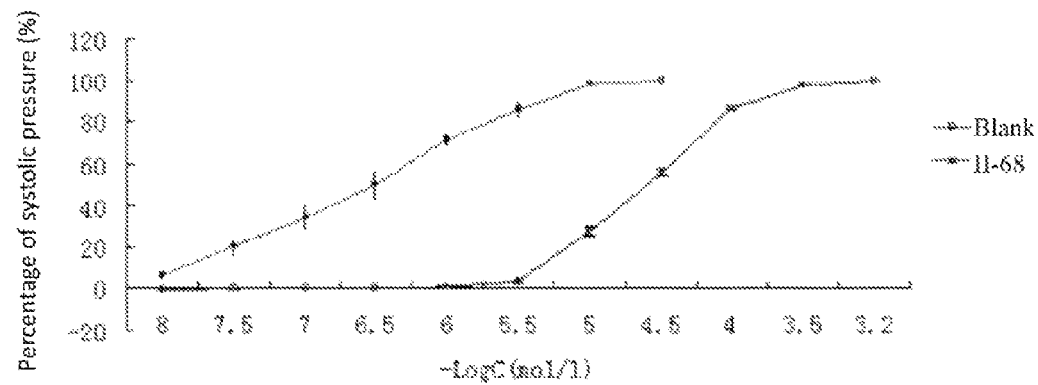

FIG. 21. Compound II-68 ($10^{-7}$ mol/L) cumulative concentration-response curves of antagonistic effect against constriction of rabbits blood vessels by Serotonin ($10^{-8}$-$3\times10^{-4}$ mol/L) (Values represent the mean±SEM, shown as (→), *P<0.05, **P<0.01, n=5).

DETAILED EMBODIMENT

The present invention provides a compound of the following formula (I) or a pharmaceutically acceptable salt:

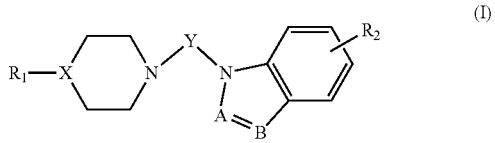

(I)

Where:

R$_1$ represents aromatic group or aliphatic cyclic group mono- or poly-substituted with R$_3$, wherein R$_3$ is H, halogen, CN, C$_1$-C$_6$ alkyl, C$_1$-C$_6$ alkoxy, CHO, CO(C$_1$-C$_6$ alkyl, COO(C$_1$-C$_6$ alkyl), COOH, NO$_2$, NH$_2$, NH(C$_1$-C$_6$ alkyl), N(C$_1$-C$_6$alkyl)$_2$, SH, S(C$_1$-C$_6$ alkyl), —S(O) (C$_1$-C$_6$ alkyl), —S(O)$_2$H or —S(O)$_2$(C$_1$-C$_6$ alkyl), and the alkyl of these substitution groups may be substituted with one or more halogens; for poly-substitution, R$_3$ is independently selected from H, halogen, CN, C$_1$-C$_6$ alkyl, C$_1$-C$_6$ alkoxy, CHO, CO(C$_1$-C$_6$ alkyl), COO(C$_1$-C$_6$ alkyl), COOH, NO$_2$, NH$_2$, NH(C$_1$-C$_6$ alkyl), N(C$_1$-C$_6$alkyl)$_2$, SH, S(C$_1$-C$_6$ alkyl), —S(O) (C$_1$-C$_6$ alkyl), —S(O)$_2$H or —S(O)$_2$ (C$_1$-C$_6$ alkyl), and the alkyls of these substitution groups are substituted with one or more halogens;

A, B and X represents CH or N independently;

wherein R$_2$ is H, halogen, CN, C$_1$-C$_6$ alkyl, C$_1$-C$_6$ alkoxy, CHO, CO(C$_1$-C$_6$ alkyl), COO(C$_1$-C$_6$ alkyl), COOH, NO$_2$, NH$_2$, NH(C$_1$-C$_6$ alkyl), N(C$_1$-C$_6$alkyl)$_2$, SH, S(C$_1$-C$_6$ alkyl), —S(O) (C$_1$-C$_6$ alkyl), —S(O)$_2$H or —S(O)$_2$ (C$_1$-C$_6$ alkyl), and the alkyl of these substitution groups may be substituted with one or more halogens; for poly-substitution, R$_2$ may be independently selected from H, halogen, CN, C$_1$-C$_6$ alkyl, C$_1$-C$_6$ alkoxy, CHO, CO(C$_1$-C$_6$ alkyl), COO(C$_1$-C$_6$ alkyl), COOH, NO$_2$, NH$_2$, NH(C$_1$-C$_6$ alkyl), N(C$_1$-C$_6$alkyl)$_2$, SH, S(C$_1$-C$_6$ alkyl), —S(O) (C$_1$-C$_6$ alkyl), —S(O)$_2$H or —S(O)$_2$ (C$_1$-C$_6$ alkyl), and the alkyls of these substitution groups are substituted with one or more halogens;

Y represents saturated or unsaturated straight or branched 1-8 carbon hydrocarbon chains substituted with one or more halogen, wherein one or more carbon atoms are substituted with hetero-atoms of oxygen, sulfur or nitrogen.

Preferably in this formula (I), R$_2$ is a mono- or poly-substitution of the five-membered nitrogen heterocyclic ring. It can be a mono-, bi- or tri-substitution; R$_2$ can be a group bound to any carbon atoms of the ring; it can be bound to A (or B) when A (or B) is CH.

The term aromatic group herein refers to a single hydrocarbon ring or double hydrocarbon ring in which at least one aromatic ring, and one or more carbon atoms are substituted with oxygen, sulfate and/or nitrogen. Aromatic group can be (hetero) aryl, including phenyl, naphthyl, benzothiazolyl, benzisothiazolyl, benzoxazolyl, benzisoxazolyl, benzimidazolyl, benzopyrazolyl, benzofuranyl, benzo-pyrimidinyl, benzo-pyridyl, quinoxaline, furanyl, pyridyl or pyrimidinyl.

The term aryl herein includes phenyl, naphthyl or indenyl etc.

The aliphatic cyclic group herein can be C$_{5-12}$ monocyclic saturated cyclic hydrocarbon or bicyclic saturated cyclic hydrocarbon group, in which one or more carbon atoms are substituted with oxygen, sulfate and/or nitrogen. Examples of the aliphatic cyclic groups include cyclopropyl, cyclobutyl, cyclopentyl, cyclohexyl, cycloheptyl, tetrahydrofuranyl, piperidinyl or piperazinyl group etc.

Unless otherwise specified, the term halogen refers to fluorine, chlorine, bromine or iodine.

The term alkyl used herein includes straight or branched chain alkyl group. Examples of the C$_1$-C$_6$ alkyl group include methyl, ethyl, n-propyl, isopropyl, butyl, isobutyl, tert-butyl, n-pentyl, isopentyl, tert-amyl, n-hexyl, isohexyl etc.

The term alkoxy herein refers to —O-alkyl, wherein alkyl includes straight-chain or branched-chain alkyl group. Examples of the "C$_1$-C$_6$ alkyl group" include methoxy, ethoxy, propoxy, butoxy, pentyloxy and hexyloxy etc.

The adjectives herein can be used in combined, including general, preferred, more preferred, even more preferred, particularly preferred, most preferred.

In some embodiments, this invention relates to the compound with formula (I) and its pharmaceutically acceptable salt.

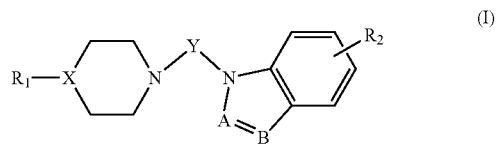

(I)

Where:

$R_1$ represents aromatic group or aliphatic cyclic group mono- or poly-substituted with $R_3$, wherein $R_3$ is H, halogen, CN, $C_1$-$C_6$ alkyl, $C_1$-$C_6$ alkoxy, CHO, CO($C_1$-$C_6$ alkyl), COO($C_1$-$C_6$ alkyl), COOH, $NO_2$, $NH_2$, NH($C_1$-$C_6$ alkyl), N($C_1$-$C_6$alkyl)$_2$, SH, S($C_1$-$C_6$ alkyl), —S(O) ($C_1$-$C_6$ alkyl), —S(O)$_2$H or —S(O)$_2$ ($C_1$-$C_6$ alkyl), and the alkyl of these substitution groups may be substituted with one or more halogens; for poly-substitution, $R_3$ is independently selected from H, halogen, CN, $C_1$-$C_6$ alkyl, $C_1$-$C_6$ alkoxy, CHO, CO($C_1$-$C_6$ alkyl), COO($C_1$-$C_6$ alkyl), COOH, $NO_2$, $NH_2$, NH($C_1$-$C_6$ alkyl), N($C_1$-$C_6$alkyl)$_2$, SH, S($C_1$-$C_6$ alkyl), —S(O) ($C_1$-$C_6$ alkyl), —S(O)$_2$H or —S(O)$_2$ ($C_1$-$C_6$ alkyl), and the alkyls of these substitution groups are substituted with one or more halogens;

A, B and X represents CH or N independently;

wherein $R_2$ is H, halogen, CN, $C_1$-$C_6$ alkyl, $C_1$-$C_6$ alkoxy, CHO, CO($C_1$-$C_6$ alkyl), COO($C_1$-$C_6$ alkyl), COOH, $NO_2$, $NH_2$, NH($C_1$-$C_6$ alkyl), N($C_1$-$C_6$alkyl)$_2$, SH, S($C_1$-$C_6$ alkyl), —S(O) ($C_1$-$C_6$ alkyl), —S(O)$_2$H or —S(O)$_2$ ($C_1$-$C_6$ alkyl), and the alkyl of these substitution groups may be substituted with one or more halogens; for poly-substitution, $R_2$ may be independently selected from H, halogen, CN, $C_1$-$C_6$ alkyl, $C_1$-$C_6$ alkoxy, CHO, CO($C_1$-$C_6$ alkyl), COO($C_1$-$C_6$ alkyl), COOH, $NO_2$, $NH_2$, NH($C_1$-$C_6$ alkyl), N($C_1$-$C_6$alkyl)$_2$, SH, S($C_1$-$C_6$ alkyl), —S(O) ($C_1$-$C_6$ alkyl), —S(O)$_2$H or —S(O)$_2$ ($C_1$-$C_6$ alkyl), and the alkyls of these substitution groups are substituted with one or more halogens;

Y represents saturated or unsaturated straight or branched hydrocarbon chains, with 1-8 carbon atoms substituted with one or more halogen, wherein one or more carbon atoms are substituted with hetero-atoms of oxygen, sulfur or nitrogen;

but all A, B and X have to be N.

The aromatic group is not pyrimidinyl, benzopyrazolyl, thienyl and pyrimidinyl, oxazolyl and pyrimidinyl or purinyl;

If poly-substituted, $R_2$ are not all H when $R_1$ is an aryl group mono-substituted with Cl and Y represents a methylene group or an ethylene group;

If poly-substituted, $R_2$ are not all H when $R_1$ is an aryl group mono-substituted with $CF_3$ and Y represents a methylene group;

If poly-substituted, $R_2$ are not all H when Y represents a methylene group; or $R_3$ is not H when $R_2$ are bi-substituted in meta- and para-position and both groups are $OCH_3$.

In a detailed embodiment, the present invention provides a compound of the following formula (I) or a pharmaceutically acceptable salt:

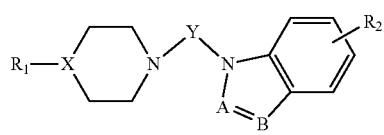

(I)

Where:

$R_1$ represents aromatic group or aliphatic cyclic group mono- or poly-substituted with $R_3$, The aromatic group is a benzo five-membered ring or six-membered heterocyclic ring, preferably selected from a phenyl group, a naphthyl group, and a hetero atom selected from N, S, O, or it is a five- or six-membered unsaturated heterocyclic ring; more preferably, phenyl, naphthyl, benzothiazolyl, benzisothiazolyl, benzoxazolyl, benzisoxazolyl, benzimidazolyl, benzo-pyrazolyl, benzofuranyl, benzo-pyrimidinyl, benzo-pyridyl, quinoxaline, furanyl, pyridyl or pyrimidinyl; still more preferably, a phenyl group, benzisoxazolyl, benzisothiazole, benzo-pyrazolyl, benzofuryl, naphthyl, furanyl, pyridyl, pyrimidinyl or quinoxaline group; and preferably phenyl, pyridyl, benzofuranyl, benzisothiazolyl, benzisoxazolyl or quinoxaline group; particularly preferably phenyl, benzisoxazolyl or benzisothiazole; preferably, A is N when the aromatic group is benzisoxazolyl or benzisothiazole time;

The aliphatic cyclic group described is preferably a five- or six-membered saturated cyclic hydrocarbon group, or a five- or six-membered saturated heterocyclic group with hetero atoms selected from N, S and O; more preferably, a cyclopentyl, cyclohexyl, tetrahydrofuranyl, piperidinyl or piperazinyl group; still more preferably, cyclohexyl, piperidyl or piperazinyl group; and particularly preferably, a cyclohexyl group;

$R_3$ is H, halogen, CN, $C_1$-$C_6$ alkyl, $C_1$-$C_6$ alkoxy, CHO, CO($C_1$-$C_6$ alkyl), COO($C_1$-$C_6$ alkyl), COOH, $NO_2$, $NH_2$, NH(C1-$C_6$ alkyl), N($C_1$-$C_6$ alkyl)$_2$, SH, S($C_1$-$C_6$ alkyl), —S(O) ($C_1$-$C_6$ alkyl), —S(O)$_2$H, or —S(O)$_2$ ($C_1$-$C_6$ alkyl), and the alkyl of the above groups is optionally substituted with one or more halogen atoms; preferably, $R_3$ is H, halogen, CN, $C_1$-$C_6$ alkyl, $C_1$-$C_6$ alkyl alkoxy, CHO, CO($C_1$-$C_6$ alkyl), COO($C_1$-$C_6$ alkyl) or COOH, the alkyl of the above groups optionally substituted with one or more (e.g., one to three) halogen atoms; more preferably, $R_3$ is H, F, Cl, Br, CN, and the alkyl is optionally $C_1$-$C_6$ alkyl or $C_1$-$C_6$ alkoxy substituted with 1 to 3 halogen atoms, CHO, $COCH_3$ or $COOCH_3$; still preferably, $R_3$ is H, F, Cl, $COCH_3$, alkyl, a $C_1$-$C_4$ alkyl or $C_1$-$C_4$ alkoxy group optionally substituted with 1-3 halogen atoms; even more preferably, $R_3$ is H, F, Cl, CN, $CF_3$, $CH_3$, $OCH_3$ or $COCH_3$; when $R_3$ are poly-substituent groups, $R_3$ are independently selected from the group described above;

A, B and X represent CH or N independently; preferably, A and B represent N;

$R_2$ is H, halogen, CN, $C_1$-$C_6$ alkyl, $C_1$-$C_6$ alkoxy, CHO, CO($C_1$-$C_6$ alkyl), COO($C_1$-$C_6$ alkyl), COOH, $NO_2$, $NH_2$, NH(C1-$C_6$ alkyl), N($C_1$-$C_6$alkyl)$_2$, SH, S($C_1$-$C_6$ alkyl), —S(O) ($C_1$-$C_6$ alkyl), —S(O)$_2$H, or —S(O)$_2$($C_1$-$C_6$ alkyl), and the alkyl of the above groups is optionally substituted with one or more halogen atoms; preferably, $R_2$ is H, halogen, CN, $C_1$-$C_6$ alkyl, $C_1$-$C_6$ alkyl alkoxy, CHO, CO($C_1$-$C_6$ alkyl), COO($C_1$-$C_6$ alkyl) or COOH, and the alkyl of the above groups are optionally substituted with one or more (e.g., one to three) halogen atoms; more preferably, $R_2$ is H, F, Cl, Br, CN, and the alkyl is optionally $C_1$-$C_6$ alkyl or $C_1$-$C_6$ alkoxy substituted with 1 to 3 halogen atoms, CHO, $COCH_3$ or $COOCH_3$; still preferably, $R_2$ is H, F, Cl, $COCH_3$, alkyl, a $C_1$-$C_4$ alkyl or $C_1$-$C_4$ alkoxy group optionally substituted with 1-3 halogen atoms; even more preferably, $R_2$ is H, F, Cl, CN, $CF_3$, $CH_3$, $OCH_3$ or $COCH_3$; when $R_2$ are poly-substituent groups, they are independently selected from the groups described above;

Optionally, Y represents saturated or unsaturated, straight or branched hydrocarbon chain (with 1 to 8 carbon atoms) substituted with one or more (e.g., 1 to 3) halogen atoms substituted, in which one or more carbon is optionally substituted with hetero-atoms including oxygen, sulfur, and nitrogen; preferably, Y is unsubstituted saturated 1-8 carbon hydrocarbon group or 1-8 carbon saturated hydrocarbon group where one carbon atom is replaced by oxygen or sulfur, e.g., —$C_{1-7}$ alkylene-O—; Y is more preferably a methylene, ethylene, propylene, butylene, pentylene, hexylene, heptylene, octadienyl, oxymethylene, oxyethylene, oxypropylene, oxyalkylene group, oxyalkylene pentyl, hexyl, oxyalkylene, oxyalkylene heptyl group, methylene group, ethylene group, propylene group, butylene group, pentylene group, hexylene group or an alkylene group, heptyl group; still more preferably, Y is methylene, ethylene, propylene, butylene, pentylene, hexylene, heptylene, octylene, methylene group, ethylene group, propylene group, butylene group, pentylene group, hexylene alkylene group or heptyl group; and particularly preferably ethylene, propylene, butylene, ethyleneoxy or propyleneoxy; most preferably propylene or butylene.

In a preferred embodiment, the present invention provides a compound of the following formula (I) or a pharmaceutically acceptable salt:

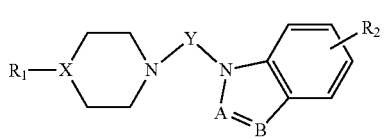

Where:
R₁ represents aromatic group mono- or bi-substituted by R₃, wherein
the aromatic group is preferably a phenyl group, benzisothiazole or benzisoxazolyl; preferably, A, B, X are N when the aromatic group is benzisothiazolyl or benzisoxazole;
R₃ is H, halogen (e.g. F, Cl), CF₃, CN or CH₃; when R₃ are a bi-substitution groups, R₃ are independently selected from the above group;
A, B and X represent CH or N independently; preferably, A and B represent N;
R₂ represents H or halogen (such as F); when R₂ are poly-substitution groups, R₃ is independently selected from the group described above;
Y represents an ethylene group or a propylene group.

In another detailed embodiment, the present invention provides a compound of the following formula (I) or a pharmaceutically acceptable salt:

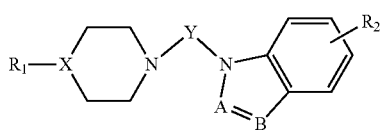

Where:
R₁ represents aromatic group mono-substituted with R₃, wherein
the aromatic group is preferably a phenyl group or benzisothiazole; preferably, A is N when the aromatic group is benzisothiazolyl or benzisoxazole;
R₃ is H, halogen (e.g., F and Cl), CF₃, CH₃ or OCH₃;
A and B represent CH or N independently, preferably N;
X is CH;
R₂ is H, halogen (e.g., F and Cl), CN, CH₃, OCH₃ or CHO;
Y represents an ethylene, propylene, butylene or propylene group.

In another one more detailed embodiment, the present invention provides a compound of the following formula (I) or a pharmaceutically acceptable salt:

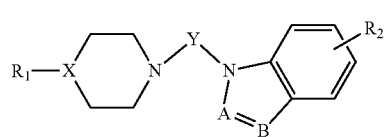

Where:
R₁ represents aromatic group mono-substituted with R₃, wherein
the aromatic group is preferably a phenyl group or benzisothiazole; preferably, A is N when the aromatic group is benzisothiazolyl or benzisoxazole;
R₃ is H or CF₃;
A and B represent CH or N independently, preferably N;
X is CH;
R₂ represents H or OCH₃;
Y represents a propylene or butylene.

In another one more detailed embodiment, the present invention provides a compound of the following formula (I) or a pharmaceutically acceptable salt:

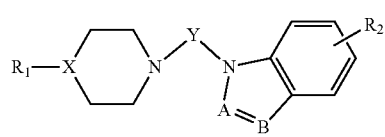

Where: X is CH when A and B are both N,
R₁ is not 6-fluoro-substituted benzisoxazolyl;
R₂ is not H or Cl; and
Y is not ethyleneoxy or propylene group.

In another one more detailed embodiment, the present invention provides a compound of the following formula (I) or a pharmaceutically acceptable salt:

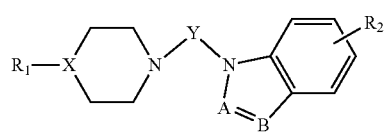

Where: When A, B and X are CH,
R₁ is not 6-fluoro-substituted benzisoxazolyl;
R₂ is not H, F, CN, COOCH₃ or Cl; and
Y is not ethylene, propylene, butylene, pentylene, ethyleneoxy or propyleneoxy.

In another one more detailed embodiment, the present invention provides a compound of the following formula (I) or a pharmaceutically acceptable salt:

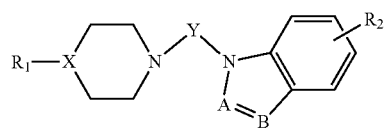

Where: When only one of A and B is CH and the other is N, and X is CH,
R₁ is not 6-fluoro-substituted benzisoxazolyl;

$R_2$ is not H, F, or CN; and
Y is not propylene or butylene.

In another detailed embodiment, the present invention provides a compound of the following formula (I) or a pharmaceutically acceptable salt:

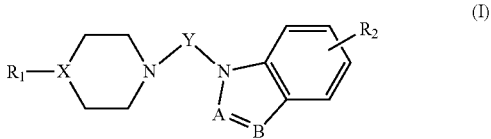

(I)

Where:
$R_1$ represents aromatic group mono- or bi-substituted by $R_3$, wherein
the aromatic group is preferably a phenyl group, benzisothiazole or benzisoxazolyl; preferably, A and B are N when the aromatic group is benzisothiazolyl or benzisoxazole time;
$R_3$ is H, halogen (e.g. F, Cl), $CF_3$, CN or $CH_3$; when $R_3$ are a bi-substitution groups, $R_3$ are independently selected from the above group;
A and B represent CH or N independently, preferably N; X is N;
$R_2$ represents H or halogen (such as F); when $R_2$ are poly-substitution groups, $R_3$ is independently selected from the group described above;
Y represents an ethylene group or a propylene group.

In another one more detailed embodiment, the present invention provides a compound of the following formula (I) or a pharmaceutically acceptable salt:

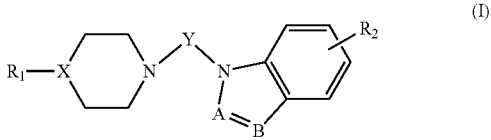

(I)

Where:
$R_1$ represents aromatic group mono- or bi-substituted by $R_3$, wherein
the aromatic group is preferably a phenyl group or benzisothiazole; preferably, A and B are N when the aromatic group is benzisothiazolyl;
$R_3$ is H, Cl or $CF_3$; when $R_3$ are bi-substitution groups, $R_3$ are independently selected from the above group;
A and B represent CH or N independently, preferably N; X is N;
$R_2$ represents H;
Y represents a butylene.

The benzo five-membered heterocyclic piperidine or piperazine compounds include:
I-1 N-(4-(1H-benzimidazol-1-yl)butyl)-4-(3-chlorophenyl) piperidine,
I-2 N-(4-(1H-benzotriazole-1-yl)butyl)-4-(3-chlorophenyl) piperidine,
I-3 N-(4-(1H-benzimidazol-1-yl)butyl)-4-(3-trifluoromethylphenyl)piperidine,
I-4 N-(4-(1H-benzotriazole-1-yl)butyl)-4-(3-trifluoromethylphenyl)piperidine,
I-5 N-(4-(1H-benzimidazol-1-yl)butyl)-4-(3-fluorophenyl) piperidine,
I-6 N-(4-(1H-benzimidazol-1-yl)butyl)-4-(2-methoxyphenyl)piperidine,
I-7 N-(4-(6-fluoro-1H-benzotriazole-1-yl)butyl)-4-(3-trifluoromethylphenyl)piperidine,
I-8 N-(4-(6-methoxy-1H-benzotriazole-1-yl)butyl)-4-(3-trifluoromethylphenyl)piperidine,
I-9 N-(4-(6-cyano-1H-benzotriazole-1-yl)butyl)-4-(3-trifluoromethylphenyl)piperidine,
I-10 N-(4-(1H-benzotriazole-1-yl)propoxy)-4-(3-trifluoromethylphenyl)piperidine,
I-11 N-(4-(1H-benzimidazol-1-yl)propoxy)-4-(3-trifluoromethylphenyl)piperidine,
I-12 N-(3-(1H-benzotriazole-1-yl)propyl)-4-(3-(6-methylbenzisoxazole))piperidine,
I-13 N-(3-(1H-benzotriazole-1-yl)propyl)-4-(3-(6-methoxybenzene and isoxazole))piperidine,
I-14 N-(3-(6-fluoro-1H-benzotriazole-1-yl)propyl)-4-(3-(6-fluorobenzo isoxazole))piperidine,
I-15 N-(3-(6-chloro-1H-benzotriazole-1-yl)propyl)-4-(3-(6-fluorobenzo isoxazole))piperidine,
I-16 N-(3-(6-methyl-1H-benzotriazole-1-yl)propyl)-4-(3-(6-fluorobenzo isoxazole))piperidine,
I-17 N-(3-(6-methoxy-1H-benzotriazole-1-yl)propyl)-4-(3-(6-fluorobenzo isoxazole))piperidine,
I-18 N-(3-(6-formyl-1H-benzotriazole-1-yl)propyl)-4-(3-(6-fluorobenzo isoxazole))piperidine,
I-19 N-(3-(6-methoxybenzotriazolyl)propyl)-4-(3-benzoisoxazole)piperidine
I-20 N-(2-(1-benzotriazole-yl)ethyl)-4-(3-(6-fluorobenzo isoxazole))piperidine,
I-21 N-(4-(1-benzotriazole)butyl)-4-(3-(6-fluorobenzo isoxazole))piperidine,
I-22 N-(4-(6-cyano-benzotriazole)butyl)-4-(3-(6-fluorobenzo isoxazole))piperidine,
I-22 N-(4-(6-cyano-benzotriazole)butyl)-4-(3-(6-fluorobenzo isoxazole))piperidine,
I-24 N-(2-(6-methoxybenzo triazole) ethoxy)-4-(3-benzoisoxazole)piperidine
I-25 N-(2-(1-benzotriazole) ethoxy)-4-(3-fluoro-benzisoxazole)piperidine
I-26 N-(3-(6-methoxybenzotriazolyl)propyl)-4-(3-(6-fluorophenyl and isothiazole))piperidine,
I-27 N-(3-(6-methoxybenzotriazolyl)propyl)-4-(3-(6-fluorobenzo pyrazol))piperidine,
I-28 N-(3-(6-methoxybenzotriazolyl)propyl)-4-(3-(6-furanfluorophenyl)))piperidine,
I-29 N-(4-(1H-benzimidazol-1-yl)butyl)-4-(2-furyl)piperidine,
I-30 N-(4-(1H-benzimidazol-1-yl)butyl)-4-(4-pyridyl)piperidine,
I-31 N-(4-(1H-benzimidazol-1-yl)butyl)-4-(2-pyrimidinyl) piperidine,
I-32 N-(4-(1H-benzotriazole-1-yl)butyl)-4-cyclohexyl piperidine,
I-33 N-(4-(1H-benzotriazole-1-yl)butyl)-4-(1-naphthyl)piperidine
I-34 N-(4-(1H-benzotriazole-1-yl)butyl)-4-(2-quinoxalinyl) piperidine
I-35 1-(4-(4-(3-chlorophenyl) piperazin-1-yl)butyl)-1H-benzimidazole,
I-36 1-(4-(4-(3-trifluoromethylphenyl) piperazin-1-yl)butyl)-1H-benzimidazole,
I-37 1-(4-(4-(2,3-dichlorophenyl) piperazin-1-yl)butyl)-1H-benzimidazole,
I-38 1-(4-(4-(2-methoxyphenyl) piperazin-1-yl)butyl)-1H-benzimidazole, I-39 2-methyl-1-(4-(4-(3-trifluoromethylphenyl) piperazin-1-yl)butyl)-1H-benzimidazole,
I-40 6-fluoro-1-(4-(4-(3-trifluoromethylphenyl) piperazin-1-yl)butyl)-1H-benzimidazole,
I-41 1-(3-(4-phenyl-piperazin-1-yl)propyl)-1H-benzimidazole,
I-42 1-(3-(4-(3-fluorophenyl) piperazin-1-yl)propyl)-1H-benzimidazole,
I-43 2-methyl-1-(3-(4-(3-fluorophenyl) piperazin-1-yl)propyl)-1H-benzimidazole,
I-44 1-(4-(4-(3-cyanophenyl) piperazin-1-yl)butyl)-1H-benzimidazole,
I-45 1-(4-(4-(4-methylphenyl) piperazin-1-yl)butyl)-1H-benzimidazole,
I-46 1-(4-(4-(2-furyl) piperazin-1-yl)butyl)-1H-benzimidazole,
I-47 1-(4-(4-(4-pyridyl) piperazin-1-yl)butyl)-1H-benzimidazole,
I-48 1-(4-(4-(2-pyrimidinyl) piperazin-1-yl)butyl)-1H-benzimidazole,
I-49 1-(4-(4-(1-cyclohexyl) piperazin-1-yl)butyl)-1H-benzimidazole,
I-50 1-(4-(4-(1-naphthyl) piperazin-1-yl)butyl)-1H-benzimidazole,
I-51 1-(4-(4-(2-quinoxalinyl) piperazin-1-yl)butyl)-1H-benzimidazole,
I-52 1-(4-(4-(3-(6-fluorobenzoisoxazolyl))piperazin-1-yl)butyl)-1H-benzimidazole,
I-53 1-(4-(4-(3-(6-fluorobenzothiazol isothiazolyl)) piperazin-1-yl)butyl)-1H-benzimidazole,
I-54 1-(4-(4-(3-benzopyrazolyl) piperazin-1-yl)butyl)-1H-benzimidazole,
I-55 1-(4-(4-(3-(6-fluorobenzofuranyl)) piperazin-1-yl)butyl)-1H-benzimidazole,
I-56 1-(4-(4-(3-(6-fluorobenzisoxazolyl)) piperazin-1-yl)propoxy)-1H-benzimidazole,
I-57 1-(4-(4-(3-trifluoromethylphenyl) piperazin-1-yl)propoxy)-1H-benzimidazole,
I-58 1-(4-(4-(3-chlorophenyl) piperazin-1-yl)propoxy)-1H-benzimidazole,
I-59 6-chloro-1-(4-(4-(3-trifluoromethylphenyl) piperazin-1-yl)butyl)-1H-benzimidazole,
I-60 6-cyano-1-(4-(4-(3-trifluoromethylphenyl) piperazin-1-yl)butyl)-1H-benzimidazole,
I-61 6-methoxycarbonyl-1-(4-(4-(3-trifluoromethylphenyl) piperazin-1-yl)butyl)-1H-benzimidazole,
I-62 2-chloro-1-(5-(4-(3-trifluoromethylphenyl) piperazin-1-yl) pentyl)-1H-benzimidazole,
I-63 1-(4-(4-(3-chlorophenyl) piperazin-1-yl)butyl)-1H-benzotriazole,
I-64 1-(4-(4-(3-fluorophenyl) piperazin-1-yl)butyl)-1H-benzotriazole,
I-65 1-(4-(4-(3-trifluoromethylphenyl) piperazin-1-yl)butyl)-1H-benzotriazole,
I-66 6-fluoro-1-(4-(4-(3-trifluoromethylphenyl) piperazin-1-yl)butyl)-1H-benzotriazole,
I-67 5,6-dimethyl-1-(4-(4-(3-trifluoromethylphenyl) piperazin-1-yl)butyl)-1H-benzotriazole,
I-68 3-(4-(4-(1H-benzotriazol-1-yl)butyl) piperazin-1-yl) benzisothiazole,
I-69 3-(4-(4-(1H-benzotriazol-1-yl)butyl) piperazine-1-yl) benzisoxazole,
I-70 6-fluoro-3-(4-(4-(1H-benzotriazol-1-yl)butyl) piperazin-1-yl)benzisoxazole,
I-71 6-fluoro-3-(4-(3-(1H-benzotriazol-1-yl) propyl) piperazin-1-yl)benzisoxazole,
I-72 1-(3-(4-(2,3-dichlorophenyl) piperazin-1-yl)propyl)-1H-benzotriazole,
I-73 1-(3-(4-(3-methylphenyl) piperazin-1-yl)propyl)-1H-benzotriazole,
I-74 1-(4-(4-(3-cyanophenyl) piperazin-1-yl)butyl)-1H-benzotriazole,
I-75 1-(5-(4-(3-trifluoromethylphenyl) piperazin-1-yl) pentyl)-1H-benzotriazole,
I-76 1-(4-(4-(2-furyl) piperazin-1-yl)butyl)-1H-benzotriazole,
I-77 1-(4-(4-(4-pyridyl) piperazin-1-yl)butyl)-1H-benzotriazole,
I-78 1-(4-(4-cyclohexyl-piperazin-1-yl)butyl)-1H-benzotriazole,
I-79 1-(4-(4-(1-naphthyl) piperazin-1-yl)butyl)-1H-benzotriazole,
I-80 1-(4-(4-(2-quinoxalinyl) piperazin-1-yl)butyl)-1H-benzotriazole,
I-81 1-(4-(4-(3-(6-fluoro-benzisothiazolyl)) piperazin-1-yl)butyl)-1H-benzotriazole,
I-82 1-(3-(4-(3-(6-fluoro-benzofuranyl) piperazin-1-yl)propyl)-1H-benzotriazole,
I-83 6-chloro-1-(4-(4-(3-trifluoromethylphenyl) piperazin-1-yl)butyl)-1H-benzotriazole,
I-84 6-cyano-1-(4-(4-(3-trifluoromethylphenyl) piperazin-1-yl)butyl)-1H-benzotriazole,
I-85 6-methoxycarbonyl-1-(4-(4-(3-trifluoromethylphenyl) piperazin-1-yl)butyl)-1H-benzotriazole,
I-86 1-(4-(4-(3-(6-fluoro-benzisoxazolyl) piperazin-1-yl) propoxy)-1H-benzotriazole,
I-87 6-fluoro-1-(4-(4-(3-(6-fluoro-benzisothiazolyl) piperazin-1-yl)propoxy)-1H-benzotriazole.

Chemical structures of the above compounds are shown in the following table:

| Code | Chemical structure |
|---|---|
| I-1 | 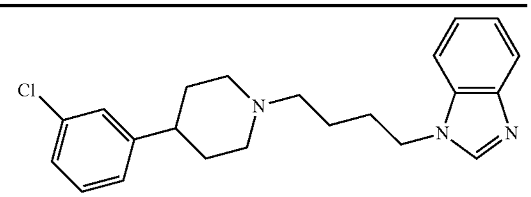 |
| I-2 | 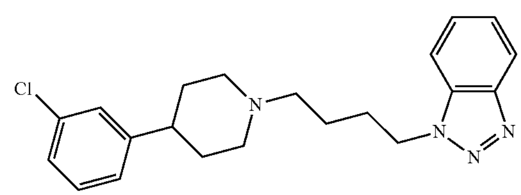 [SMILES: Clc1cccc(C2CCN(CCCCn3nnc4ccccc43)CC2)c1] |
| I-3 | 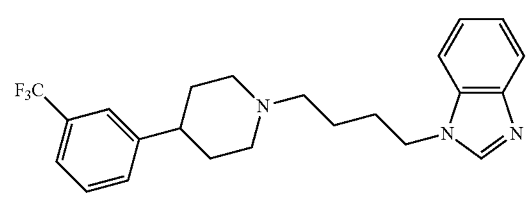 |
| I-4 | 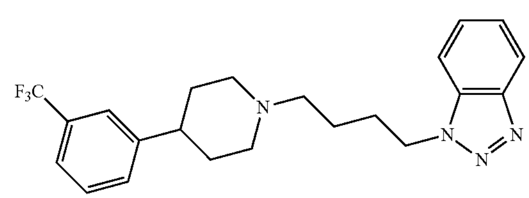 [SMILES: FC(F)(F)c1cccc(C2CCN(CCCCn3nnc4ccccc43)CC2)c1] |

| Code | Chemical structure |
|---|---|
| I-5 | 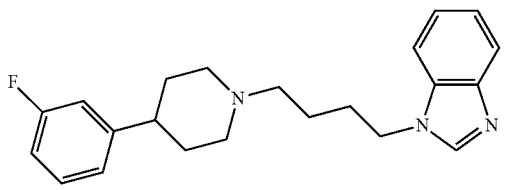 [SMILES: Fc1cccc(C2CCN(CCCCn3cnc4ccccc43)CC2)c1] |
| I-6 | 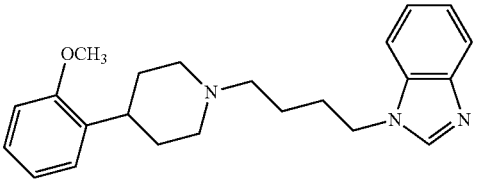 [SMILES: COc1ccccc1C1CCN(CCCCn2cnc3ccccc32)CC1] |
| I-7 | 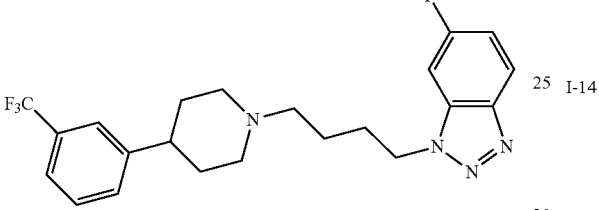 |
| I-8 | 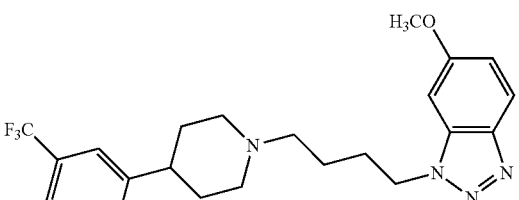 |
| I-9 | 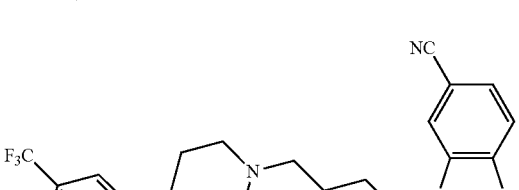 |
| I-10 | 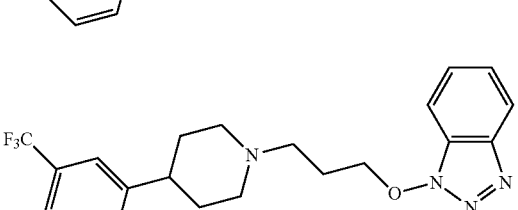 |
| I-11 | 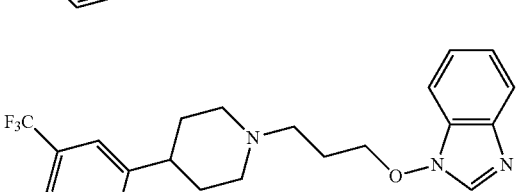 |
| Code | Chemical structure |
|---|---|
| I-12 | 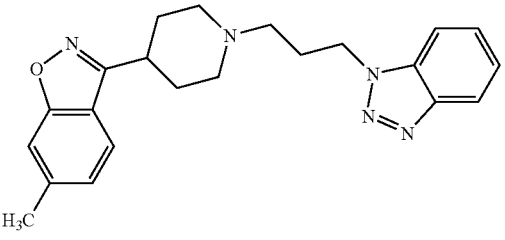 [SMILES: Cc1ccc2c(C3CCN(CCCn4nnc5ccccc54)CC3)noc2c1] |
| I-13 | 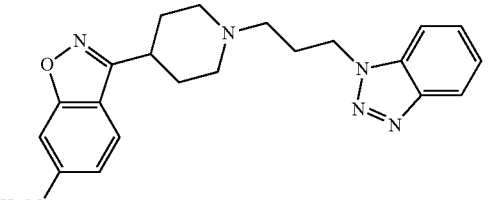 |
| I-14 | 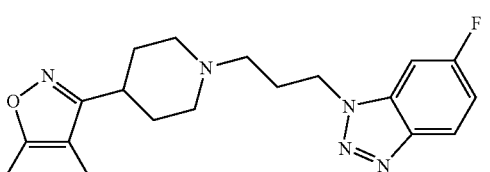 |
| I-15 | 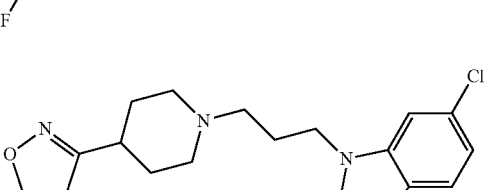 |
| I-16 | 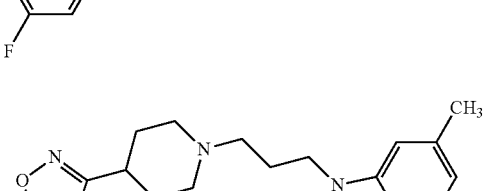 |
| I-17 | 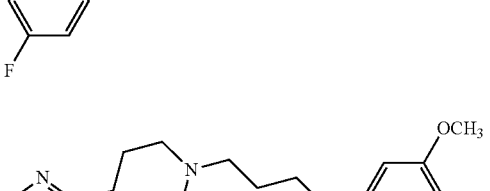 |

-continued

| Code | Chemical structure |
|---|---|
| I-18 | 6-fluoro-1,2-benzisoxazol-3-yl piperidine connected via propyl to benzotriazole with 6-CHO |
| I-19 | 1,2-benzisoxazol-3-yl piperidine connected via propyl to benzotriazole with 6-OCH₃ |
| I-20 | 6-fluoro-1,2-benzisoxazol-3-yl piperidine connected via ethyl to benzotriazole |
| I-21 | 6-fluoro-1,2-benzisoxazol-3-yl piperidine connected via butyl to benzotriazole |
| I-22 | 6-fluoro-1,2-benzisoxazol-3-yl piperidine connected via butyl to 6-CN-benzotriazole |
| I-23 | 6-methoxy-1,2-benzisoxazol-3-yl piperidine connected via butyl to 6-CN-benzotriazole |

-continued

| Code | Chemical structure |
|---|---|
| I-24 | 2,1-benzisoxazol-3-yl piperidine connected via ethoxy to 6-OCH₃-benzotriazole |
| I-25 | 2,1-benzisoxazol-3-yl piperidine connected via ethoxy to benzotriazole |
| I-26 | 6-fluoro-benzisothiazol-3-yl piperidine connected via propyl to 6-OCH₃-benzotriazole |
| I-27 | 6-fluoro-1H-indazol-3-yl piperidine connected via propyl to 6-OCH₃-benzotriazole |
| I-28 | 6-fluoro-1,2-benzisoxazol-3-yl piperidine connected via propyl to 6-OCH₃-benzotriazole |
| I-29 | 2-furyl piperidine connected via butyl to benzimidazole |

| Code | Chemical structure |
|------|-------------------|
| I-30 | 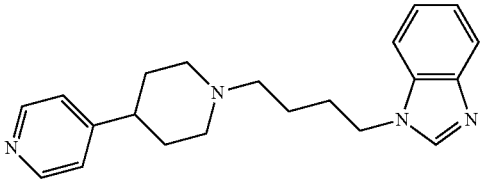 [SMILES: c1ccc2c(c1)ncn2CCCCN1CCC(c2ccncc2)CC1] |
| I-31 | 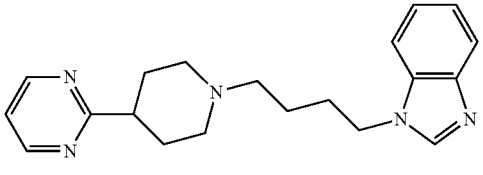 [SMILES: c1cnc(C2CCN(CCCCn3cnc4ccccc43)CC2)nc1] |
| I-32 | 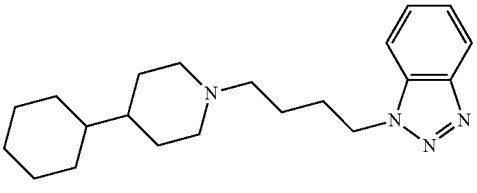 [SMILES: c1ccc2c(c1)nnn2CCCCN1CCC(C2CCCCC2)CC1] |
| I-33 | 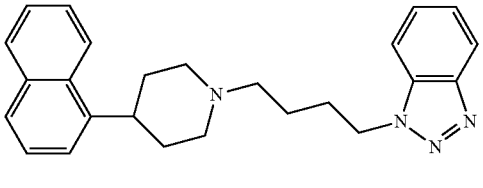 [SMILES: c1ccc2c(C3CCN(CCCCn4nnc5ccccc54)CC3)cccc2c1] |
| I-34 | 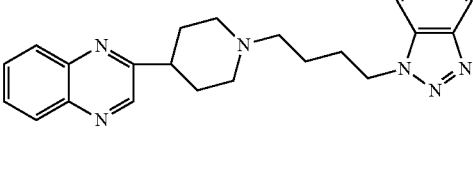 |
| I-35 | 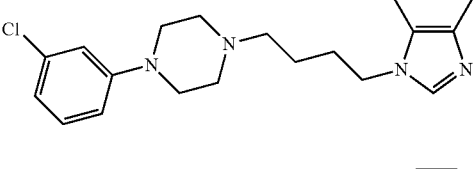 |
| I-36 | 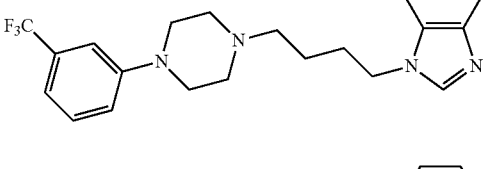 |
| I-37 | 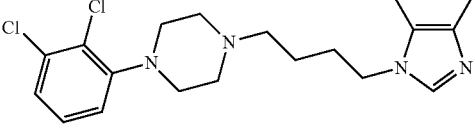 |
| I-38 | 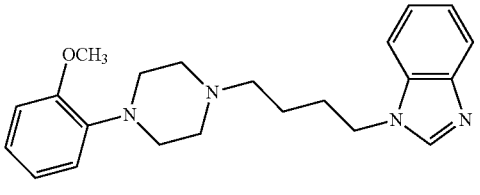 |
| I-39 | 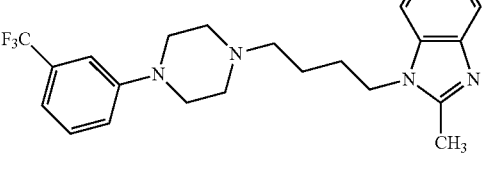 |
| I-40 | 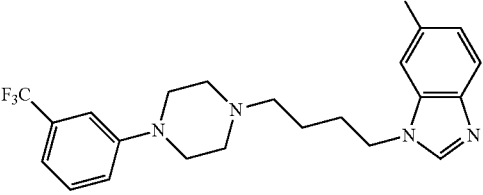 |
| I-41 | 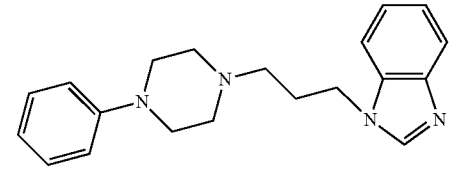 [SMILES: c1ccc(N2CCN(CCCn3cnc4ccccc43)CC2)cc1] |
| I-42 | 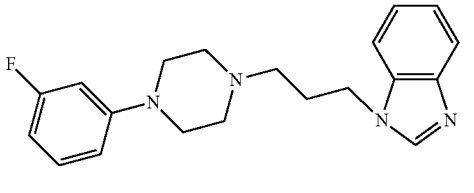 [SMILES: Fc1cccc(N2CCN(CCCn3cnc4ccccc43)CC2)c1] |
| I-43 | 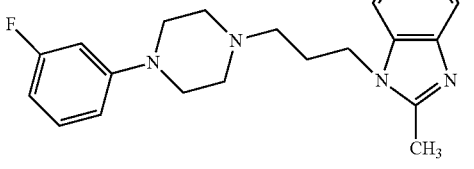 |
| I-44 | 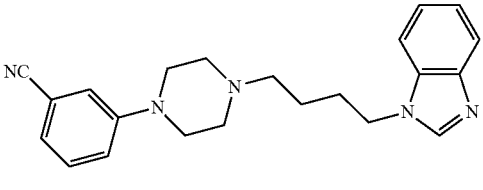 [SMILES: N#Cc1cccc(N2CCN(CCCCn3cnc4ccccc43)CC2)c1] |
| I-45 | 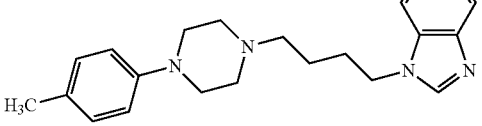 |

-continued

| Code | Chemical structure |
|------|-------------------|
| I-46 | (furan-2-yl)-piperazine-(CH₂)₄-benzimidazole |
| I-47 | (pyridin-4-yl)-piperazine-(CH₂)₄-benzimidazole |
| I-48 | (pyrimidin-2-yl)-piperazine-(CH₂)₄-benzimidazole |
| I-49 | cyclohexyl-piperazine-(CH₂)₄-benzimidazole |
| I-50 | (naphthalen-1-yl)-piperazine-(CH₂)₄-benzimidazole |
| I-51 | (quinoxalin-2-yl)-piperazine-(CH₂)₄-benzimidazole |
| I-52 | (6-fluorobenzo[d]isoxazol-3-yl)-piperazine-(CH₂)₄-benzimidazole |
| I-53 | (6-fluorobenzo[d]isothiazol-3-yl)-piperazine-(CH₂)₄-benzimidazole |

-continued

| Code | Chemical structure |
|------|-------------------|
| I-54 | (1H-indazol-3-yl)-piperazine-(CH₂)₄-benzimidazole |
| I-55 | (6-fluorobenzofuran-3-yl)-piperazine-(CH₂)₄-benzimidazole |
| I-56 | (6-fluorobenzo[d]isoxazol-3-yl)-piperazine-(CH₂)₃-O-benzimidazole |
| I-57 | (3-trifluoromethylphenyl)-piperazine-(CH₂)₃-O-benzimidazole |
| I-58 | (3-chlorophenyl)-piperazine-(CH₂)₃-O-benzimidazole |
| I-59 | (3-trifluoromethylphenyl)-piperazine-(CH₂)₄-(5-chloro-benzimidazole) |
| I-60 | (3-trifluoromethylphenyl)-piperazine-(CH₂)₄-(5-cyano-benzimidazole) |

| Code | Chemical structure |
|---|---|
| I-61 | 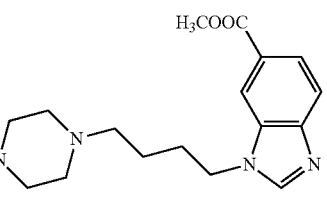 |
| I-62 | 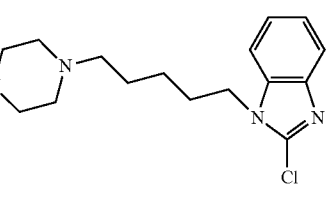 |
| I-63 | 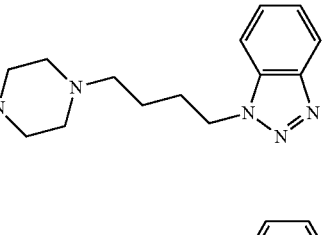 |
| I-64 | 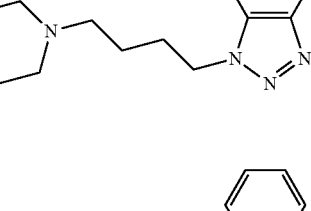 |
| I-65 | 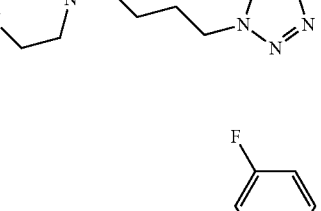 |
| I-66 | 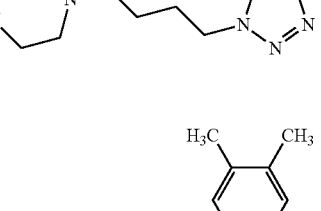 |
| I-67 | 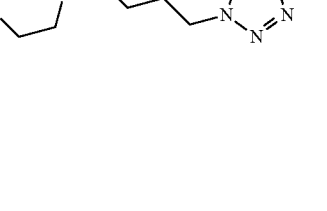 |
| I-68 | 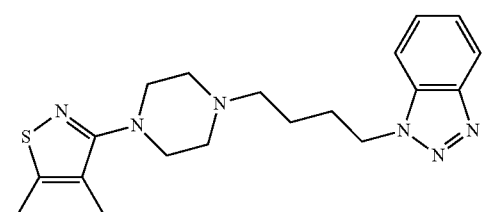 |
| I-69 | 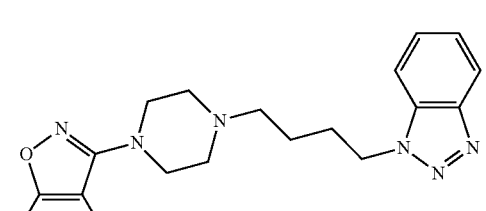 |
| I-70 | 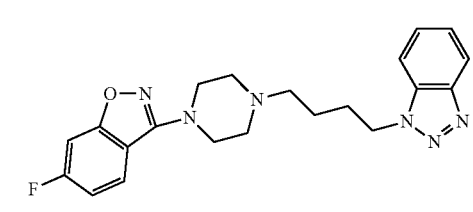 [SMILES: Fc1ccc2c(N3CCN(CCCCn4nnc5ccccc54)CC3)noc2c1] |
| I-71 | 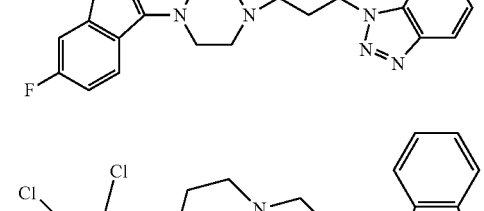 |
| I-72 | 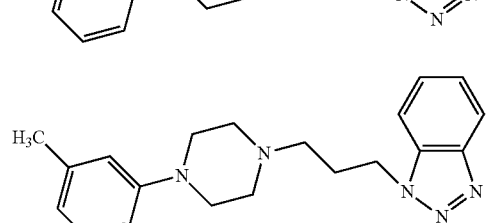 |
| I-73 | 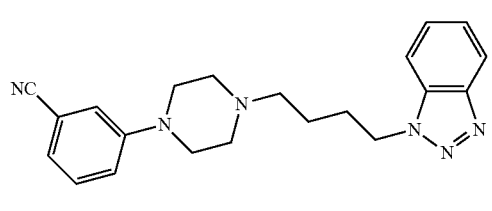 |
| I-74 | 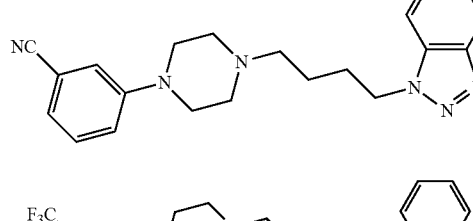 |
| I-75 | 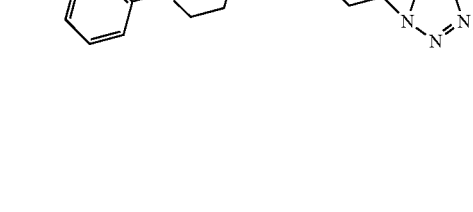 |

| Code | Chemical structure |
|---|---|
| I-76 | (2-furyl)-piperazine-butyl-benzotriazole |
| I-77 | (4-pyridyl)-piperazine-butyl-benzotriazole |
| I-78 | cyclohexyl-piperazine-butyl-benzotriazole |
| I-79 | (1-naphthyl)-piperazine-butyl-benzotriazole |
| I-80 | (2-quinoxalinyl)-piperazine-butyl-benzotriazole |
| I-81 | (6-fluoro-benzisothiazol-3-yl)-piperazine-butyl-benzotriazole |
| I-82 | (6-fluoro-benzofuran-3-yl)-piperazine-propyl-benzotriazole |
| I-83 | (3-trifluoromethylphenyl)-piperazine-butyl-(chloro-benzotriazole) |
| I-84 | (3-trifluoromethylphenyl)-piperazine-butyl-(cyano-benzotriazole) |
| I-85 | (3-trifluoromethylphenyl)-piperazine-butyl-(methoxycarbonyl-benzotriazole) |
| I-86 | (6-fluoro-benzisoxazol-3-yl)-piperazine-propoxy-benzotriazole |
| I-87 | (6-fluoro-benzisoxazol-3-yl)-piperazine-propoxy-(fluoro-benzotriazole) |

In a detailed embodiment of this invention, the following compound and its pharmaceutically acceptable salt are more preferred:

- I-1 N-(4-(1H-benzimidazol-1-yl)butyl)-4-(3-chlorophenyl)piperidine,
- I-2 N-(4-(1H-benzotriazole-1-yl)butyl)-4-(3-chlorophenyl)piperidine,
- I-3 N-(4-(1H-benzimidazol-1-yl)butyl)-4-(3-trifluoromethylphenyl)piperidine,
- I-4 N-(4-(1H-benzotriazole-1-yl)butyl)-4-(3-trifluoromethylphenyl)piperidine,
- I-7 N-(4-(6-fluoro-1H-benzotriazole-1-yl)butyl)-4-(3-trifluoromethylphenyl)piperidine,
- I-10 N-(4-(1H-benzotriazole-1-yl)propoxy)-4-(3-trifluoromethylphenyl)piperidine,
- I-11 N-(4-(1H-benzimidazol-1-yl)propoxy)-4-(3-trifluoromethylphenyl)piperidine,
- I-12 N-(3-(1H-benzotriazole-1-yl)propyl)-4-(3-(6-methylbenzisoxazole))piperidine,
- I-13 N-(3-(1H-benzotriazole-1-yl)propyl)-4-(3-(6-methoxybenzene and isoxazole))piperidine,
- I-14 N-(3-(6-fluoro-1H-benzotriazole-1-yl)propyl)-4-(3-(6-fluorobenzo isoxazole))piperidine,
- I-15 N-(3-(6-chloro-1H-benzotriazole-1-yl)propyl)-4-(3-(6-fluorobenzo isoxazole))piperidine,
- I-16 N-(3-(6-methyl-1H-benzotriazole-1-yl)propyl)-4-(3-(6-fluorobenzo isoxazole))piperidine,
- I-17 N-(3-(6-methoxy-1H-benzotriazole-1-yl)propyl)-4-(3-(6-fluorobenzo isoxazole))piperidine,
- I-18 N-(3-(6-formyl-1H-benzotriazole-1-yl)propyl)-4-(3-(6-fluorobenzo isoxazole))piperidine, I-19 N-(3-(6-methoxybenzotriazolyl)propyl)-4-(3-benzoisoxazole)piperidine
I-20 N-(2-(1-benzotriazole-yl)ethyl)-4-(3-(6-fluorobenzo isoxazole))piperidine,
I-21 N-(4-(1-benzotriazole)butyl)-4-(3-(6-fluorobenzo isoxazole))piperidine,
I-22 N-(4-(6-cyano-benzotriazole)butyl)-4-(3-(6-fluorobenzo isoxazole))piperidine,
I-22 N-(4-(6-cyano-benzotriazole)butyl)-4-(3-(6-fluorobenzo isoxazole))piperidine,
I-35 1-(4-(4-(3-chlorophenyl) piperazin-1-yl)butyl)-1H-benzimidazole,
I-36 1-(4-(4-(3-trifluoromethylphenyl) piperazin-1-yl)butyl)-1H-benzimidazole,
I-37 1-(4-(4-(2,3-dichlorophenyl) piperazin-1-yl)butyl)-1H-benzimidazole,
I-63 1-(4-(4-(3-chlorophenyl) piperazin-1-yl)butyl)-1H-benzotriazole,
I-64 1-(4-(4-(3-fluorophenyl) piperazin-1-yl)butyl)-1H-benzotriazole,
I-65 1-(4-(4-(3-trifluoromethylphenyl) piperazin-1-yl)butyl)-1H-benzotriazole,
I-66 6-fluoro-1-(4-(4-(3-trifluoromethylphenyl) piperazin-1-yl)butyl)-1H-benzotriazole,
I-68 3-(4-(4-(1H-benzotriazol-1-yl)butyl) piperazin-1-yl)benzisothiazole,
I-70 6-fluoro-3-(4-(4-(1H-benzotriazol-1-yl)butyl) piperazin-1-yl)benzisoxazole,
I-71 6-fluoro-3-(4-(3-(1H-benzotriazol-1-yl) propyl) piperazin-1-yl)benzisoxazole,
I-72 1-(3-(4-(2,3-dichlorophenyl) piperazin-1-yl)propyl)-1H-benzotriazole,
I-73 1-(3-(4-(3-methylphenyl) piperazin-1-yl)propyl)-1H-benzotriazole,
I-83 6-Cl-1-(4-(4-(3-trifluoromethylphenyl) piperazin-1-yl)butyl)-1H-benzotriazole, In a detailed process of this invention, the following compound and its pharmaceutically acceptable salt are particularly preferred:
I-3 N-(4-(1H-benzimidazol-1-yl)butyl)-4-(3-trifluoromethylphenyl)piperidine,
I-4 N-(4-(1H-benzotriazole-1-yl)butyl)-4-(3-trifluoromethylphenyl)piperidine,
I-19 N-(3-(6-methoxybenzotriazolyl)propyl)-4-(3-benzoisoxazole)piperidine
I-36 1-(4-(4-(3-trifluoromethylphenyl) piperazin-1-yl)butyl)-1H-benzimidazole,
I-37 1-(4-(4-(2,3-dichlorophenyl) piperazin-1-yl)butyl)-1H-benzimidazole,
I-63 1-(4-(4-(3-chlorophenyl) piperazin-1-yl)butyl)-1H-benzotriazole,
I-65 1-(4-(4-(3-trifluoromethylphenyl) piperazin-1-yl)butyl)-1H-benzotriazole,
I-68 3-(4-(4-(1H-benzotriazol-1-yl)butyl) piperazin-1-yl)benzisothiazole, For formula (I) in this invention, following pharmaceutically acceptable salts are more preferred: hydrochloride salt, hydrobromide salt, sulfate salt, trifluoroacetate salt, methanesulfonate salt, tartrate salt, malate salt, succinate salt, maleate salt, citrate salt, phosphate salt, lactate salt, pyruvate salt, acetate salt, fumarate salt, oxaloacetate salt, ethanesulfonate salt, oxalate salt, besylate salt or hydroxyalkyl ethanesulfonate salt. In this invention, the pharmaceutically acceptable salts are more preferred to contain crystal water molecules, and more preferably, 0.5-3 molecules.

Of the above, even more preferred salts are hydrochloride salt, hydrobromide salt, sulfate salt or methanesulfonic acid salt.

The most preferred salt is hydrochloride salt; for compound I-36, I-37, I-63, I-65 and I-68, more preferred salt are hydrochloride salt compounds, including II-36, II-37, II-63, II-65 and II-68:

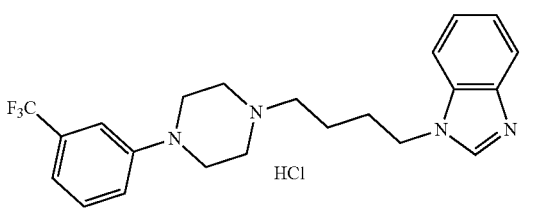
(II-36)

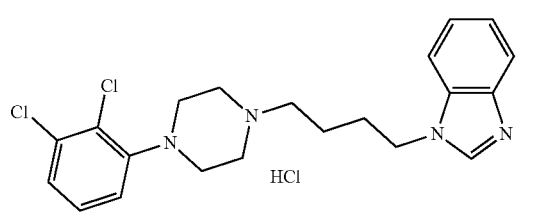
(II-37)

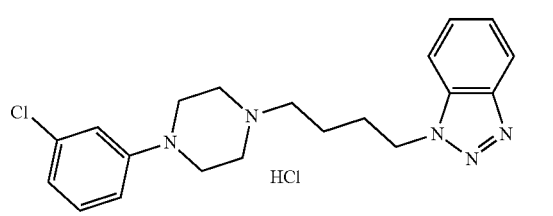
(II-63)

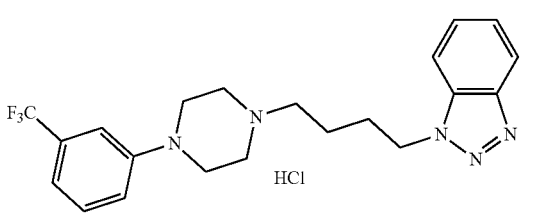
(II-65)

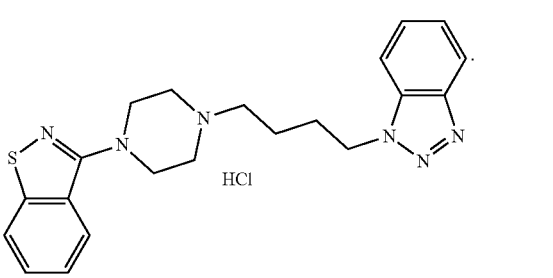
(II-68)

Formula (I) of the present invention and pharmaceutically acceptable salts have a significant vasodilating effect. Preferably, they can block at least one of the following: $\alpha_1$ receptors, $Ca^{2+}$ channel and $5-HT_{2A}$ receptors. This compound acts on multi-channels and through different routes in parallel, demonstrating double or triple vasodilating effect via more than one of the following: $\alpha_1$ receptors, $Ca^{2+}$ channel and 5-HT receptors. Even more preferably, this compound acts on three targets, demonstrating triple vasodilating effect via blocking $\alpha_1$ receptors, $Ca^{2+}$ channel and $5\text{-HT}_{2A}$ receptors. Thus, if impartial block on a1 receptors, it also blocks $Ca^{2+}$ and protects against myocardial hypertrophy, protects endothelial cells, fights against atherosclerosis, inhibits vascular smooth muscle proliferation or improves cerebral circulation; and/or it blocks $Ca^{2+}$ channel of sinus node and slows down heart rate, effectively prevents tachycardia and palpitations, thereby preventing first-dose effect; and due to the triple effects, the remaining a1 receptors still contribute to pressor reflex, preventing orthostatic hypotension; at the same time, blocking on $5\text{-HT}_{2A}$ receptors helps treating heart failure and improves blood supply of patients with obstructive vascular disease, thus it can be used to treat hypertensions patients with heart failure, atherosclerosis, endothelial damage, and patients with advanced hypertension or certain refractory hypertension.

Compared with existing clinical antihypertensive drugs, the compound of formula (I) and its pharmaceutically acceptable salt have enhanced hypotensive activity, better tolerability and/or increased safety.

For this compound of formula (I) and its pharmaceutically acceptable salts, this invention also relates to their use in the preparation of vasodilator drugs, in particular, for preventing, alleviating or treating diseases or symptoms related to pathological contraction or vasospasm, such as high blood pressure, heart failure, angina, coronary heart disease etc., and also vasospasm caused by a cerebral ischemic diseases, ischemic diseases, shock, and also renal ischemia, renal dysfunction and spastic peripheral vascular disease (such as Buerger, Raynaud's disease, etc.).

Subjects herein is preferably a mammal, particularly preferably human.

This invention also relates to a pharmaceutical combination comprising compound of formula (I) and it pharmaceutically acceptable salt for oral, parenteral, inhalation spray, rectal, intranasal, sublingual, buccal, transdermal administration, or administration via implants; the parenteral administration includes subcutaneous, intradermal, intravenous, intramuscular, intra-articular, intrasynovial, intrasternal, intrathecal, intralesional and intracranial injection or infusion. This compound of formula (I) or its pharmaceutically acceptable salt is preferably administered orally, sublingually, intravenously, intramuscularly or subcutaneously. The pharmaceutical combination according to the invention may contain one or more pharmaceutical carriers, additives or mediums, including but not limited to, diluents and excipients such as water etc.; binders such as cellulose derivatives, gelatin, polyvinyl pyrrolidone, etc.; fillers such as starch etc., disintegrants such as calcium carbonate, sodium hydrogencarbonate; lubricant such as magnesium stearate, calcium stearate etc.; and other additives such as flavors and sweeteners.

The pharmaceutical combination according to the invention may be in the form of sterile injection (including sterile aqueous or oil suspensions) comprising the compound of formula (I) and it pharmaceutically acceptable salt. The suspension may be prepared using suitable dispersant or wetting agents (e.g., Tween 80) and suspending agent according to techniques known in the art. The sterile injectable preparation may also be a sterile injectable solution or suspension in a non-toxic parenterally-acceptable diluent or solvent, such as a solution in 1,3-butanediol. Suitable diluents include, for example, water, Ringer's solution and isotonic sodium chloride solution. In addition, sterile fixed oils may be employed conventionally as a solvent or suspending medium. For this purpose, any bland fixed oil may be employed including synthetic mono or diglycerides. In addition, fatty acids such as oleic acid and its glyceride derivatives may likewise be used in the preparation of injectable preparations, and other natural oils for pharmaceutical use may be used in the preparation, such as olive oil or castor oil, especially when they are polyoxyethylated. The oil solution or suspension may contain long chain alcohol or similar alcohol as diluents or dispersant (Including those described in Ph. Helv).

In the invention, the pharmaceutical combination of the compound formula (I) or its pharmaceutically acceptable salts, may be administered orally in any dosage forms, including, but not limited to, capsules, tablets, powders, granules, and aqueous suspensions and solutions. The dosage forms may be prepared with techniques know in the art. Tablets for oral administration may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening and/or flavoring and/or coloring agents In the invention, the compound of formula (I) and its pharmaceutically acceptable salt may also be administered rectally in the form of aerosols or inhalers. Such compositions of the invention may be prepared with known technique of the pharmaceutical field, and may contain benzyl alcohol or other appropriate preservatives, absorption enhancers improving bioavailability, fluorocarbons, and/or other solubilizing or dispersing agents known in the art, and prepare in saline solution.

The compounds of this invention may also be administered rectally in the form of suppositories. These combinations can be prepared by mixing the drug with a suitable non-irritating excipient which is solid at room temperature, but liquid at rectal temperature and, therefore, will melt in the rectum to release the drug. Such materials include cocoa butter, beeswax and polyethylene glycols.

According to studies performed in anesthetized rats, the compounds in the invention has a lower daily dose than amlodipine. Daily dose of amlodipine (e.g. 10 mg/day) are known in the art for relaxation of vascular or treat hypertension. The suitable dosage of the compound formula (I) may be determined by physicians based on clinical study results and patient condition and age.

The compositions in the invention should be formulated using common methods in the medical art, and 0.1 wt %-99.5 wt % of the formulation should be active substances, depending upon the particular disease to be treated or prevented or the condition of the patients to receive the composition. The dosage of the composition can be easily determined by technician of the art using contents described in this patent.

In another detailed embodiment, the compounds of the invention can be used in combination with one or more other active substances. The compound or its pharmaceutically acceptable salts may be formulated with one or more active substances used as monotherapy, or, they may be used in combination with two or more independent compositions, wherein the compound of the invention is formulated in one composition while other active substances are formulated in one or more compositions. The compounds of the invention may be used in combination with other drugs to prevent, allievate or treat diseases or symptoms related to sustained pathologic vascular contraction or spasm; other drugs include other anti-smooth muscle spasm drugs, preferably selected from sertraline, captopril, benazepril, valsartan, propranolol and diuretics.

In another aspect, the invention also related to the methods for preparing the compound of formula (I):

Method (I)

Wherein

Under 10-150° C., compound

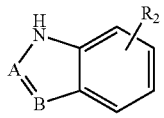 and compound 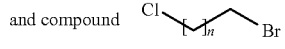

are reacted in reagent in the presence of an inorganic base and a phase transfer catalyst, and result in compound

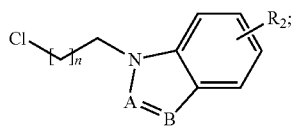

and then after reflux, the resulted compound react with

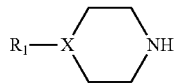

and react in reagent in the presence of an inorganic base and, and result in compound

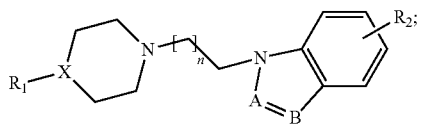

or

Method (II)

Wherein

Under 10-150° C., compound

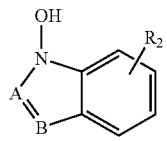 and compound 

are reacted in reagent in the presence of an inorganic base and a phase transfer catalyst, and result in compound

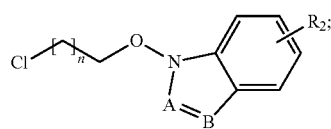

and then after reflux, the resulted compound react with

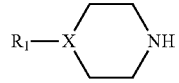

and react in reagent in the presence of an inorganic base and, and result in compound

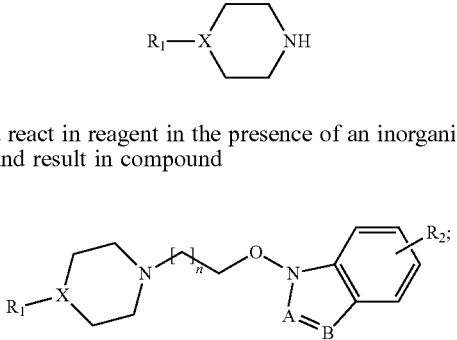

wherein, $R_1$ represents aromatic group or aliphatic cyclic group mono- or poly-substituted with $R_3$, The aromatic group is a benzo five-membered ring or six-membered heterocyclic ring, preferably selected from a phenyl group, a naphthyl group, and a hetero atom selected from N, S, O, or it is a five- or six-membered unsaturated heterocyclic ring; more preferably, phenyl, naphthyl, benzothiazolyl, benzisothiazolyl, benzoxazolyl, benzisoxazolyl, benzimidazolyl, benzo-pyrazolyl, benzofuranyl, benzo-pyrimidinyl, benzo-pyridyl, quinoxaline, furanyl, pyridyl or pyrimidinyl; still more preferably, a phenyl group, benzisoxazolyl, benzisothiazole, benzo-pyrazolyl, benzofuryl, naphthyl, furanyl, pyridyl, pyrimidinyl or quinoxaline group; and preferably phenyl, pyridyl, benzofuranyl, benzisothiazolyl, benzisoxazolyl or quinoxaline group; particularly preferably phenyl, benzisoxazolyl or benzisothiazole; preferably, A is N when the aromatic group is benzisoxazolyl or benzisothiazole time;

The aliphatic cyclic group described is preferably a five- or six-membered saturated cyclic hydrocarbon group, or a five- or six-membered saturated heterocyclic group with hetero atoms selected from N, S and O; more preferably, a cyclopentyl, cyclohexyl, tetrahydrofuranyl, piperidinyl or piperazinyl group; still more preferably, cyclohexyl, piperidyl or piperazinyl group; and particularly preferably, a cyclohexyl group;

$R_3$ is H, halogen, CN, $C_1$-$C_6$ alkyl, $C_1$-$C_6$ alkoxy, CHO, CO($C_1$-$C_6$ alkyl), COO($C_1$-$C_6$ alkyl), COOH, $NO_2$, $NH_2$, NH(C1-$C_6$ alkyl), N($C_1$-$C_6$ alkyl)$_2$, SH, S($C_1$-$C_6$ alkyl), —S(O) ($C_1$-$C_6$ alkyl), —S(O)$_2$H, or —S(O)$_2$ ($C_1$-$C_6$ alkyl), and the alkyl of the above groups is optionally substituted with one or more halogen atoms; preferably, $R_3$ is H, halogen, CN, $C_1$-$C_6$ alkyl, $C_1$-$C_6$ alkyl alkoxy, CHO, CO($C_1$-$C_6$ alkyl), COO($C_1$-$C_6$ alkyl) or COOH, the alkyl of the above groups optionally substituted with one or more (e.g., one to three) halogen atoms; more preferably, $R_3$ is H, F, Cl, Br, CN, and the alkyl is optionally $C_1$-$C_6$ alkyl or $C_1$-$C_6$ alkoxy substituted with 1 to 3 halogen atoms, CHO, $COCH_3$ or $COOCH_3$; still preferably, $R_3$ is H, F, Cl, $COCH_3$, alkyl, a $C_1$-$C_4$ alkyl or $C_1$-$C_4$ alkoxy group optionally substituted with 1-3 halogen atoms; even more preferably, $R_3$ is H, F, Cl, CN, $CF_3$, $CH_3$, $OCH_3$ or $COCH_3$; when $R_3$ are poly-substituent groups, $R_3$ are independently selected from the group described above;

A, B and X represent CH or N independently; preferably, A and B represent N;

$R_2$ is H, halogen, CN, $C_1$-$C_6$ alkyl, $C_1$-$C_6$ alkoxy, CHO, CO($C_1$-$C_6$ alkyl), COO($C_1$-$C_6$ alkyl), COOH, $NO_2$, $NH_2$, NH(C1-$C_6$ alkyl), N($C_1$-$C_6$alkyl)$_2$, SH, S($C_1$-$C_6$ alkyl), —S(O) ($C_1$-$C_6$ alkyl), —S(O)$_2$H, or —S(O)$_2$($C_1$-$C_6$ alkyl), and the alkyl of the above groups is optionally substituted with one or more halogen atoms; preferably, $R_2$ is H, halogen, CN, $C_1$-$C_6$ alkyl, $C_1$-$C_6$ alkyl alkoxy, CHO, CO($C_1$-$C_6$ alkyl), COO($C_1$-$C_6$ alkyl) or COOH, and the alkyl of the above groups are optionally substituted with one or more (e.g., one to three) halogen atoms; more preferably, $R_2$ is H, F, Cl, Br, CN, and the alkyl is optionally $C_1$-$C_6$ alkyl or $C_1$-$C_6$ alkoxy substituted with 1 to 3 halogen atoms, CHO, COCH$_3$ or COOCH$_3$; still preferably, $R_2$ is H, F, Cl, COCH$_3$, alkyl, a $C_1$-$C_4$ alkyl or $C_1$-$C_4$ alkoxy group optionally substituted with 1-3 halogen atoms; even more preferably, $R_2$ is H, F, Cl, CN, CF$_3$, CH$_3$, OCH$_3$ or COCH$_3$; when $R_2$ are poly-substituent groups, they are independently selected from the groups described above;

Optionally, Y represents saturated or unsaturated, straight or branched hydrocarbon chain (with 1 to 8 carbon atoms) substituted with one or more (e.g., 1 to 3) halogen atoms substituted, in which one or more carbon is optionally substituted with hetero-atoms including oxygen, sulfur, and nitrogen; preferably, Y is unsubstituted saturated 1-8 carbon hydrocarbon group or 1-8 carbon saturated hydrocarbon group where one carbon atom is replaced by oxygen or sulfur, e.g., —$C_{1-7}$ alkylene-O—; Y is more preferably a methylene, ethylene, propylene, butylene, pentylene, hexylene, heptylene, octadienyl, oxymethylene, oxyethylene, oxypropylene, oxyalkylene group, oxyalkylene pentyl, hexyl, oxyalkylene, oxyalkylene heptyl group, methylene group, ethylene group, propylene group, butylene group, pentylene group, hexylene group or an alkylene group, heptyl group; still more preferably, Y is methylene, ethylene, propylene, butylene, pentylene, hexylene, heptylene, octylene, methylene group, ethylene group, propylene group, butylene group, pentylene group, hexylene alkylene group or heptyl group; and particularly preferably ethylene, propylene, butylene, ethyleneoxy or propyleneoxy; most preferably propylene or butylene.

In method (I) and (II), the first steps of the reactions are completed in solvents with the existence of inorganic base and a phase transfer catalyst, respectively; the inorganic base is preferably selected from sodium hydride, sodium hydroxide, sodium methoxide, sodium ethoxide, sodium carbonate, sodium hydrogencarbonate, potassium hydride, potassium hydroxide, potassium methoxide, potassium ethoxide, potassium carbonate or potassium bicarbonate, and more preferably selected from sodium hydride or sodium hydroxide; the phase transfer catalyst is preferably selected from tetrabutylammonium bromide, tetrabutylammonium chloride, tetrabutyl ammonium hydrogen sulfate or 1,4,7,10,13,16-hexaoxacyclooctadecane alkyl (i.e. 18-Crown-6), and more preferably tetrabutylammonium bromide; the solvents used in first step are common solvents used in the art, and is preferably selected from water (except when sodium hydride is used), N-methylpyrrolidone (NMP) or N, N-dimethylformamide (DMF) and mixtures; reaction temperature of the first step is 10-150° C., and preferably 15-130° C., and more preferably 20-100° C., and most preferably 30-100° C.; reaction time may be determined by technicians in the art, and may be 0.5-20 hours, preferably 1-15 hours;

In method (I) and (II), the second steps of the reactions are completed in solvents with the existence of organic base and potassium iodide; the organic base is preferably selected from diisopropylethylamine, diethylamine, triethylamine, pyridine, t-butylamine, cyclopropylamine, di-n-butylamine, diisopropylamine, or 1,2-dimethyl-propylamine, and more preferably diisopropylethyl amine; second-stage reaction use common solvent in the art, preferably acetonitrile, DMF, dimethylsulfoxide (DMSO) or methyl ethyl ketone, and mixtures; reaction time may be determined according to the experience of the skilled technician, for example 1-30 hours, preferably 5-25 hours;

The invention preferably include a process to prepare the pharmaceutically acceptable salt using the compound to react with acid. The acids may be hydrochloric acid, hydrobromic acid, sulfuric acid, methanesulfonic acid, trifluoroacetic acid, tartaric acid, malic acid, succinic acid, maleic acid, citric acid, phosphoric acid, lactic acid, pyruvic acid, acetic acid, fumaric acid, oxaloacetate, ethanesulfonamide acid, oxalic acid or isethionic, more preferably hydrochloric acid, hydrobromic acid, sulfuric acid or methane sulfonic acid, and most preferably hydrochloric acid;

The salt preparation step is preferably carried out in a solvent, and the solvent used may be methanol, ethanol, propanol, methyl acetate, ethyl, acetone, methyl ethyl ketone, methyl isopropyl ketone, methyl isobutyl ketone, acetonitrile, propionitrile, dimethyl formamide, dimethyl acetamide, N-methylpyrrolidone, dimethyl sulfoxide or tetramethylene sulfone etc., preferably ethyl acetate and/or ethanol.

Every embodiment or embodiments of different priority levels may be combined in any suitable manner unless otherwise specified.

The compounds of the invention may be prepared as follows:

Example 1

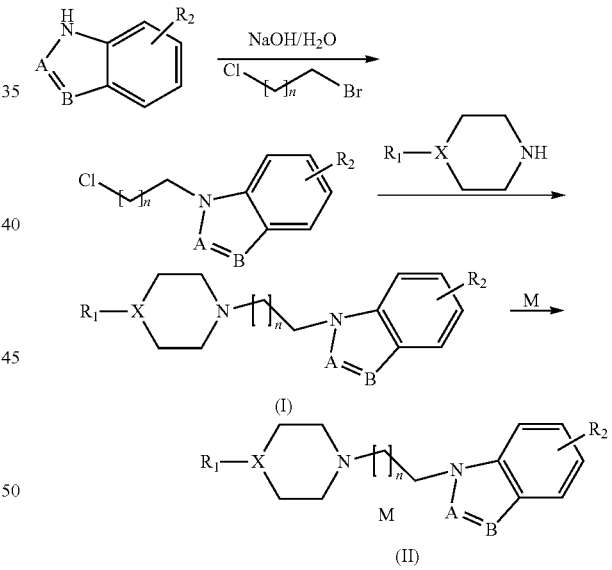

Wherein $R_1$, $R_2$, A, B and X are defined as above; n=0-7; M represents pharmaceutically acceptable salts, including HCl, HBr, H$_2$SO$_4$, CH$_3$SO$_3$H etc.

N-chloroalkyl-benzo five-membered heterocyclic compounds is prepared via a condensation reaction between a substituted benzo five-membered nitrogen heterocyclic compound and chlorinated alkyl bromide in a NaOH solution, which is then used to prepare compound of formula (I) via a condensation reaction with 4-substituted piperidine or piperazine. The compound of the invention may react with acid to prepare its salts. The route described in example 1 may be used to prepare compound I-1 to I-9, I-12 to I-23, I-26 to I-55, I-59 to I-85, and their salts.

Example 2

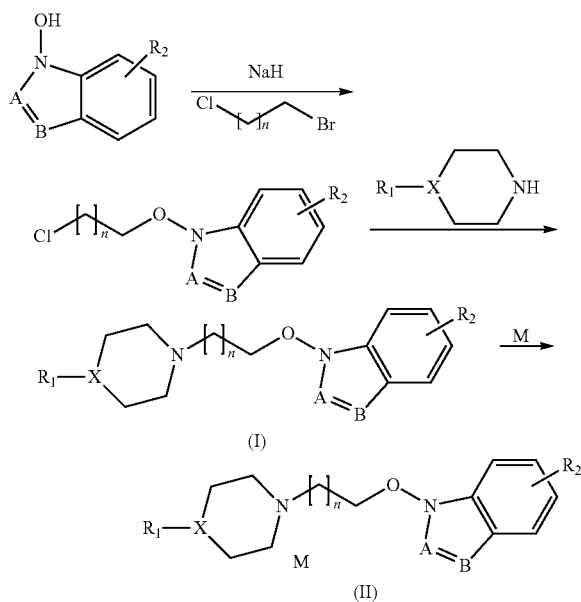

Wherein $R_1$, $R_2$, A, B and X are defined as above; n=0-7; M represents pharmaceutically acceptable salts, including HCl, HBr, $H_2SO_4$, $CH_3SO_3H$ etc.

The compound of formula (I) may be prepared via a condensation reaction between 4-substituted piperidine or piperazine and a chloride compound which is prepared via reaction between chlorinated alkyl bromide and a sodium compound; the sodium compound may be prepared via reaction between benzo five-membered heterocyclic-1 alcohol and NaH. The compound of the invention may react with any selected acid to prepare its salts. The route described in example 1 may be used to prepare compound I-10 to I-11, I-24 to I-25, I-56 to I-557, I-86 to I-87, and their salts.

General Synthetic Process I: Preparation of N-(3-Chloropropyl)-Substituted Benzo Five-Membered Heterocyclic Compound Dissolve 1H-substituted benzo five-membered heterocyclic compound (0.10 mol) in 100 mL of 30 wt % NaOH solution, add 3-chloro-bromopropane (31.4 g, 0.10 mol) and tetrabutylammonium bromide (0.8 g), and mix thoroughly for 5 minutes. Heat slowly to 60° C. and allow to react for 2 hours under stirring. The reaction solution was cooled to room temperature, and extracted with 100 mL of dichloromethane and the liquid was separated; and 100 mL of dichloromethane was then added to aqueous phase, and then the organic phases were combined and washed with 100 mL of saturated saline solution and the liquid was separated; and the organic phase was evaporated to obtain oily substance. The oily substance was then purified by chromatography separation using neutral $Al_2O_3$ or separated and purified by preparative HPLC to obtain N-(3-chloropropyl)-substituted benzo five-membered heterocyclic compound, with a yield of 30.0-85.0%.

General Synthetic Process II: Preparation of N-(3-(Benzo-Substituted Five-Membered Nitrogen Heterocycle) Propyl)-4-Substituted Piperidine Dissolve N-(3-chloropropyl)-substituted benzo five-membered heterocyclic compound (0.06 mol) in 150 ml of acetonitrile, add 4-substituted piperidine (0.05 mol), diisopropylethyl amine (0.2 mol) and potassium iodide (0.05 mol), and stirred for 10 minutes at room temperature, then heat and reflux for $10^{-2}0$ hours. The solution was then cooled to room temperature, filtered, and the filtrate then concentrated to obtain an oily substance which is purified by chromatographic separation using neutral $Al_2O_3$, and then eluted with dichloromethane/methanol mixture to obtain the compound of formula (I), with a yield of 65.0-72.0%.

General Synthetic Process III: Preparation of N-(2-Chloroethoxy)-Substituted Benzo Five-Membered Heterocyclic Compounds N-hydroxybenzotriazole five-membered heterocyclic compounds (0.1 mol) was dissolved in 10 mL of NMP, and a mixture containing 50% wt sodium hydride and solid wax was added in portions. At the same time, dissolve 3-chloro-bromopropane (0.015 mol) in 5 ml of NMP, and add the solution in the mixture solution above, and allow to react under room temperature for 12 hours under stirring. The reaction solution is then poured into 50 ml of water and extracted with ethyl acetate (3×50 mL); then the organic phases are combined and washed with 30 mL of water; Anhydrous magnesium sulfate was then used to dry the organic phase, which was then filtered and evaporated to dryness; the oily substance obtained was then purified by chromatography using neutral $Al_2O_3$ or separated and purified by preparative HPLC to obtain 1-(2-chloroethoxy)-substituted heterocyclic benzo five-membered compound with a yield of 75.0-85.0%.

General Synthetic Process IV: Preparation of 1-(4-Chlorobutyl)-1H-Substituted-Benzimidazole The substituted 1H-benzimidazol (0.10 mol) was dissolved in 200 mL of 20 wt % sodium hydroxide aqueous solution and then was added with 4-chloro-bromobutane (34.3 g, 0.20 mol), tetrabutylammonium bromide (1.0 g); it is then mixed for 5 minutes and slowly warmed to 60° C. and react for 2 hours under stirring. The reaction solution was cooled to room temperature, and extracted with 100 mL of dichloromethane and the liquid was separated; and 100 mL of dichloromethane was then added to aqueous phase, and then the organic phases were combined and washed with 100 mL of saturated saline solution and the liquid was separated; and the organic phase was evaporated to obtain oily substance. The oily substance was then purified by chromatography separation using neutral Al2O3 or separated and purified by preparative HPLC to obtain 1-(4-chlorobutyl)-1H-substituted-benzimidazole, with a yield of 30.0-65.0%.

General Synthetic Process V: Preparation of 1-(4-(4-(substituted phenyl)piperazin-1-yl)butyl)-1H-substituted-benzimidazole 1-(4-chlorobutyl)-1H-substituted-benzimidazole (0.036 mol) was dissolved in 100 ml of acetonitrile and added with a substituted phenyl piperazine (0.03 mol), diisopropyl ethylamine (15.5 g, 0.12 mol), and potassium iodide (5.0 g, 0.03 mol), and then stirred for 10 minutes at room temperature, and allow to react for 10-20 hours under heating and reflux. The solution was then cooled to room temperature, filtered, and the filtrate then concentrated to obtain an oily substance which is purified by chromatographic separation using neutral Al2O3, and then eluted with dichloromethane/ methanol mixture to obtain the compound as described above, with a yield of 60.0-72.0%.

General Synthetic Process VI: Preparation of 1-(4-Chlorobutyl)-1H-Substituted Benzotriazole The substituted 1H-benzotriazole (0.10 mol) was dissolved in 100 mL of 30 wt % sodium hydroxide aqueous solution and then was added with 4-chloro-bromobutane (34.3 g, 0.20 mol), tetrabutylammonium bromide (0.8 g, 0.0025 mol); it is then mixed and stirred for 5 minutes Heat slowly to 60° C. and allow to react for 2 hours under stirring. The reaction solution was cooled to room temperature, and extracted with 100 mL of dichloromethane and the liquid was separated; and 100 mL of dichloromethane was then added to aqueous phase, and then the organic phases were combined and washed with 100 mL of saturated saline solution and the liquid was separated; and the organic phase was evaporated to obtain oily substance. The oily substance was then purified by chromatography separation using neutral $Al_2O_3$ or separated and purified by preparative HPLC to obtain 1-(4-chlorobutyl)-1H-substituted benzotriazole, with a yield of 30.0-85.0%.

General Synthetic Process VII: Preparation of 1-(4-(4-(substituted aryl) piperazin-1-yl)butyl)-1H-benzotriazole 1-(4-chlorobutyl)-1H-benzotriazole (0.036 mol) was dissolved in 100 ml of acetonitrile and added with a substituted arylpiperazine (0.03 mol), diisopropyl ethylamine (15.5 g, 0.12 mol), and potassium iodide (5.0 g, 0.03 mol), and then stirred for 10 minutes at room temperature, and allow to react for $10^{-2}0$ hours under heating and reflux. The solution was then cooled to room temperature, filtered, and the filtrate then concentrated to obtain an oily substance which is purified by chromatographic separation using neutral $Al_2O_3$, and then eluted with dichloromethane/methanol mixture to obtain the compound as described above, with a yield of 60.0-75.0%.

Example 1

Preparation of N-(4-(1H-benzimidazol-1-yl)butyl)-4-(3-chlorophenyl)piperidine (Compound I-1)

1H-benzimidazol (11.8 g, 0.10 mol) was dissolved in 200 mL of 20 wt % NaOH solution and was added Bromo-4-chloro-butane (34.3 g, 0.10 mol) and tetrabutylammonium bromide (1.0 g), and the resulting solution was mixed thoroughly for 5 minutes, heated to 60° C., and react for 2 hours under stirring. The reaction solution was cooled to room temperature, and extracted with 100 mL of dichloromethane and the liquid was separated; and 100 mL of dichloromethane was then added to aqueous phase, and then the organic phases were combined and washed with 100 mL of saturated saline solution and the liquid was separated; and the organic phase was evaporated to obtain oily substance. The oily substance was then purified by chromatography separation using neutral $Al_2O_3$ to obtain 1-(4-chlorobutyl)-1H-benzimidazole, with a yield of 60.0%.

1-(4-chlorobutyl)-1H-benzimidazol (7.51 g, 0.036 mol) was dissolved in 100 mL of acetonitrile. 3-chlorophenyl piperidine (5.9 g, 0.03 mol), diisopropylethyl amine (15.5 g, 0.12 mol), and potassium iodide (5.0 g, 0.03 mol) were added thereto. The resulting solution was stirred for 10 minutes at room temperature and react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane/methanol mixture to obtain 7.3 g of the compound (I-1), with a yield of 66.4%. ESI-MS $[M+H]^+$: m/z 368.2.

Example 2

Preparation of N-(4-(1H-benzotriazole-1-yl)butyl)-4-(3-chlorophenyl)piperidine (Compound I-2)

Benzotriazole (11.9 g, 0.10 mol) was dissolved in 100 mL of 30 wt % NaOH solution, and bromo-4-chloro-butane (34.3 g, 0.10 mol) and tetrabutylammonium bromide (0.8 g) were added and the resulting solution was mixed thoroughly for 5 minutes. Heat slowly to 60° C. and allow to react for 2 hours under stirring. The reaction solution was cooled to room temperature, and extracted with 100 mL of dichloromethane and the liquid was separated; and 100 mL of dichloromethane was then added to aqueous phase, and then the organic phases were combined and washed with 100 mL of saturated saline solution and the liquid was separated; and the organic phase was evaporated to obtain oily substance. The oily substance was then purified by chromatography separation using neutral $Al_2O_3$ to obtain 17.0 g of 1-(4-chloro-butyl)-1H-benzotriazole, with a yield of 81.0%.

1-(4-chloro-butyl)-1H-benzotriazole (7.55 g, 0.036 mol) was dissolved in 100 mL of acetonitrile. 3-chlorophenyl piperidine (5.9 g, 0.03 mol), diisopropylethyl amine (15.5 g, 0.12 mol), and potassium iodide (5.0 g, 0.03 mol) were added thereto. The resulting solution was stirred at room temperature and react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 7.8 g of the compound (I-2), with a yield of 70.3%. ESI-MS $[M+H]^+$: m/z 369.2.

Compound (I-2) (5.55 g, 0.015 mol) was dissolved in 50 ml of ethyl acetate. Under ice-water bath cooling, 3 mol of hydrogen chloride/ethyl acetate solution was added dropwise until a reaction solution of pH=2 was obtained; then the resulting solution was stirred for 10 min, filtered and dried to obtain 5.4 g of compound (II-2), with a yield of 88.0%.

Example 3

Preparation of N-(4-(1H-benzimidazol-1-yl)butyl)-4-(3-trifluoromethylphenyl)piperidine (I-3)

Prepare 1-(4-chlorobutyl)-1H-benzimidazol as described in example 1.

1-(4-chlorobutyl)-1H-benzimidazol (0.06 mol) was dissolved in 150 mL of acetonitrile. 4-(3-trifluoromethylphenyl)piperidine (0.05 mol), diisopropylethyl amine (0.2 mol), and potassium iodide (0.05 mol) were added thereto. The resulting solution was stirred for 10 minutes at room temperature and react for 15 hours under heating and reflux. The resulting solution was cooled to room temperature, filtered, and the filtrate was concentrated to obtain an oily substance which was purified by chromatographic separation using neutral $Al_2O_3$, and eluted using dichloromethane/methanol to obtain 11.0 g of N-(4-(1H-benzimidazol-1-yl)butyl yl)-4-(3-trifluoromethylphenyl)piperidine (I-3), with a yield of 64.9%. ESI-MS $[M+H]^+$: m/z 402.2.

Compound (I-3) (6.02 g, 0.015 mol) was dissolved in 50 ml of ethyl acetate. Under ice-water bath cooling, 3 mol of hydrogen chloride/ethyl acetate solution was added dropwise until a reaction solution of pH=2 was obtained; then the resulting solution was stirred for 10 min, filtered and dried to obtain 5.4 g of compound (II-2), with a yield of 89.0%.

Example 4

Preparation of N-(4-(1H-benzotriazole-1-yl)butyl)-4-(3-trifluoromethylphenyl)piperidine (Compound I-4)

Prepare 1-(4-chloro-butyl)-1H-benzotriazole as described in example 2.

1-(4-chloro-butyl)-1H-benzotriazole (0.06 mol) was dissolved in 150 mL of acetonitrile. 4-(3-trifluoromethylphenyl)piperidine (0.05 mol), diisopropylethyl amine (0.2 mol), and potassium iodide (0.05 mol) were added thereto. The resulting solution was stirred for 10 minutes at room temperature and react for 15 hours under heating and reflux. The resulting solution was cooled to room temperature, filtered, and the filtrate was concentrated to obtain an oily substance which was purified by chromatographic separation using neutral $Al_2O_3$, and eluted using dichloromethane/methanol to obtain 13.6 g of N-(4-(1H-benzotriazole-1-yl)butyl)-4-(3-trifluoromethylphenyl)piperidine (I-4), with a yield of 67.8%. ESI-MS $[M+H]^+$: m/z 403.2.

Example 5

Preparation of N-(4-(1H-benzimidazol-1-yl)butyl)-4-(3-fluorophenyl)piperidine (Compound I-5)

Prepare 1-(4-chlorobutyl)-1H-benzimidazol as described in example 1.

1-(4-chlorobutyl)-1H-benzimidazol (7.51 g, 0.036 mol) was dissolved in 100 mL of acetonitrile. 3-fluorophenyl piperidine (5.9 g, 0.03 mol), diisopropylethyl amine (15.5 g, 0.12 mol), and potassium iodide (5.0 g, 0.03 mol) were added thereto. The resulting solution was stirred for 10 minutes at room temperature and react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane/methanol mixture to obtain 7.1 g of the compound (I-5), with a yield of 67.2%. ESI-MS $[M+H]^+$: m/z 352.2.

Example 6

Preparation of N-(4-(1H-benzimidazol-1-yl)butyl)-4-(2-methoxyphenyl)piperidine (Compound I-6)

Prepare 1-(4-chlorobutyl)-1H-benzimidazol as described in example 1.

1-(4-chlorobutyl)-1H-benzimidazol (7.51 g, 0.036 mol) was dissolved in 100 mL of acetonitrile. 2-methoxy-phenyl piperidine (5.7 g, 0.03 mol), diisopropylethyl amine (15.5 g, 0.12 mol), and potassium iodide (5.0 g, 0.03 mol) were added thereto. The resulting solution was stirred for 10 minutes at room temperature and react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane/methanol mixture to obtain 6.7 g of the compound (I-6), with a yield of 61.3%. ESI-MS $[M+H]^+$: m/z 364.2.

Example 7

Preparation of N-(4-(6-fluoro-1H-benzotriazole-1-yl)butyl)-4-(3-trifluoromethylphenyl)piperidine (Compound I-7)

Fluoro-benzotriazole (15.3 g, 0.10 mol) was dissolved in 100 mL of 30 wt % NaOH solution, and bromo-4-chlorobutane (34.3 g, 0.20 mol) and tetrabutylammonium bromide (0.8 g) were added and the resulting solution was mixed thoroughly for 5 minutes. Heat slowly to 60° C. and allow to react for 2 hours under stirring. The reaction solution was cooled to room temperature, and extracted with 100 mL of dichloromethane and the liquid was separated; and 100 mL of dichloromethane was then added to aqueous phase, and then the organic phases were combined and washed with 100 mL of saturated saline solution and the liquid was separated; and the organic phase was evaporated to obtain oily substance. The oily substance was then purified by chromatography separation using neutral $Al_2O_3$ to obtain 17.0 g of 6-fluoro-1-(4-chloro-butyl)-1H-benzotriazole, with a yield of 77.0%.

6-fluoro-1-(4-chloro-butyl)-1H-benzotriazole (0.06 mol) was dissolved in 150 mL of acetonitrile. 4-(3-trifluoromethylphenyl)piperidine (0.05 mol), diisopropylethyl amine (0.2 mol), and potassium iodide (0.05 mol) were added thereto. The resulting solution was stirred for 10 minutes at room temperature and react for 15 hours under heating and reflux. The resulting solution was cooled to room temperature, filtered, and the filtrate was concentrated to obtain an oily substance which was purified by chromatographic separation using neutral $Al_2O_3$, and eluted using dichloromethane/methanol to obtain 13.5 g of N-(4-(1H-benzotriazole-1-yl)butyl)-4-(3-trifluoromethylphenyl)piperidine (I-7), with a yield of 64.1%. ESI-MS $[M+H]^+$: m/z 421.2.

Example 8

Preparation of N-(4-(6-methoxy-1H-benzotriazole-1-yl)butyl)-4-(3-trifluoromethylphenyl)piperidine (Compound I-8)

6-methoxy-benzotriazole (14.9 g, 0.10 mol) was dissolved in 100 mL of 30 wt % NaOH solution, and bromo-4-chloro-butane (34.3 g, 0.10 mol) and tetrabutylammonium bromide (0.8 g) were added and the resulting solution was mixed thoroughly for 5 minutes. Heat slowly to 60° C. and allow to react for 2 hours under stirring. The reaction solution was cooled to room temperature, and extracted with 100 mL of dichloromethane and the liquid was separated; and 100 mL of dichloromethane was then added to aqueous phase, and then the organic phases were combined and washed with 100 mL of saturated saline solution and the liquid was separated; and the organic phase was evaporated to obtain oily substance. The oily substance was then purified by chromatography separation using neutral $Al_2O_3$ and eluted by dichloromethane to obtain 17.9 g of 6-methoxy-1-(4-chloro-butyl)-1H-benzotriazole, with a yield of 75.0%.

6-methoxy-1-(4-chloro-butyl)-1H-benzotriazole (0.06 mol) was dissolved in 150 mL of acetonitrile. 4-(3-trifluoromethylphenyl)piperidine (0.05 mol), diisopropylethyl amine (0.2 mol), and potassium iodide (0.05 mol) were added thereto. The resulting solution was stirred for 10 minutes at room temperature and react for 15 hours under heating and reflux. The resulting solution was cooled to room temperature, filtered, and the filtrate was concentrated to obtain an oily substance which was purified by chromatographic separation using neutral $Al_2O_3$, and eluted using dichloromethane/methanol to obtain 14.0 g of N-(4-(1H-benzotriazole-1-yl)butyl)-4-(3-trifluoromethylphenyl)piperidine (I-8), with a yield of 64.6%. ESI-MS [M+H]$^+$: m/z 433.2.

Example 9

Preparation of N-(4-(6-cyano-1H-benzotriazole-1-yl)butyl)-4-(3-trifluoromethylphenyl)piperidine (Compound I-9)

6-methoxy-benzotriazole (14.4 g, 0.10 mol) was dissolved in 100 mL of 30 wt % NaOH solution, and bromo-4-chloro-butane (34.3 g, 0.20 mol) and tetrabutylammonium bromide (0.8 g) were added and the resulting solution was mixed thoroughly for 5 minutes. Heat slowly to 60° C. and allow to react for 2 hours under stirring. The reaction solution was cooled to room temperature, and extracted with 100 mL of dichloromethane and the liquid was separated; and 100 mL of dichloromethane was then added to aqueous phase, and then the organic phases were combined and washed with 100 mL of saturated saline solution and the liquid was separated; and the organic phase was evaporated to obtain oily substance. The oily substance was then purified by chromatography separation using neutral $Al_2O_3$ and eluted using dichloromethane to obtain 17.3 g of 6-cyano-1-(4-chloro-butyl)-1H-benzotriazole, with a yield of 74.0%.

6-cyano-1-(4-chloro-butyl)-1H-benzotriazole (0.06 mol) was dissolved in 150 mL of acetonitrile. 4-(3-trifluoromethylphenyl)piperidine (0.05 mol), diisopropylethyl amine (0.2 mol), and potassium iodide (0.05 mol) were added thereto. The resulting solution was stirred for 10 minutes at room temperature and react for 15 hours under heating and reflux. The resulting solution was cooled to room temperature, filtered, and the filtrate was concentrated to obtain an oily substance which was purified by chromatographic separation using neutral $Al_2O_3$, and eluted using dichloromethane/methanol to obtain 13.5 g of N-(4-(1H-benzotriazole-1-yl)butyl)-4-(3-trifluoromethylphenyl)piperidine (I-9), with a yield of 63.1%. ESI-MS [M+H]$^+$: m/z 427.2.

Example 10

Preparation of N-(4-(1H-benzotriazole-1-yl) propoxy)-4-(3-trifluoromethylphenyl)piperidine (Compound I-10)

Preparation of N-(2-chloropropoxy)-benzotriazole 1-hydroxy-triazole (0.1 mol) was dissolved in 10 mL of NMP, and a mixture containing 50% wt sodium hydride and solid wax was added in portions, and react for 0.5 hour under stirring. At the same time, dissolve 3-chloro-bromopropane (0.015 mol) in 5 ml of NMP, and add the solution in the mixture solution above, and allow to react under room temperature for 12 hours under stirring. The reaction solution is then poured into 50 ml of water and extracted with ethyl acetate (3×50 mL); then the organic phases are combined and washed with 30 mL of water; Anhydrous magnesium sulfate was then used to dry the organic phase, which was then filtered and evaporated to dryness; the oily substance obtained was then purified by chromatography using neutral $Al_2O_3$ or separated and purified by preparative HPLC to obtain 1-(3-chloropropoxy)benzotriazole with a yield of 75.0-85.0%.

1-(3-chloropropoxy)benzotriazole (0.06 mol) was dissolved in 150 mL of acetonitrile. 4-(3-(6-fluoro-benzisoxazolyl))piperidine (0.05 mol), diisopropylethyl amine (0.2 mol), and potassium iodide (0.05 mol) were added thereto. The resulting solution was stirred for 10 minutes at room temperature and react for 15 hours under heating and reflux. The resulting solution was cooled to room temperature, filtered, and the filtrate was concentrated to obtain an oily substance which was purified by chromatographic separation using neutral $Al_2O_3$, and eluted using dichloromethane/methanol to obtain 13.2 g of N-(4-(1H-benzotriazole-1-yl)butyl)-4-(3-trifluoromethylphenyl)piperidine N-(4-(1H-benzotriazole-1-yl) propoxy)-4-(3-trifluoromethylphenyl) piperidine (I-10), with a yield of 65.3%. ESI-MS [M+H]$^+$: m/z 405.2.

Example 11

Preparation of N-(4-(1H-benzimidazol-1-yl) propoxy)-4-(3-trifluoromethylphenyl)piperidine (I-11)

Preparation of N-(2-chloropropoxy)-benzimidazol

Imidazol-1-hydroxybenzotriazole (0.01 mol) was dissolved in 10 mL of NMP, and a mixture containing 50% wt sodium hydride and solid wax was added in portions, and react for 0.5 hour under stirring. At the same time, dissolve 3-chloro-bromopropane (0.015 mol) in 5 ml of NMP, and add the solution in the mixture solution above, and allow to react under room temperature for 12 hours under stirring. The reaction solution is then poured into 50 ml of water and extracted with ethyl acetate (3×50 mL); then the organic phases are combined and washed with 30 mL of water; Anhydrous magnesium sulfate was then used to dry the organic phase, which was then filtered and evaporated to dryness; the oily substance obtained was then purified by chromatography using neutral $Al_2O_3$ or separated and purified by preparative HPLC to obtain 1-(3-chloropropoxy) benzimidazole with a yield of 75.0%.

1-(3-chloropropoxy)benzimidazole (0.06 mol) was dissolved in 150 mL of acetonitrile. 4-(3-(6-fluoro-benzisoxazolyl))piperidine (0.05 mol), diisopropylethyl amine (0.2 mol), and potassium iodide (0.05 mol) were added thereto. The resulting solution was stirred for 10 minutes at room temperature and react for 15 hours under heating and reflux. The resulting solution was cooled to room temperature, filtered, and the filtrate was concentrated to obtain an oily substance which was purified by chromatographic separation using neutral $Al_2O_3$, and eluted using dichloromethane/methanol to obtain 13.6 g of N-(4-(1H-benzimidazol-1-yl) propoxy)-4-(3-trifluoromethylphenyl) (I-11), with a yield of 67.1%. ESI-MS [M+H]$^+$: m/z 404.2.

Example 12

Preparation of N-(3-(1H-benzotriazole-1-yl)propyl)-4-(3-(6-methyl-benzisoxazole))piperidine (Compound I-12)

1-(3-chloropropyl)-1H-benzotriazole (11.7 g, 0.06 mol) was dissolved in 150 mL of acetonitrile. 6-methyl-3-(4-yl)

benzisoxazole (10.8 g, 0.05 mol), diisopropylethyl amine (25.8 g, 0.2 mol), and potassium iodide (8.3 g, 0.05 mol) were added thereto. The resulting solution was stirred for 10 minutes at room temperature and react for 15 hours under heating and reflux. Carry out remaining procedures as per general synthetic process II to obtain 12.4 g of compound I-12, with a yield of 66.1%. ESI-MS [M+H]$^+$: m/z 376.2.

Example 13

Preparation of N-(3-(1H-benzotriazole-1-yl)propyl)-4-(3-(6-methoxy-benzene and isoxazole)) piperidine (Compound I-13)

1-(3-chloropropyl)-1H-benzotriazole (11.7 g, 0.06 mol) was dissolved in 150 mL of acetonitrile. 6-methoxy-3-(4-yl)benzoisoxazole (11.6 g, 0.05 mol), diisopropylethyl amine (25.8 g, 0.2 mol), and potassium iodide (8.3 g, 0.05 mol) were added thereto. The resulting solution was stirred for 10 minutes at room temperature and react for 15 hours under heating and reflux. Carry out remaining procedures as per general synthetic process II to obtain 13.3 g of compound (I-13), with a yield of 67.7%. ESI-MS [M+H]$^+$: m/z 392.2.

Example 14

Preparation of N-(3-(6-fluoro-1H-benzotriazole-1-yl)propyl)-4-(3-(6-fluorobenzo isoxazole)) piperidine (Compound I-14)

Preparation of 1-(3-chloropropyl)-6-fluoro-1H-benzotriazole 6-fluoro-1H-benzotriazole (13.7 g, 0.10 mol) was dissolved in 100 mL of 30 wt % NaOH solution, and 3-chlorobromopropane (31.4 g, 0.10 mol) and tetrabutylammonium bromide (0.8 g) were added and solution was mixed thoroughly for 5 minutes. Heat slowly to 60° C. and allow to react for 2 hours under stirring. Carry out remaining procedures as per general synthetic process I to obtain 6.9 g of 1-(3-chloropropyl)-6-fluoro-1H-benzotriazole, with a yield of 32.3%.

Preparation of N-(3-(6-fluoro-1H-benzotriazole-1-yl)propyl)-4-(3-(6-fluorobenzo isoxazole)) piperidine (Compound I-14)

1-(3-chloropropyl)-6-fluoro-1H-benzotriazole (6.41 g, 0.03 mol) was dissolved in 150 mL of acetonitrile. 6-fluoro-3-(piperidin-4-yl)benzisoxazole (5.5 g, 0.025 mol), diisopropylethyl amine (12.9 g, 0.1 mol), and potassium iodide (4.15 g, 0.025 mol) were added thereto. The resulting solution was stirred for 10 minutes at room temperature and react for 16 hours under heating and reflux. Carry out remaining procedures as per general synthetic process II to obtain 8.3 g of compound I-14, with a yield of 69.6%. ESI-MS [M+H]$^+$: m/z 398.2.

Example 15

Preparation of N-(3-(6-chloro-1H-benzotriazole-1-yl)propyl)-4-(3-(6-fluorobenzo isoxazole)) piperidine (Compound I-15)

Preparation of 1-(3-chloropropyl)-6-Chloro-1H-benzotriazole 6-chloro-1H-benzotriazole (15.4 g, 0.10 mol) was dissolved in 100 mL of 30 wt % NaOH solution, and 3-chlorobromopropane (31.4 g, 0.10 mol) and tetrabutylammonium bromide (0.8 g) were added and solution was mixed thoroughly for 5 minutes. Heat slowly to 60° C. and allow to react for 2 hours under stirring. Carry out remaining procedures as per general synthetic process I to obtain 7.3 g of 1-(3-chloropropyl)-6-chloro-1H-benzotriazole 7.3 g, with a yield of 31.7%.

Preparation of N-(3-(6-chloro-1H-benzotriazole-1-yl)propyl)-4-(3-(6-fluorobenzo isoxazole)) piperidine (Compound I-15)

1-(3-chloropropyl)-6-chloro-1H-benzotriazole (6.90 g, 0.03 mol) was dissolved in 150 mL of acetonitrile. 6-fluoro-3-(piperidin-4-yl)benzisoxazole (5.5 g, 0.025 mol), diisopropylethyl amine (12.9 g, 0.1 mol), and potassium iodide (4.15 g, 0.025 mol) were added thereto. The resulting solution was stirred for 10 minutes at room temperature and react for 16 hours under heating and reflux. Carry out remaining procedures as per general synthetic process II to obtain 8.1 g of compound I-15, with a yield of 65.2%. ESI-MS [M+H]$^+$: m/z 414.1.

Example 16

Preparation of N-(3-(6-methyl-1H-benzotriazole-1-yl)propyl)-4-(3-(6-fluorobenzo isoxazole)) piperidine (Compound I-16)

Preparation of 1-(3-chloropropyl)-6-methyl-1H-benzotriazole 6-methyl-1H-benzotriazole (13.3 g, 0.10 mol) was dissolved in 100 mL of 30 wt % NaOH solution, and 3-chlorobromopropane (31.4 g, 0.10 mol) and tetrabutylammonium bromide (0.8 g) were added and solution was mixed thoroughly for 5 minutes. Heat slowly to 60° C. and allow to react for 2 hours under stirring. Carry out remaining procedures as per general synthetic process I to obtain 7.2 g of 1-(3-chloropropyl)-6-methyl-1H-benzotriazole, with a yield of 34.3%.

Preparation of N-(3-(6-methyl-1H-benzotriazole-1-yl)propyl)-4-(3-(6-fluorobenzo isoxazole)) piperidine (Compound I-16)

1-(3-chloropropyl)-6-methyl-1H-benzotriazole (6.29 g, 0.03 mol) was dissolved in 100 mL of acetonitrile. 6-fluoro-3-(4-yl)benzisoxazole (5.5 g, 0.025 mol), diisopropylethyl amine (12.9 g, 0.1 mol), and potassium iodide (4.15 g, 0.025 mol) were added thereto. The resulting solution was stirred for 10 minutes at room temperature and react for 16 hours under heating and reflux. Carry out remaining procedures as per general synthetic process II to obtain 8.5 g of compound I-16, with a yield of 71.9%. ESI-MS [M+H]$^+$: m/z 394.2.

Example 17

Preparation of N-(3-(6-methoxy-1H-benzotriazole-1-yl)propyl)-4-(3-(6-fluorobenzo isoxazole)) piperidine (Compound I-17)

Preparation of N-(3-chloropropyl) methoxybenzothiazole triazole 6-methoxy-1H-benzotriazole (14.9 g, 0.10 mol) was dissolved in 100 mL of 30 wt % NaOH solution, and 3-chlorobromopropane (31.4 g, 0.10 mol) and tetrabutylammonium bromide (0.8 g) were added and solution was mixed thoroughly for 5 minutes. Heat slowly to 60° C. and allow to react for 2 hours under stirring. Carry out remaining procedures as per general synthetic process I to obtain 7.7 g of N-(3-chloropropyl) methoxybenzothiazole triazole, with a yield of 34.1%.

Preparation of N-(3-(6-methoxy-1H-benzotriazole-1-yl)propyl)-4-(3-(6-fluorobenzo isoxazole))piperidine (Compound I-17)

1-(3-chloropropyl)-6-methoxy-1H-benzotriazole (6.77 g, 0.03 mol) was dissolved in 100 mL of acetonitrile. 6-fluoro-3-(piperidin-4-yl)benzisoxazole (5.5 g, 0.025 mol), diisopropylethyl amine (12.9 g, 0.1 mol), and potassium iodide (4.15 g, 0.025 mol) were added thereto. The resulting solution was stirred for 10 minutes at room temperature and react for 16 hours under heating and reflux. Carry out remaining procedures as per general synthetic process II to obtain 8.6 g of compound I-17, with a yield of 70.0%. ESI-MS [M+H]$^+$: m/z 410.2.

Example 18

Preparation of N-(3-(6-formyl-1H-benzotriazole-1-yl)propyl)-4-(3-(6-fluorobenzo isoxazole))piperidine (Compound I-18)

Preparation of 1-(3-chloropropyl)-6-formyl-1H-benzotriazole 6-formyl-1H-benzotriazole (16.2 g, 0.10 mol) was dissolved in 100 mL of 30 wt % NaOH solution, and 3-chloro-bromopropane (31.4 g, 0.10 mol) and tetrabutylammonium bromide (0.8 g) were added and solution was mixed thoroughly for 5 minutes. Heat slowly to 60° C. and allow to react for 2 hours under stirring. Carry out remaining procedures as per general synthetic process I to obtain 7.9 g of 1-(3-chloropropyl)-6-formyl-1H-benzotriazole, with a yield of 33.2%.

Preparation of N-(3-(6-formyl-1H-benzotriazole-1-yl)propyl)-4-(3-(6-fluorobenzo isoxazole)) piperidine (Compound I-18)

1-(3-chloropropyl)-6-formyl-1H-benzotriazole (6.77 g, 0.03 mol) was dissolved in 150 mL of acetonitrile. 6-fluoro-3-(piperidin-4-yl)benzisoxazole (5.5 g, 0.025 mol), diisopropylethyl amine (12.9 g, 0.1 mol), and potassium iodide (4.15 g, 0.025 mol) were added thereto. The resulting solution was stirred for 10 minutes at room temperature and react for 15 hours under heating and reflux. Carry out remaining procedures as per general synthetic process II to obtain 7.5 g of compound I-18, with a yield of 73.6%. ESI-MS [M+H]$^+$: m/z 408.2.

Example 19

Preparation of N-(3-(6-methoxybenzo triazole-yl) propyl)-4-(3-benzoisoxazole)piperidine (Compound I-19)

Prepare N-(3-chloropropyl)-6-methoxybenzothiazole triazole as described in example 17.

N-(3-chloropropyl)-6-methoxybenzothiazole triazole (0.06 mol) was dissolved in 150 mL of acetonitrile. 4-(3-benzoisoxazole)piperidine (0.05 mol), diisopropylethyl amine (0.2 mol), and potassium iodide (0.05 mol) were added thereto. The resulting solution was stirred for 10 minutes at room temperature and react for 15 hours under heating and reflux. The resulting solution was cooled to room temperature, filtered, and the filtrate was concentrated to obtain an oily substance which was purified by chromatographic separation using neutral Al$_2$O$_3$, and eluted using dichloromethane/methanol to obtain 13.14 g of N-(3-(6-methoxybenzo triazole-yl)propyl)-4-(3-benzoisoxazole)piperidine (I-19), with a yield of 67.2%. ESI-MS [M+H]$^+$: m/z 391.2.

Example 20

Preparation of N-(2-(1-benzotriazole-yl)ethyl)-4-(3-(6-fluorobenzo isoxazole))piperidine (Compound I-20)

Benzotriazole (11.9 g, 0.10 mol) was dissolved in 100 mL of 30 wt % NaOH solution, and 3-chloro-bromopropane (31.4 g, 0.10 mol) and tetrabutylammonium bromide (0.8 g) were added and solution was mixed thoroughly for 5 minutes. Heat slowly to 60° C. and allow to react for 2 hours under stirring. The reaction solution was cooled to room temperature, and extracted with 100 mL of dichloromethane and the liquid was separated; and 100 mL of dichloromethane was then added to aqueous phase, and then the organic phases were combined and washed with 100 mL of saturated saline solution and the liquid was separated; and the organic phase was evaporated to obtain oily substance. The oily substance was then separated and purified using column chromatography (neutral Al$_2$O$_3$), and then further eluted and separated by dichloromethane to obtain 16.0 g of 1-(3-chloropropyl)-1H-benzotriazole, with a yield of 82.0%.

1-(3-chloropropyl)-1H-benzotriazole (0.06 mol) was dissolved in 150 mL of acetonitrile. 4-(3-(6-fluorobenzo isoxazole))piperidine (0.05 mol), diisopropylethyl amine (0.2 mol), and potassium iodide (0.05 mol) were added thereto. The resulting solution was stirred for 10 minutes at room temperature and react for 15 hours under heating and reflux. The resulting solution was cooled to room temperature, filtered, and the filtrate was concentrated to obtain an oily substance which was purified by chromatographic separation using neutral Al$_2$O$_3$, and eluted using dichloromethane/methanol to obtain 12.67 g of N-(2-(1-1-benzotriazole-yl) ethyl)-4-(3-(6-fluorobenzo isoxazole))piperidine (I-20), with a yield of 69.4%. ESI-MS [M+H]$^+$: m/z 365.2.

Example 21

Preparation of N-(4-(1-benzotriazole-yl)butyl)-4-(3-(6-fluorobenzo isoxazole))piperidine (Compound I-21)

Prepare 1-(4-chloro-butyl)-1H-benzotriazole as described in example 2.

1-(4-chloropropyl)-1H-benzotriazole (0.06 mol) was dissolved in 150 mL of acetonitrile. 4-(3-(6-fluorobenzo isoxazole))piperidine (0.05 mol), diisopropylethyl amine (0.2 mol), and potassium iodide (0.05 mol) were added thereto. The resulting solution was stirred for 10 minutes at room temperature and react for 15 hours under heating and reflux. The resulting solution was cooled to room temperature, filtered, and the filtrate was concentrated to obtain an oily substance which was purified by chromatographic separation using neutral Al$_2$O$_3$, and eluted using dichloromethane/ methanol to obtain 13.96 g of N-(4-(1-benzotriazole-yl) butyl)-4-(3-(6-fluorobenzo isoxazole))piperidine (I-21), with a yield of 71.0%. ESI-MS [M+H]$^+$: m/z 393.2.

Example 22

Preparation of N-(4-(6-cyano-benzotriazole-yl)butyl)-4-(3-(6-fluorobenzo isoxazole))piperidine (Compound I-22)

Preparation of 1-(3-chloro-butyl)-6-cyano-1H-benzotriazole 6-cyano-1H-benzotriazole (15.9 g, 0.10 mol) was dissolved in 100 mL of 30 wt % NaOH solution, and 3-chloro-bromobutane (32.6 g, 0.10 mol) and tetrabutylammonium bromide (0.8 g) were added and the resulting solution was mixed thoroughly for 5 minutes. Heat slowly to 60° C. and allow to react for 2 hours under stirring. Carry out remaining procedures as per general synthetic process I to obtain 9.1 g of 1-(3-chloro-butyl)-6-cyano-1H-benzotriazole, with a yield of 32.6%.

1-(3-chloro-butyl)-6-cyano-benzotriazole (0.06 mol) was dissolved in 150 mL of acetonitrile. 4-(3-(6-fluorobenzo isoxazole))piperidine (0.05 mol), diisopropylethyl amine (0.2 mol), and potassium iodide (0.05 mol) were added thereto. The resulting solution was stirred for 10 minutes at room temperature and react for 15 hours under heating and reflux. The resulting solution was cooled to room temperature, filtered, and the filtrate was concentrated to obtain an oily substance which was purified by chromatographic separation using neutral Al$_2$O$_3$, and eluted using dichloromethane/methanol to obtain 15.07 g of N-(4-(6-cyano-benzotriazole-yl)butyl)-4-(3-(6-fluorobenzo isoxazole))piperidine (I-22), with a yield of 72.1%. ESI-MS [M+H]$^+$: m/z 418.2.

Example 23

Preparation of N-(4-(6-cyano-benzotriazole-yl)butyl)-4-(3-(6-methoxy-benzene and isoxazole)) piperidine (Compound I-23)

Prepare 1-(3-chloro-butyl)-6-cyano benzotriazole as described in example 22.

1-(3-chloro-butyl)-6-cyano-benzotriazole (0.06 mol) was dissolved in 150 mL of acetonitrile. 4-(3-(6-methoxy-benzene and isoxazole))piperidine (0.05 mol), diisopropylethyl amine (0.2 mol), and potassium iodide (0.05 mol) were added thereto. The resulting solution was stirred for 10 minutes at room temperature and react for 15 hours under heating and reflux. The resulting solution was cooled to room temperature, filtered, and the filtrate was concentrated to obtain an oily substance which was purified by chromatographic separation using neutral Al$_2$O$_3$, and eluted using dichloromethane/methanol to obtain 15.01 g of N-(4-(6-cyano-benzotriazole-yl)butyl)-4-(3-(6-methoxy-benzene and isoxazole))piperidine (I-23), with a yield of 69.8%. ESI-MS [M+H]$^+$: m/z 430.2.

Example 24

Preparation of N-(2-(6-methoxybenzo triazole) ethoxy)-4-(3-benzoisoxazole)piperidine (Compound I-24)

Prepare N-hydroxy-6-methoxybenzene triazole as described in general synthetic method III.

According to general synthetic method I, N-hydroxy-6-methoxybenzene triazole was used to prepare N-(2-chloroethoxy methoxybenzothiazole triazole (0.06 mol) which is then dissolved in 150 mL of acetonitrile. Then 4-(3-benzisoxazolyl)piperidine (0.05 mol), diisopropylethyl amine (0.2 mol), and potassium iodide (0.05 mol) were added thereto. The resulting solution was stirred for 10 minutes at room temperature and react for 15 hours under heating and reflux. The resulting solution was cooled to room temperature, filtered, and the filtrate was concentrated to obtain an oily substance which was purified by chromatographic separation using neutral Al$_2$O$_3$, and eluted using dichloromethane/methanol to obtain 14.21 g of N-(2-(6-methoxybenzo triazole) ethoxy)-4-(3-benzoisoxazole)piperidine (I-24), with a yield of 69.1%. ESI-MS [M+H]$^+$: m/z 394.2.

Example 25

Preparation of 1-25 N-(2-(1-benzotriazole) ethoxy)-4-(3-fluoro-benzisoxazole)piperidine Prepare N-hydroxybenzotriazole triazole as described in general synthetic method III.

According to general synthetic method I, N-hydroxybenzotriazole triazole was used to prepare N-2-chloroethoxy benzotriazole (0.06 mol) which is then dissolved in 150 mL of acetonitrile. Then 4-(3-benzisoxazolyl)piperidine (0.05 mol), diisopropylethyl amine (0.2 mol), and potassium iodide (0.05 mol) were added thereto. The resulting solution was stirred for 10 minutes at room temperature and react for 15 hours under heating and reflux. The resulting solution was cooled to room temperature, filtered, and the filtrate was concentrated to obtain an oily substance which was purified by chromatographic separation using neutral Al$_2$O$_3$, and eluted using dichloromethane/methanol to obtain 12.88 g of N-(2-(1-benzotriazole) ethoxy)-4-(3-fluoro-benzisoxazole) piperidine (I-25), with a yield of 67.6%. ESI-MS [M+H]$^+$: m/z 364.2.

Example 26

Preparation of N-(3-(6-methoxybenzo triazole-yl) propyl)-4-(3-(6-fluorophenyl and isothiazole)) piperidine (Compound I-26)

Prepare N-(3-chloropropyl)-6-methoxybenzothiazole triazole as described in example 17.

N-(3-chloropropyl) methoxybenzothiazole triazole (0.06 mol) was dissolved in 150 mL of acetonitrile. 4-(3-(6-fluorobenzo isoxazole))piperidine (0.05 mol), diisopropylethyl amine (0.2 mol), and potassium iodide (0.05 mol) were added thereto. The resulting solution was stirred for 10 minutes at room temperature and react for 15 hours under heating and reflux. The resulting solution was cooled to room temperature, filtered, and the filtrate was concentrated to obtain an oily substance which was purified by chromatographic separation using neutral Al$_2$O$_3$, and eluted using dichloromethane/methanol to obtain 13.17 g of N-(3-(6-methoxybenzo triazole-yl)propyl)-4-(3-(6-fluorophenyl and isothiazole))piperidine (I-26), with a yield of 69.1%. ESI-MS [M+H]$^+$: m/z 426.1.

Example 27

Preparation of N-(3-(6-methoxybenzo triazole-yl) propyl)-4-(3-(6-fluorobenzo pyrazol))piperidine (Compound I-27)

Prepare N-(3-chloropropyl)-6-methoxybenzothiazole triazole as described in example 17.

N-(3-chloropropyl) methoxybenzothiazole triazole (0.06 mol) was dissolved in 150 mL of acetonitrile. 4-(3-(6-fluorophenyl and isothiazole)) (0.05 mol), diisopropylethyl amine (0.2 mol), and potassium iodide (0.05 mol) were added thereto. The resulting solution was stirred for 10 minutes at room temperature and react for 15 hours under heating and reflux. The resulting solution was cooled to room temperature, filtered, and the filtrate was concentrated to obtain an oily substance which was purified by chromatographic separation using neutral $Al_2O_3$, and eluted using dichloromethane/methanol to obtain 12.11 g of N-(3-(6-methoxybenzo triazole-yl)propyl)-4-(3-(6-fluorobenzo pyrazol))piperidine (I-27), with a yield of 66.5%. ESI-MS $[M+H]^+$: m/z 409.2.

Example 28

Preparation of N-(3-(6-methoxybenzo triazole-yl) propyl)-4-(3-(6-furan-fluorophenyl))piperidine (Compound I-28)

Prepare N-(3-chloropropyl)-6-methoxybenzothiazole triazole as described in example 17.

N-(3-chloropropyl) methoxybenzothiazole triazole (0.06 mol) was dissolved in 150 mL of acetonitrile. 4-(3-(6-fluorophenyl and isothiazole)) (0.05 mol), diisopropylethyl amine (0.2 mol), and potassium iodide (0.05 mol) were added thereto. The resulting solution was stirred for 10 minutes at room temperature and react for 15 hours under heating and reflux. The resulting solution was cooled to room temperature, filtered, and the filtrate was concentrated to obtain an oily substance which was purified by chromatographic separation using neutral $Al_2O_3$, and eluted using dichloromethane/methanol to obtain 12.40 g of N-(3-(6-methoxybenzo triazole-yl)propyl)-4-(3-(6-furan-fluorophenyl))piperidine (I-28), with a yield of 68.1%. ESI-MS $[M+H]^+$: m/z 409.2.

Example 29

Preparation of N-(4-(1H-benzimidazol-1-yl)butyl)-4-(2-furyl)piperidine (I-29)

Prepare 1-(4-chlorobutyl)-1H-benzimidazol as described in example 1.

1-(4-chlorobutyl)-1H-benzimidazol (7.51 g, 0.036 mol) was dissolved in 100 mL of acetonitrile. 4-(2-furyl)piperidine (4.6 g, 0.03 mol), diisopropyl ethylamine (15.5 g, 0.12 mol), and potassium iodide (5.0 g, 0.03 mol) were added thereto. The resulting solution was stirred for 10 minutes at room temperature and react for 20 hours under heating and reflux. The solution was then cooled to room temperature, filtered, and the filtrate then concentrated to obtain an oily substance which is purified by chromatographic separation using neutral $Al_2O_3$, and then eluted with dichloromethane/methanol mixture to obtain 6.0 g of the compound (I-29), with a yield of 61.6%. ESI-MS $[M+H]^+$: m/z 324.2.

Example 30

Preparation of N-(4-(1H-benzimidazol-1-yl)butyl)-4-(4-pyridyl)piperidine (Compound I-30)

Prepare 1-(4-chlorobutyl)-1H-benzimidazol as described in example 1.

1-(4-chlorobutyl)-1H-benzimidazol (7.51 g, 0.036 mol) was dissolved in 100 mL of acetonitrile. 4-(4-pyridyl)piperidine (4.9 g, 0.03 mol), diisopropyl ethylamine (15.5 g, 0.12 mol), and potassium iodide (5.0 g, 0.03 mol) were added thereto. The resulting solution was stirred for 10 minutes at room temperature and react for 20 hours under heating and reflux. The solution was then cooled to room temperature, filtered, and the filtrate then concentrated to obtain an oily substance which is purified by chromatographic separation using neutral $Al_2O_3$, and then eluted with dichloromethane/methanol mixture to obtain 6.3 g of the compound (I-30), with a yield of 62.1%. ESI-MS $[M+H]^+$: m/z 335.2.

Example 31

Preparation of N-(4-(1H-benzimidazol-1-yl)butyl)-4-(2-pyrimidinyl)piperidine (I-31)

Prepare 1-(4-chlorobutyl)-1H-benzimidazol as described in example 1.

1-(4-chlorobutyl)-1H-benzimidazol (7.51 g, 0.036 mol) was dissolved in 100 mL of acetonitrile. 4-(2-pyrimidinyl)piperidine (4.9 g, 0.03 mol), diisopropyl ethylamine (15.5 g, 0.12 mol), and potassium iodide (5.0 g, 0.03 mol) were added thereto. The resulting solution was stirred for 10 minutes at room temperature and react for 20 hours under heating and reflux. The solution was then cooled to room temperature, filtered, and the filtrate then concentrated to obtain an oily substance which is purified by chromatographic separation using neutral $Al_2O_3$, and then eluted with dichloromethane/methanol mixture to obtain 6.1 g of the compound (I-31), with a yield of 60.1%. ESI-MS $[M+H]^+$: m/z 336.2.

Example 32

Preparation of N-(4-(1H-benzotriazole-1-yl)butyl)-4-cyclohexyl-piperidine (Compound I-32)

Prepare 1-(4-chloro-butyl)-1H-benzotriazole as described in example 2.

1-(4-chloro-butyl)-1H-benzotriazole (7.55 g, 0.036 mol) was dissolved in 100 mL of acetonitrile. 4-(1-cyclohexyl-yl)piperidine (5.1 g, 0.03 mol), diisopropyl ethylamine (15.5 g, 0.12 mol), and potassium iodide (5.0 g, 0.03 mol) were added thereto. The resulting solution was stirred at room temperature and react for 20 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 6.5 g of the compound (I-32), with a yield of 63.7%. ESI-MS $[M+H]^+$: m/z 341.3.

Example 33

Preparation of N-(4-(1H-benzotriazole-1-yl)butyl)-4-(1-naphthyl)piperidine (I-33)

Prepare 1-(4-chloro-butyl)-1H-benzotriazole as described in example 2.

1-(4-chloro-butyl)-1H-benzotriazole (7.55 g, 0.036 mol) was dissolved in 100 mL of acetonitrile. 4-(1-naphthyl)piperidine (6.4 g, 0.03 mol), diisopropyl ethylamine (15.5 g, 0.12 mol), and potassium iodide (5.0 g, 0.03 mol) were added thereto. The resulting solution was stirred and react for 20 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 6.9 g of the compound (I-33), with a yield of 60.1%. ESI-MS [M+H]$^+$: m/z 385.3.

Example 34

Preparation of N-(4-(1H-benzotriazole-1-yl)butyl)-4-(2-quinoxaline-yl)piperidine (Compound I-34)

Prepare 1-(4-chloro-butyl)-1H-benzotriazole as described in example 2.

1-(4-chloro-butyl)-1H-benzotriazole (7.55 g, 0.036 mol) was dissolved in 100 mL of acetonitrile. 4-(2-quinoxaline-yl)piperidine (6.4 g, 0.03 mol), diisopropyl ethylamine (15.5 g, 0.12 mol), and potassium iodide (5.0 g, 0.03 mol) were added thereto. The resulting solution was stirred and react for 20 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 7.3 g of the compound (I-34), with a yield of 62.7%. ESI-MS [M+H]$^+$: m/z 387.2.

Example 35

Preparation of 1-(4-(4-(3-chlorophenyl) piperazin-1-yl)butyl)-1H-benzimidazole (Compound I-35)

The substituted 1H-benzimidazol (11.8 g, 0.10 mol) was dissolved in 100 mL of 30 wt % sodium hydroxide aqueous solution and then was added with 4-Chloro-bromobutane (34.3 g, 0.20 mol), tetrabutylammonium bromide (1.0 g, 0.003 mol); it is then mixed and stirred for 5 minutes, heated to 60° C. and react for 2 hours under stirring. The reaction solution was cooled to room temperature, and extracted with 100 mL of dichloromethane and the liquid was separated; and 100 mL of dichloromethane was then added to aqueous phase, and then the organic phases were combined and washed with 100 mL of saturated saline solution and the liquid was separated; and the organic phase was evaporated to obtain oily substance. The oily substance was then purified by chromatography separation using neutral $Al_2O_3$ to obtain 1-(4-chlorobutyl)-1H-benzimidazole, with a yield of 60.0%.

1-(4-chlorobutyl)-1H-benzimidazol (7.51 g, 0.036 mol) was dissolved in 100 ml of acetonitrile and added with 3-trichlorophenyl piperazine (5.9 g, 0.03 mol), diisopropyl ethylamine (15.5 g, 0.12 mol), and potassium iodide (5.0 g, 0.03 mol), and then stirred for 10 minutes at room temperature, and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane/methanol mixture to obtain 6.8 g of the compound (I-35), with a yield of 61.4%. ESI-MS [M+H]$^+$: m/z 369.2. (Please refer to example 36 and 37 for procedures of reaction between compound (I-35) and hydrochloric acid to form Hydrochloride salt (II-35))

Example 36

Preparation of 1-(4-(4-(3-trifluoromethylphenyl) piperazin-1-yl)butyl)-1H-benzimidazol (Compound I-36) and 1-(4-(4-(3-trifluoromethylphenyl) piperazin-1-yl)butyl)-1H-benzimidazol Hydrochloride salt (Compound II-36)

Prepare 1-(4-chlorobutyl)-1H-benzimidazol as described in example 35.

1-(4-chlorobutyl)-1H-benzimidazole (7.51 g, 0.036 mol) was dissolved in 100 ml of acetonitrile and added with 3-trifluoromethylphenyl piperazine (6.91 g, 0.03 mol), diisopropyl ethylamine (15.5 g, 0.12 mol), and potassium iodide (5.0 g, 0.03 mol), and then stirred for 10 minutes at room temperature, and allow to react for 10-20 hours under heating and reflux. The solution was then cooled to room temperature, filtered, and the filtrate then concentrated to obtain an oily substance which is purified by chromatographic separation using neutral $Al_2O_3$, and then eluted with dichloromethane/methanol mixture to obtain 7.6 g of the compound (I-36), with a yield of 62.8%.

Dissolve compound (I-36)(6.04 g, 0.015 mol) in 80 mL of ethyl acetate and 8 mL of ethanol. Under ice-water bath cooling, 3 mol of hydrogen chloride/ethyl acetate solution was added dropwise until a reaction solution of pH=3 was obtained; then the resulting solution was heated to 50° C., stirred for 20 min, cooled to crystallize, filtered and dried to obtain 5.9 g of compound (II-36), with a yield of 89.7%. ESI-MS [M+H]$^+$: m/z 403.2.

Example 37

Preparation of 1-(4-(4-(2,3-dichlorophenyl) piperazin-1-yl)butyl)-1H-benzimidazol (I-37) and 1-(4-(4-(2,3-dichlorophenyl) piperazin-1-yl)butyl)-1H-benzimidazol Hydrochloride salt (II-37) (Compound II-37)

Prepare 1-(4-chlorobutyl)-1H-benzimidazol as described in example 35.

1-(4-chlorobutyl)-1H-benzimidazole (7.51 g, 0.036 mol) was dissolved in 100 ml of acetonitrile and added with 2,3-dichloro-phenyl piperazine (6.93 g, 0.03 mol), diisopropyl ethylamine (15.5 g, 0.12 mol), and potassium iodide (5.0 g, 0.03 mol), and then stirred for 10 minutes at room temperature, and allow to react for 10$^-2$0 hours under heating and reflux. The solution was then cooled to room temperature, filtered, and the filtrate then concentrated to obtain an oily substance which is purified by chromatographic separation using neutral $Al_2O_3$, and then eluted with dichloromethane/methanol mixture to obtain 7.5 g of the compound (I-37), with a yield of 62.0%.

Dissolve compound (I-37)(6.05 g, 0.015 mol) in 80 mL of ethyl acetate and 8 mL of ethanol. Under ice-water bath cooling, 3 mol of hydrogen chloride/ethyl acetate solution was added dropwise until a reaction solution of pH=3 was obtained; then the resulting solution was heated to 50° C., stirred for 20 min, cooled to crystallize, filtered and dried to obtain 6.0 g of compound (II-37), with a yield of 90.9%. ESI-MS [M+H]$^+$: m/z 403.1.

Example 38

Preparation of 1-(4-(4-(2-methoxyphenyl) piperazin-1-yl)butyl)-1H-benzimidazol (Compound I-38)

Prepare 1-(4-chlorobutyl)-1H-benzimidazol as described in example 35.

1-(4-chlorobutyl)-1H-benzimidazol (7.51 g, 0.036 mol) was dissolved in 100 ml of acetonitrile and added with 2-methoxyphenyl piperazine (5.77 g, 0.03 mol), diisopropyl ethylamine (15.5 g, 0.12 mol), and potassium iodide (5.0 g, 0.03 mol), and then stirred for 10 minutes at room temperature, and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane/methanol mixture to obtain 7.7 g of the compound (I-38), with a yield of 70.6%. ESI-MS $[M+H]^+$: m/z 365.2. (Please refer to example 36 and 37 for procedures of reaction between compound I-38 and hydrochloric acid to form Hydrochloride salt)

Example 39

Preparation of 6-chloro-1-(4-(4-(3-trifluoromethyl-phenyl) piperazin-1-yl)butyl)-1H-benzimidazole (Compound I-39)

The 2-methylbenzimidazol-1H-(13.2 g, 0.10 mol) was dissolved in 200 mL of 20 wt % sodium hydroxide aqueous solution and then was added with 4-Chloro-bromobutane (34.3 g, 0.20 mol), tetrabutylammonium bromide (1.0 g, 0.003 mol); it is then mixed and stirred for 5 minutes, heated to 60° C. and react for 2 hours under stirring. The reaction solution was cooled to room temperature, and extracted with 100 mL of dichloromethane and the liquid was separated; and 100 mL of dichloromethane was then added to aqueous phase, and then the organic phases were combined and washed with 100 mL of saturated saline solution and the liquid was separated; and the organic phase was evaporated to obtain oily substance. The oily substance was then purified by chromatography separation using neutral $Al_2O_3$ to obtain 13.7 g of 1-(4-chlorobutyl)-2-methyl-1H-benzimidazol, with a yield of 61.5%.

1-(4-chlorobutyl)-2-methyl-1H-benzimidazol (8.02 g, 0.036 mol) was dissolved in 100 ml of acetonitrile and added with 3-trifluoromethylphenyl piperazine (6.91 g, 0.03 mol), diisopropyl ethylamine (15.5 g, 0.12 mol), and potassium iodide (5.0 g, 0.03 mol), and then stirred for 10 minutes at room temperature, and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane/methanol mixture to obtain 8.1 g of the compound (I-39), with a yield of 64.9%. ESI-MS $[M+H]^+$: m/z 417.2. (Please refer to example 36 and 37 for procedures of reaction between compound I-39 and hydrochloric acid to form Hydrochloride salt (II-39))

Example 40

Preparation of 6-fluoro-1-(4-(4-(3-trifluoromethyl-phenyl) piperazin-1-yl)butyl)-1H-benzimidazole (Compound I-40)

The 6-fluoro-1H-benzimidazol (13.2 g, 0.10 mol) was dissolved in 200 mL of 20 wt % sodium hydroxide aqueous solution and then was added with 4-Chloro-bromobutane (34.3 g, 0.20 mol), tetrabutylammonium bromide (1.0 g, 0.003 mol); it is then mixed and stirred for 5 minutes, heated to 60° C. and react for 2 hours under stirring. The oily substance was then purified by chromatography separation using neutral $Al_2O_3$ to obtain 1-(4-chlorobutyl)-6-fluoro-1H-benzimidazole 14.2, with a yield of 62.6%.

1-(4-chlorobutyl)-6-fluoro-1H-benzimidazol (8.16 g, 0.036 mol) was dissolved in 100 ml of acetonitrile and added with 3-trifluoromethylphenyl piperazine (6.91 g, 0.03 mol), diisopropyl ethylamine (15.5 g, 0.12 mol), and potassium iodide (5.0 g, 0.03 mol), and then stirred for 10 minutes at room temperature, and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane/methanol mixture to obtain 8.5 g of the compound (I-40), with a yield of 67.4%. ESI-MS $[M+H]^+$: m/z 421.2. (Please refer to example 36 and 37 for procedures of reaction between compound I-40 and hydrochloric acid to form Hydrochloride salt (II-40))

Example 41

Preparation of 1-(3-(4-phenyl-piperazin-1-yl)propyl)-1H-benzimidazole (Compound I-41)

The substituted 1H-benzimidazol (11.8 g, 0.10 mol) was dissolved in 200 mL of 20 wt % sodium hydroxide aqueous solution and then was added with 3-chloro-bromopropane (31.4 g, 0.20 mol), tetrabutylammonium bromide (1.0 g, 0.003 mol); it is then mixed and stirred for 5 minutes, heated to 60° C. and react for 2 hours under stirring. The reaction solution was cooled to room temperature, and extracted with 100 mL of dichloromethane and the liquid was separated; and 100 mL of dichloromethane was then added to aqueous phase, and then the organic phases were combined and washed with 100 mL of saturated saline solution and the liquid was separated; and the organic phase was evaporated to obtain oily substance. The oily substance was then purified by chromatography separation using neutral $Al_2O_3$ to obtain 12.0 g of 1-(3-chloropropyl)-1H-benzimidazol, with a yield of 62.0%.

1-(3-chloropropyl)-1H-benzimidazol (6.98 g, 0.036 mol) was dissolved in 100 ml of acetonitrile and added with phenyl-piperazine (4.9 g, 0.03 mol), diisopropyl ethylamine (15.5 g, 0.12 mol), and potassium iodide (5.0 g, 0.03 mol), and then stirred for 10 minutes at room temperature, and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane/methanol mixture to obtain 6.1 g of the compound (I-41), with a yield of 63.2%. ESI-MS $[M+H]^+$: m/z 321.2. (Please refer to example 36 and 37 for procedures of reaction between compound I-41 and hydrochloric acid to form Hydrochloride salt II-41)

Example 42

Preparation of 1-(3-(4-(3-fluorophenyl) piperazin-1-yl)propyl)-1H-benzimidazole (Compound I-42)

Prepare 1-(3-chloropropyl)-1H-benzimidazol as described in example 41.

1-(3-chloropropyl)-1H-benzimidazol (6.98 g, 0.036 mol) was dissolved in 100 ml of acetonitrile and added with 3-fluorophenyl piperazine (6.91 g, 0.03 mol), diisopropyl ethylamine (15.5 g, 0.12 mol), and potassium iodide (5.0 g, 0.03 mol), and then stirred for 10 minutes at room temperature, and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane/ methanol mixture to obtain 6.4 g of the compound (I-42), with a yield of 63.1%. ESI-MS $[M+H]^+$: m/z 339.2. (Please refer to example 36 and 37 for procedures of reaction between compound I-42 and hydrochloric acid to form Hydrochloride salt II-42)

Example 43

Preparation of 2-methyl-1-(3-(4-(3-fluorophenyl) piperazin-1-yl)propyl)-1H-benzimidazol (Compound I-43)

The 2-methylbenzimidazol-1H-(13.2 g, 0.10 mol) was dissolved in 200 mL of 20 wt % sodium hydroxide aqueous solution and then was added with 3-chloro-bromopropane (31.4 g, 0.20 mol), tetrabutylammonium bromide (1.0 g, 0.003 mol); it is then mixed and stirred for 5 minutes, heated to 60° C. and react for 2 hours under stirring. The reaction solution was cooled to room temperature, and extracted with 100 mL of dichloromethane and the liquid was separated; and 100 mL of dichloromethane was then added to aqueous phase, and then the organic phases were combined and washed with 100 mL of saturated saline solution and the liquid was separated; and the organic phase was evaporated to obtain oily substance. The oily substance was then purified by chromatography separation using neutral $Al_2O_3$ to obtain 12.9 g of 1-(3-chloropropyl)-2-methyl-1H-benzimidazol, with a yield of 62.1%.

1-(3-chloropropyl)-2-methyl-1H-benzimidazol (7.49 g, 0.036 mol) was dissolved in 100 ml of acetonitrile and added with 3-trifluoromethyl phenylpiperazine (4.9 g, 0.03 mol), diisopropyl ethylamine (15.5 g, 0.12 mol), and potassium iodide (5.0 g, 0.03 mol), and then stirred for 10 minutes at room temperature, and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane/methanol mixture to obtain 6.67 g of the compound (I-43), with a yield of 63.1%. ESI-MS $[M+H]^+$: m/z 353.2. (Please refer to example 36 and 37 for procedures of reaction between compound I-43 and hydrochloric acid to form Hydrochloride salt II-43)

Example 44

Preparation of 1-(4-(4-(3-cyanophenyl) piperazin-1-yl)butyl)-1H-benzimidazole (Compound I-44)

Prepare 1-(4-chlorobutyl)-1H-benzimidazol as described in example 35.

1-(4-chlorobutyl)-1H-benzimidazol (7.51 g, 0.036 mol) was dissolved in 100 ml of acetonitrile and added with 3-cyanophenyl piperazine (5.6 g, 0.03 mol), diisopropyl ethylamine (15.5 g, 0.12 mol), and potassium iodide (5.0 g, 0.03 mol), and then stirred for 10 minutes at room temperature, and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane/methanol mixture to obtain 6.7 g of the compound (I-44), with a yield of 62.4%. ESI-MS $[M+H]^+$: m/z 360.2. (Please refer to example 36 and 37 for procedures of reaction between compound I-44 and hydrochloric acid to form Hydrochloride salt II-44)

Example 45

Preparation of 1-(4-(4-(4-methylphenyl) piperazin-1-yl)butyl)-1H-benzimidazole (Compound I-45)

Prepare 1-(4-chlorobutyl)-1H-benzimidazol as described in example 35.

1-(4-chlorobutyl)-1H-benzimidazol (7.51 g, 0.036 mol) was dissolved in 100 ml of acetonitrile and added with 4-methyl-phenyl piperazine (5.3 g, 0.03 mol), diisopropyl ethylamine (15.5 g, 0.12 mol), and potassium iodide (5.0 g, 0.03 mol), and then stirred for 10 minutes at room temperature, and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane/methanol mixture to obtain 6.4 g of the compound (I-45), with a yield of 60.7%. ESI-MS $[M+H]^+$: m/z 349.2. (Please refer to example 36 and 37 for procedures of reaction between compound I-45 and hydrochloric acid to form Hydrochloride salt II-45)

Example 46

Preparation of 1-(4-(4-(2-furyl) piperazin-1-yl)butyl)-1H-benzimidazole (Compound I-46)

Prepare 1-(4-chlorobutyl)-1H-benzimidazol as described in example 35.

1-(4-chlorobutyl)-1H-benzimidazol (7.51 g, 0.036 mol) was dissolved in 100 ml of acetonitrile and added with 4-(2-furyl) piperazine (4.6 g, 0.03 mol), diisopropyl ethylamine (15.5 g, 0.12 mol), and potassium iodide (5.0 g, 0.03 mol), and then stirred for 10 minutes at room temperature, and allow to react for 20 hours under heating and reflux. The solution was then cooled to room temperature, filtered, and the filtrate then concentrated to obtain an oily substance which is purified by chromatographic separation using neutral $Al_2O_3$, and then eluted with dichloromethane/methanol mixture to obtain 6.0 g of the compound (I-46), with a yield of 61.5%. ESI-MS $[M+H]^+$: m/z 325.2. (Please refer to example 36 and 37 for procedures of reaction between compound I-46 and hydrochloric acid to form Hydrochloride salt II-46)

Example 47

Preparation of 1-(4-(4-(4-pyridyl) piperazin-1-yl) butyl)-1H-benzimidazole (Compound I-47)

Prepare 1-(4-chlorobutyl)-1H-benzimidazol as described in example 35.

1-(4-chlorobutyl)-1H-benzimidazol (7.51 g, 0.036 mol) was dissolved in 100 ml of acetonitrile and added with 4-(4-pyridyl) piperazine (4.9 g, 0.03 mol), diisopropyl ethylamine (15.5 g, 0.12 mol), and potassium iodide (5.0 g, 0.03 mol), and then stirred for 10 minutes at room temperature, and allow to react for 20 hours under heating and reflux. The solution was then cooled to room temperature, filtered, and the filtrate then concentrated to obtain an oily substance which is purified by chromatographic separation using neutral Al$_2$O$_3$, and then eluted with dichloromethane/methanol mixture to obtain 6.3 g of the compound (I-47), with a yield of 62.1%. ESI-MS [M+H]$^+$: m/z 336.2. (Please refer to example 36 and 37 for procedures of reaction between compound I-47 and hydrochloric acid to form Hydrochloride salt II-47)

Example 48

Preparation of 1-(4-(4-(2-pyrimidinyl) piperazin-1-yl)butyl)-1H-benzimidazole (Compound I-48)

Prepare 1-(4-chlorobutyl)-1H-benzimidazol as described in example 35.

1-(4-chlorobutyl)-1H-benzimidazol (7.51 g, 0.036 mol) was dissolved in 100 ml of acetonitrile and added with 4-(2-pyrimidinyl) piperazine (4.9 g, 0.03 mol), diisopropyl ethylamine (15.5 g, 0.12 mol), and potassium iodide (5.0 g, 0.03 mol), and then stirred for 10 minutes at room temperature, and allow to react for 20 hours under heating and reflux. The solution was then cooled to room temperature, filtered, and the filtrate then concentrated to obtain an oily substance which is purified by chromatographic separation using neutral Al$_2$O$_3$, and then eluted with dichloromethane/methanol mixture to obtain 6.1 g of the compound (I-48), with a yield of 60.1%. ESI-MS [M+H]$^+$: m/z 337.2. (Please refer to example 36 and 37 for procedures of reaction between compound I-48 and hydrochloric acid to form Hydrochloride salt II-48)

Example 49

Preparation of 1-(4-(4-(1-cyclohexyl) piperazin-1-yl)butyl)-1H-benzimidazole (Compound I-49)

Prepare 1-(4-chlorobutyl)-1H-benzimidazol as described in example 35.

1-(4-chlorobutyl)-1H-substituted-benzimidazole (0.036 mol) was dissolved in 100 ml of acetonitrile and added with a substituted phenyl piperazine (0.03 mol), diisopropyl ethylamine (15.5 g, 0.12 mol), and potassium iodide (5.0 g, 0.03 mol), and then stirred for 10 minutes at room temperature, and allow to react for $10^{-2}0$ hours under heating and reflux. The solution was then cooled to room temperature, filtered, and the filtrate then concentrated to obtain an oily substance which is purified by chromatographic separation using neutral Al$_2$O$_3$, and then eluted with dichloromethane/methanol mixture to obtain 6.4 g of the compound (I-49), with a yield of 62.9%. ESI-MS [M+H]$^+$: m/z 341.3. (Please refer to example 36 and 37 for procedures of reaction between compound I-49 and hydrochloric acid to form Hydrochloride salt II-49)

Example 50

I-50 1-(4-(4-(1-naphthyl) piperazin-1-yl)butyl)-1H-benzimidazole

Prepare 1-(4-chlorobutyl)-1H-benzimidazol as described in example 35.

1-(4-chlorobutyl)-1H-benzimidazol (7.51 g, 0.036 mol) was dissolved in 100 ml of acetonitrile and added with 4-(1-naphthyl) piperazine (6.4 g, 0.03 mol), diisopropyl ethylamine (15.5 g, 0.12 mol), and potassium iodide (5.0 g, 0.03 mol), and then stirred for 10 minutes at room temperature, and allow to react for 20 hours under heating and reflux. The solution was then cooled to room temperature, filtered, and the filtrate then concentrated to obtain an oily substance which is purified by chromatographic separation using neutral Al$_2$O$_3$, and then eluted with dichloromethane/methanol mixture to obtain 6.8 g of the compound (I-50), with a yield of 59.1%. ESI-MS [M+H]$^+$: m/z 385.2. (Please refer to example 36 and 37 for procedures of reaction between compound I-50 and hydrochloric acid to form Hydrochloride salt II-50)

Example 51

Preparation of 1-(4-(4-(2-quinoxalinyl) piperazin-1-yl)butyl)-1H-benzimidazole (Compound I-51)

Prepare 1-(4-chlorobutyl)-1H-benzimidazol as described in example 35.

1-(4-chlorobutyl)-1H-benzimidazol (7.51 g, 0.036 mol) was dissolved in 100 ml of acetonitrile and added with 4-(2-quinoxaline-yl) piperazine (6.4 g, 0.03 mol), diisopropyl ethylamine (15.5 g, 0.12 mol), and potassium iodide (5.0 g, 0.03 mol), and then stirred for 10 minutes at room temperature, and allow to react for 20 hours under heating and reflux. The solution was then cooled to room temperature, filtered, and the filtrate then concentrated to obtain an oily substance which is purified by chromatographic separation using neutral Al$_2$O$_3$, and then eluted with dichloromethane/methanol mixture to obtain 6.9 g of the compound (I-51), with a yield of 59.6%. ESI-MS [M+H]$^+$: m/z 387.2. (Please refer to example 36 and 37 for procedures of reaction between compound I-51 and hydrochloric acid to form Hydrochloride salt II-51)

Example 52

Preparation of 1-(4-(4-(3-(6-fluorobenzoisoxazolyl)) piperazin-1-yl)butyl)-1H-benzimidazole (Compound I-52)

Prepare 1-(4-chlorobutyl)-1H-benzimidazol as described in example 35.

1-(4-chlorobutyl)-1H-benzimidazol (7.51 g, 0.036 mol) was dissolved in 100 ml of acetonitrile and added with 6-fluoro-3-(piperazin-4-yl)benzisoxazole (6.6 g, 0.05 mol), diisopropyl ethylamine (15.5 g, 0.12 mol), and potassium iodide (5.0 g, 0.03 mol), and allow to react for 15 hours under heating and reflux. The solution was then cooled to room temperature, filtered, and the filtrate then concentrated to obtain an oily substance which is purified by chromatographic separation using neutral Al$_2$O$_3$, and then eluted with dichloromethane to obtain 7.7 g of the compound (I-52), with a yield of 65.5%. ESI-MS [M+H]$^+$: m/z 394.2. (Please refer to example 36 and 37 for procedures of reaction between compound I-52 and hydrochloric acid to form Hydrochloride salt II-52)

Example 53

Preparation of 1-(4-(4-(3-(6-fluorobenzothiazol isothiazolyl)) piperazin-1-yl)butyl)-1H-benzimidazole (Compound I-53)

Prepare 1-(4-chlorobutyl)-1H-benzimidazol as described in example 35.

1-(4-chlorobutyl)-1H-benzimidazol (7.51 g, 0.036 mol) was dissolved in 100 ml of acetonitrile and added with 6-fluoro-3-(piperazin-4-yl)benzisothiazole (7.1 g, 0.05 mol), diisopropyl ethylamine (15.5 g, 0.12 mol), and potassium iodide (5.0 g, 0.03 mol), and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 7.9 g of the compound (I-53), with a yield of 64.6%. ESI-MS [M+H]$^+$: m/z 410.2. (Please refer to example 36 and 37 for procedures of reaction between compound I-53 and hydrochloric acid to form Hydrochloride salt II-53)

Example 54

Preparation of 1-(4-(4-(3-benzo-pyrazol-yl) piperazin-1-yl)butyl)-1H-benzimidazol (Compound I-54)

Prepare 1-(4-chlorobutyl)-1H-benzimidazol as described in example 35.

1-(4-chlorobutyl)-1H-benzimidazol (7.51 g, 0.036 mol) was dissolved in 100 ml of acetonitrile and added with 3-(piperazin-4-yl)benzo pyrazole (6.1 g, 0.05 mol), diisopropyl ethylamine (15.5 g, 0.12 mol), and potassium iodide (5.0 g, 0.03 mol), and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 6.9 g of the compound (I-54), with a yield of 61.5%. ESI-MS [M+H]$^+$: m/z 375.2. (Please refer to example 36 and 37 for procedures of reaction between compound I-54 and hydrochloric acid to form Hydrochloride salt II-54)

Example 55

Preparation of 1-(4-(4-(3-(6-fluorobenzofuran-yl)) piperazin-1-yl)butyl)-1H-benzimidazol (Compound I-55)

Prepare 1-(4-chlorobutyl)-1H-benzimidazol as described in example 35.

1-(4-chlorobutyl)-1H-benzimidazol (7.51 g, 0.036 mol) was dissolved in 100 ml of acetonitrile and added with 6-fluoro-3-(piperazin-4-yl)benzofuran (6.6 g, 0.05 mol), diisopropyl ethylamine (15.5 g, 0.12 mol), and potassium iodide (5.0 g, 0.03 mol), and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 7.5 g of the compound (I-55), with a yield of 63.6%. ESI-MS [M+H]$^+$: m/z 393.2. (Please refer to example 36 and 37 for procedures of reaction between compound I-55 and hydrochloric acid to form Hydrochloride salt II-55)

Example 56

Preparation of 1-(4-(4-(3-(6-fluorobenzisoxazolyl)) piperazin-1-yl)propoxy)-1H-benzimidazole (Compound I-56)

Imidazol-1-hydroxybenzotriazole (0.1 mol) was dissolved in 10 mL of NMP, and a mixture containing 50% wt sodium hydride and solid wax was added in portions, and react for 0.5 hour under stirring. At the same time, dissolve 3-chloro-bromopropane (0.015 mol) in 5 ml of NMP, and add the solution in the mixture solution above, and allow to react under room temperature for 12 hours under stirring. The reaction solution is then poured into 50 ml of water and extracted with ethyl acetate (3×50 mL); then the organic phases are combined and washed with 30 mL of water; Anhydrous magnesium sulfate was then used to dry the organic phase, which was then filtered and evaporated to dryness; the oily substance obtained was then purified by chromatography using neutral $Al_2O_3$ or separated and purified by preparative HPLC to obtain 1-(3-chloropropoxy) benzimidazole with a yield of 75.0%.

1-(3-chloropropoxy)benzimidazole (0.06 mol) was dissolved in 150 mL of acetonitrile. 4-(3-(6-fluoro-benzisoxazolyl))piperidine (0.05 mol), diisopropylethyl amine (0.2 mol), and potassium iodide (0.05 mol) were added thereto. The resulting solution was stirred for 10 minutes at room temperature and react for 15 hours under heating and reflux. The resulting solution was cooled to room temperature, filtered, and the filtrate was concentrated to obtain an oily substance which was purified by chromatographic separation using neutral $Al_2O_3$, and eluted using dichloromethane/methanol to obtain 13.7 g of 1-(4-(4-(3-(6-fluorobenzoisoxazolyl)) piperazin-1-yl)propoxy)-1H-benzimidazol (I-56), with a yield of 69.1%. ESI-MS [M+H]$^+$: m/z 396.2. (Please refer to example 36 and 37 for procedures of reaction between compound I-56 and hydrochloric acid to form Hydrochloride salt II-56)

Example 57

Preparation of 1-(4-(4-(3-trifluoromethylphenyl) piperazin-1-yl)propoxy)-1H-benzimidazole (Compound I-57)

Prepare 1-(3-chloropropoxy)benzimidazole as described in example 56.

1-(3-chloropropoxy)benzimidazole (0.06 mol) was dissolved in 150 mL of acetonitrile. 4-(3-trifluoromethylphenyl)piperidine (0.05 mol), diisopropylethyl amine (0.2 mol), and potassium iodide (0.05 mol) were added thereto. The resulting solution was stirred for 10 minutes at room temperature and react for 15 hours under heating and reflux. The resulting solution was cooled to room temperature, filtered, and the filtrate was concentrated to obtain an oily substance which was purified by chromatographic separation using neutral $Al_2O_3$, and eluted using dichloromethane/methanol to obtain 13.7 g of 1-(4-(4-(3-trifluoromethylphenyl) piperazin-1-yl)propoxy)-1H-benzimidazole (Compound I-57), with a yield of 67.9%. ESI-MS [M+H]$^+$: m/z 405.2. (Please refer to example 36 and 37 for procedures of reaction between compound I-57 and hydrochloric acid to form Hydrochloride salt II-57)

Example 58

Preparation of 1-(4-(4-(3-chlorophenyl) piperazin-1-yl)propoxy)-1H-benzimidazole (Compound I-58)

Prepare 1-(3-chloropropoxy)benzimidazole as described in example 56.

1-(3-chloropropoxy)benzimidazole (0.036 mol) was dissolved in 150 ml of acetonitrile and added with 4-(3-chlorophenyl) piperazine (0.05 mol), diisopropylethyl amine (0.2 mol), and potassium iodide (0.05 mol), and then stirred for 10 minutes at room temperature, and allow to react for 15 hours under heating and reflux. The resulting solution was cooled to room temperature, filtered, and the filtrate was concentrated to obtain an oily substance which was purified by chromatographic separation using neutral $Al_2O_3$, and eluted using dichloromethane/methanol to obtain 12.2 g of 1-(4-(4-(3-chlorophenyl) piperazin-1-yl) propoxy)-1H-benzimidazole (Compound I-58), with a yield of 66.1%. ESI-MS [M+H]$^+$: m/z 371.2. (Please refer to example 36 and 37 for procedures of reaction between compound I-58 and hydrochloric acid to form Hydrochloride salt II-58)

Example 59

Preparation of 6-chloro-1-(4-(4-(3-trifluoromethylphenyl) piperazin-1-yl)butyl)-1H-benzimidazole (Compound I-59)

The 6-fluoro-1H-benzimidazol (15.2 g, 0.10 mol) was dissolved in 200 mL of 20 wt % sodium hydroxide aqueous solution and then was added with 4-Chloro-bromobutane (34.3 g, 0.20 mol), tetrabutylammonium bromide (1.0 g, 0.003 mol); it is then mixed and stirred for 5 minutes, heated to 60° C. and react for 2 hours under stirring. According to procedures after first step in example 36, the resulting solution was then purified by chromatography separation using neutral $Al_2O_3$ to obtain 1-(4-chlorobutyl)-6-chloro-1H-benzimidazol, with a yield of 62.3%.

1-(4-chlorobutyl)-6-chloro-1H-benzimidazol (0.036 mol) was dissolved in 100 ml of acetonitrile and added with 3-trifluoromethylphenyl piperazine (6.91 g, 0.03 mol), diisopropyl ethylamine (15.5 g, 0.12 mol), and potassium iodide (5.0 g, 0.03 mol), and then stirred for 10 minutes at room temperature, and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane/methanol mixture to obtain 8.6 g of the compound (I-59), with a yield of 65.8%. ESI-MS [M+H]$^+$: m/z 437.2. (Please refer to example 36 and 37 for procedures of reaction between compound I-59 and hydrochloric acid to form Hydrochloride salt II-59)

Example 60

Preparation of 6-cyano-1-(4-(4-(3-trifluoromethylphenyl) piperazin-1-yl)butyl)-1H-benzimidazole (Compound I-60)

The 6-cyano-1H-benzimidazol (14.3 g, 0.10 mol) was dissolved in 200 mL of 20 wt % sodium hydroxide aqueous solution and then was added with 4-Chloro-bromobutane (34.3 g, 0.20 mol), tetrabutylammonium bromide (1.0 g, 0.003 mol); it is then mixed and stirred for 5 minutes, heated to 60° C. and react for 2 hours under stirring. According to procedures after first step in example 35, the resulting solution was then purified by chromatography separation using neutral $Al_2O_3$ to obtain 14.7 g of 1-(4-chlorobutyl)-6-cyano-1H-benzimidazol, with a yield of 63.1%.

1-(4-chlorobutyl)-6-cyano-1H-benzimidazol (8.39 g, 0.036 mol) was dissolved in 100 ml of acetonitrile and added with 3-trifluoromethylphenyl piperazine (6.91 g, 0.03 mol), diisopropyl ethylamine (15.5 g, 0.12 mol), and potassium iodide (5.0 g, 0.03 mol), and then stirred for 10 minutes at room temperature, and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane/methanol mixture to obtain 8.6 g of the compound (I-60), with a yield of 66.9%. ESI-MS [M+H]$^+$: m/z 428.2. (Please refer to example 36 and 37 for procedures of reaction between compound I-60 and hydrochloric acid to form Hydrochloride salt II-60)

Example 61

Preparation of 6-methoxycarbonyl-1-(4-(4-(3-trifluoromethylphenyl) piperazin-1-yl)butyl)-1H-benzimidazole (Compound I-61)

The 6-methoxycarbonyl-1H-benzimidazol (17.6 g, 0.10 mol) was dissolved in 200 mL of 20 wt % sodium hydroxide aqueous solution and then was added with 4-Chloro-bromobutane (34.3 g, 0.20 mol), tetrabutylammonium bromide (1.0 g, 0.003 mol); it is then mixed and stirred for 5 minutes, heated to 60° C. and react for 2 hours under stirring. According to procedures after first step in example 35, the resulting solution was then purified by chromatography separation using neutral $Al_2O_3$ to obtain 16.9 g of 1-(4-chlorobutyl)-6-cyano-1H-benzimidazol, with a yield of 63.4%.

1-(4-chlorobutyl)-6-cyano-1H-benzimidazol (9.58 g, 0.036 mol) was dissolved in 100 ml of acetonitrile and added with 3-trifluoromethylphenyl piperazine (6.91 g, 0.03 mol), diisopropyl ethylamine (15.5 g, 0.12 mol), and potassium iodide (5.0 g, 0.03 mol), and then stirred for 10 minutes at room temperature, and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane/methanol mixture to obtain 8.8 g of the compound (I-61), with a yield of 63.7%. ESI-MS [M+H]$^+$: m/z 461.2. (Please refer to example 36 and 37 for procedures of reaction between compound I-61 and hydrochloric acid to form Hydrochloride salt II-61)

Example 62

Preparation of 2-chloro-1-(5-(4-(3-trifluoromethylphenyl) piperazin-1-yl) pentyl)-1H-benzimidazole (Compound I-62)

The 2-Chloro-1H-benzimidazol (15.2 g, 0.10 mol) was dissolved in 200 mL of 20 wt % sodium hydroxide aqueous solution and then was added with Bromo-5-chloro-pentane (36.8 g, 0.20 mol), tetrabutylammonium bromide (1.0 g, 0.003 mol); it is then mixed and stirred for 5 minutes, heated to 60° C. and react for 2 hours under stirring. The reaction solution was cooled to room temperature, and extracted with 100 mL of dichloromethane and the liquid was separated; and 100 mL of dichloromethane was then added to aqueous phase, and then the organic phases were combined and washed with 100 mL of saturated saline solution and the liquid was separated; and the organic phase was evaporated to obtain oily substance. The oily substance was then purified by chromatography separation using neutral $Al_2O_3$ to obtain 16.0 g of 1-(5-chloro-pentyl)-2-chloro-1H-benzimidazol, with a yield of 62.5%.

1-(5-chloro-pentyl)-2-chloro-1H-benzimidazol (9.22 g, 0.036 mol) was dissolved in 100 ml of acetonitrile and added with 3-trifluoromethylphenyl piperazine (6.91 g, 0.03 mol), diisopropyl ethylamine (15.5 g, 0.12 mol), and potassium iodide (5.0 g, 0.03 mol), and then stirred for 10 minutes at room temperature, and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane/methanol mixture to obtain 8.8 g of the compound (I-62), with a yield of 65.2%. ESI-MS $[M+H]^+$: m/z 451.2. (Please refer to example 36 and 37 for procedures of reaction between compound I-62 and hydrochloric acid to form Hydrochloride salt II-62)

Example 63

Preparation of 1-(4-(4-(3-chlorophenyl) piperazin-1-yl)butyl)-1H-benzotriazole (Compound I-63)

The benzotriazole (11.9 g, 0.10 mol) was dissolved in 100 mL of 30 wt % sodium hydroxide aqueous solution and then was added with 4-chloro-bromobutane (34.3 g, 0.20 mol), tetrabutylammonium bromide (0.8 g, 0.0025 mol); it is then mixed and stirred for 5 minutes. Heat slowly to 60° C. and allow to react for 2 hours under stirring. The reaction solution was cooled to room temperature, and extracted with 100 mL of dichloromethane and the liquid was separated; and 100 mL of dichloromethane was then added to aqueous phase, and then the organic phases were combined and washed with 100 mL of saturated saline solution and the liquid was separated; and the organic phase was evaporated to obtain oily substance. The oily substance was then purified by chromatography separation using neutral $Al_2O_3$ to obtain 17.0 g of 1-(4-chloro-butyl)-1H-benzotriazole, with a yield of 81.0%.

1-(4-chlorobutyl)-1H-benzotriazole (7.55 g, 0.036 mol) was dissolved in 100 ml of acetonitrile and added with 3-chlorophenyl piperazine (5.9 g, 0.03 mol), diisopropyl ethylamine (15.5 g, 0.12 mol), and potassium iodide (5.0 g, 0.03 mol), and then stirred for 10 minutes and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 7.8 g of the compound (I-63), with a yield of 70.3%.

Dissolve compound (I-63)(5.55 g, 0.015 mol) in 50 mL of ethyl acetate. Under ice-water bath cooling, 3 mol of hydrogen chloride/ethyl acetate solution was added dropwise until a reaction solution of pH=2 was obtained; then the resulting solution was stirred for 10 min, filtered and dried to obtain 5.4 g of compound (II-2), with a yield of 88.0%. ESI-MS $[M+H]^+$: m/z 370.1.

Example 64

Preparation of 1-(4-(4-(3-fluorophenyl) piperazin-1-yl)butyl)-1H-benzotriazole (Compound I-64)

Prepare 1-(4-chloro-butyl)-1H-benzotriazole as described in example 63.

1-(4-chlorobutyl)-1H-benzotriazole (7.55 g, 0.036 mol) was dissolved in 100 ml of acetonitrile and added with 3-fluorophenyl piperazine (5.4 g, 0.03 mol), diisopropyl ethylamine (15.5 g, 0.12 mol), and potassium iodide (5.0 g, 0.03 mol), and then stir and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 7.3 g of the compound (I-64), with a yield of 68.9%. ESI-MS $[M+H]^+$: m/z 354.2. (Please refer to example 36 and 37 for procedures of reaction between compound I-64 and hydrochloric acid to form Hydrochloride salt-II64)

Example 65

Preparation of 1-(4-(4-(3-trifluoromethylphenyl) piperazin-1-yl)butyl)-1H-benzotriazole (Compound I-65)

1-(4-chlorobutyl)-1H-benzotriazole (7.55 g, 0.036 mol) was dissolved in 100 ml of acetonitrile and added with 3-trifluoromethylphenyl piperazine (6.9 g, 0.03 mol), diisopropyl ethylamine (15.5 g, 0.12 mol), and potassium iodide (5.0 g, 0.03 mol), and then stir and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 7.8 g of the compound (I-65), with a yield of 64.5%.

Dissolve compound (I-65) (6.05 g, 0.015 mol) in 50 mL of ethyl acetate. Under ice-water bath cooling, 3 mol of hydrogen chloride/ethyl acetate solution was added dropwise until a reaction solution of pH=2 was obtained; then the resulting solution was stirred for 10 min, filtered and dried to obtain 5.6 g of compound (II-65), with a yield of 84.8%. ESI-MS $[M+H]^+$: m/z 404.2.

Example 66

Preparation of 6-fluoro-1-(4-(4-(3-trifluoromethylphenyl) piperazin-1-yl)butyl)-1H-benzotriazole (Compound I-66)

The 6-fluoro-1H-benzotriazole (13.7 g, 0.10 mol) was dissolved in 100 mL of 30 wt % sodium hydroxide aqueous solution and then was added with 4-chloro-bromobutane (34.3 g, 0.20 mol), tetrabutylammonium bromide (0.8 g, 0.0025 mol); it is then mixed and stirred for 5 minutes. Heat slowly to 60° C. and allow to react for 2 hours under stirring. According to procedures after first step in example 63, the resulting solution was then purified by chromatography separation using neutral $Al_2O_3$ to obtain 8.9 g of 1-(4-chlorobutyl)-6-fluoro-1H-benzotriazole, with a yield of 39.0%.

1-(4-chlorobutyl)-6-fluoro-1H-benzotriazole (8.2 g, 0.036 mol) was dissolved in 100 ml of acetonitrile and added with a substituted arylpiperazine (0.03 mol), diisopropyl ethylamine (15.5 g, 0.12 mol), and potassium iodide (5.0 g, 0.03 mol), and then stir and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 8.3 g of the compound (I-66), with a yield of 65.7%. ESI-MS $[M+H]^+$: m/z 422.2. (Please refer to example 36 and 37 for procedures of reaction between compound I-66 and hydrochloric acid to form Hydrochloride salt II-66)

Example 67

Preparation of 5,6-dimethyl-1-(4-(4-(3-trifluoromethylphenyl) piperazin-1-yl)butyl)-1H-benzotriazole (I-67)

The 5,6-dimethyl-1H-benzotriazole (14.7 g, 0.10 mol) was dissolved in 100 mL of 30 wt % sodium hydroxide aqueous solution and then was added with 4-chloro-bromobutane (34.3 g, 0.20 mol), tetrabutylammonium bromide (0.8 g, 0.0025 mol); it is then mixed and stirred for 5 minutes. Heat slowly to 60° C. and allow to react for 2 hours under stirring. According to procedures after first step in example 63, the resulting solution was then purified by chromatography separation using neutral $Al_2O_3$ to obtain 17.4 g of 1-(4-chlorobutyl)-5,6-dimethyl-1H-benzotriazole, with a yield of 73.2%.

1-(4-chlorobutyl)-5,6-dimethyl-1H-benzotriazole (8.56 g, 0.036 mol) was dissolved in 100 ml of acetonitrile and added with 3-trifluoromethylphenyl piperazine (6.9 g, 0.03 mol), diisopropyl ethylamine (15.5 g, 0.12 mol), and potassium iodide (5.0 g, 0.03 mol), and then stir and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 9.1 g of the compound (I-67), with a yield of 70.3%. ESI-MS [M+H]$^+$: m/z 432.2. (Please refer to example 36 and 37 for procedures of reaction between compound I-67 and hydrochloric acid to form Hydrochloride salt II-67)

Example 68

Preparation of 6-fluoro-3-(4-(4-(1H-benzotriazol-1-yl)butyl) piperazin-1-yl)benzisoxazole (Compound I-70)

Prepare 1-(4-chloro-butyl)-1H-benzotriazole as described in example 63.

1-(4-chlorobutyl)-1H-benzimidazol (7.55 g, 0.036 mol) was dissolved in 100 ml of acetonitrile and added with 3-(piperazin-1-yl)benzisothiazole (6.58 g, 0.03 mol), diisopropyl ethylamine (15.5 g, 0.12 mol), and potassium iodide (5.0 g, 0.03 mol), and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 8.2 g of the compound (I-68), with a yield of 69.6%.

Dissolve compound (I-68)(5.89 g, 0.015 mol) in 50 mL of ethyl acetate and 5 mL of ethanol. Under ice-water bath cooling, 3 mol of hydrogen chloride/ethyl acetate solution was added dropwise until a reaction solution of pH=2 was obtained; then the resulting solution was stirred for 10 min, filtered and dried to obtain 5.5 g of compound (II-68), with a yield of 85.5%. ESI-MS [M+H]$^+$: m/z 393.2.

Example 69

Preparation of 3-(4-(4-(1H-benzotriazol-1-yl)butyl) piperazin-1-yl)benzisoxazole (Compound I-69)

Prepare 1-(4-chloro-butyl)-1H-benzotriazole as described in example 63.

1-(4-chlorobutyl)-1H-benzimidazol (7.55 g, 0.036 mol) was dissolved in 100 ml of acetonitrile and added with 3-(piperazin-1-yl)benzisothiazole (6.1 g, 0.03 mol), diisopropyl ethylamine (15.5 g, 0.12 mol), and potassium iodide (5.0 g, 0.03 mol), and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 8.0 g of the compound (I-69), with a yield of 70.9%. ESI-MS [M+H]$^+$: m/z 377.2. (Please refer to example 36 and 37 for procedures of reaction between compound I-69 and hydrochloric acid to form Hydrochloride salt II-69)

Example 70

Preparation of 6-fluoro-3-(4-(4-(1H-benzotriazol-1-yl)butyl) piperazin-1-yl)benzisoxazole (Compound I-70)

Prepare 1-(4-chloro-butyl)-1H-benzotriazole as described in example 63.

1-(4-chlorobutyl)-1H-benzimidazol (7.55 g, 0.036 mol) was dissolved in 100 ml of acetonitrile and added with 6-fluoro-3-(piperazin-1-yl)benzisothiazole (6.1 g, 0.03 mol), diisopropyl ethylamine (15.5 g, 0.12 mol), and potassium iodide (5.0 g, 0.03 mol), and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 8.3 g of the compound (I-70), with a yield of 70.0%. ESI-MS [M+H]$^+$: m/z 395.2. (Please refer to example 36 and 37 for procedures of reaction between compound I-70 and hydrochloric acid to form Hydrochloride salt II-70)

Example 71

Preparation of 6-fluoro-3-(4-(3-(1H-benzotriazol-1-yl) propyl)piperazin-1-yl)benzisoxazole (Compound I-71)

The benzotriazole (11.9 g, 0.10 mol) was dissolved in 100 mL of 30 wt % sodium hydroxide aqueous solution and then was added with 3-chloro-bromopropane (30.2 g, 0.20 mol), tetrabutylammonium bromide (0.8 g, 0.0025 mol); it is then mixed and stirred for 5 minutes. Heat slowly to 60° C. and allow to react for 2 hours under stirring. The reaction solution was cooled to room temperature, and extracted with 100 mL of dichloromethane and the liquid was separated; and 100 mL of dichloromethane was then added to aqueous phase, and then the organic phases were combined and washed with 100 mL of saturated saline solution and the liquid was separated; and the organic phase was evaporated to obtain oily substance. The oily substance was then purified by chromatography separation using neutral $Al_2O_3$ to obtain 15.6 g of 1-(3-chloropropyl)-1H-benzotriazole, with a yield of 80.0%.

1-(3-chloropropyl)-1H-benzotriazole (7.02 g, 0.036 mol) was dissolved in 100 ml of acetonitrile and added with 6-fluoro-3-(piperazin-1-yl)benzisothiazole (6.6 g, 0.03 mol), diisopropyl ethylamine (15.5 g, 0.12 mol), and potassium iodide (5.0 g, 0.03 mol), and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 7.9 g of the compound (I-71), with a yield of 69.3%. ESI-MS [M+H]$^+$: m/z 380.2. (Please refer to example 36 and 37 for procedures of reaction between compound I-71 and hydrochloric acid to form Hydrochloride salt II-71)

Example 72

Preparation of 1-(3-(4-(2,3-dichlorophenyl) piperazin-1-yl)propyl)-1H-benzotriazole (Compound I-72)

Prepare 1-(3-chloropropyl)-1H-benzotriazole as described in example 71.

1-(3-chloropropyl)-1H-benzotriazole (7.02 g, 0.036 mol) was dissolved in 100 ml of acetonitrile and added with 2,3-dichlorophenyl piperazine (6.9 g, 0.03 mol), diisopropyl ethylamine (15.5 g, 0.12 mol), and potassium iodide (5.0 g, 0.03 mol), and then stir and allow to react for $10^{-2}0$ hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 8.2 g of the compound (I-72), with a yield of 70.2%. ESI-MS [M+H]$^+$: m/z 389.1. (Please refer to example 36 and 37 for procedures of reaction between compound I-72 and hydrochloric acid to form Hydrochloride salt II-72)

Example 73

Preparation of 1-(3-(4-(3-methylphenyl) piperazin-1-yl)propyl)-1H-benzotriazole (Compound I-73)

Prepare 1-(3-chloropropyl)-1H-benzotriazole as described in example 71.

1-(3-chloropropyl)-1H-benzotriazole (7.02 g, 0.036 mol) was dissolved in 100 ml of acetonitrile and added with 3-methylphenyl piperazine (5.3 g, 0.03 mol), diisopropyl ethylamine (15.5 g, 0.12 mol), and potassium iodide (5.0 g, 0.03 mol), and then stir and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 7.5 g of the compound (I-11), with a yield of 74.6%. ESI-MS [M+H]$^+$: m/z 335.2. (Please refer to example 36 and 37 for procedures of reaction between compound I-73 and hydrochloric acid to form Hydrochloride salt II-73)

Example 74

Preparation of 1-(4-(4-(3-cyanophenyl) piperazin-1-yl)butyl)-1H-benzotriazole (Compound I-74)

Prepare 1-(4-chloro-butyl)-1H-benzotriazole as described in example 63.

1-(4-chlorobutyl)-1H-benzotriazole (7.55 g, 0.036 mol) was dissolved in 100 ml of acetonitrile and added with 3-cyanophenyl piperazine (5.6 g, 0.03 mol), diisopropyl ethylamine (15.5 g, 0.12 mol), and potassium iodide (5.0 g, 0.03 mol), and then stir and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 7.6 g of the compound (I-74), with a yield of 70.5%. ESI-MS [M+H]$^+$: m/z 360.2. (Please refer to example 36 and 37 for procedures of reaction between compound I-74 and hydrochloric acid to form Hydrochloride salt II-74)

Example 75

Preparation of 1-(5-(4-(3-trifluoromethylphenyl) piperazin-1-yl) pentyl)-1H-benzimidazole (Compound I-62)

The benzotriazole (11.9 g, 0.10 mol) was dissolved in 100 mL of 30 wt % sodium hydroxide aqueous solution and then was added with bromo-5-chloro-pentane (36.8 g, 0.20 mol), tetrabutylammonium bromide (0.8 g, 0.0025 mol); it is then mixed and stirred for 5 minutes. Heat slowly to 60° C. and allow to react for 2 hours under stirring. The reaction solution was cooled to room temperature, and extracted with 100 mL of dichloromethane and the liquid was separated; and 100 mL of dichloromethane was then added to aqueous phase, and then the organic phases were combined and washed with 100 mL of saturated saline solution and the liquid was separated; and the organic phase was evaporated to obtain oily substance. The oily substance was then purified by chromatography separation using neutral $Al_2O_3$ to obtain 15.8 g of 1-(5-chloro-pentyl)-1H-benzotriazole, with a yield of 71.0%.

1-(5-chloro-pentyl)-1H-benzotriazole (8.0 g, 0.036 mol) was dissolved in 100 ml of acetonitrile and added with 3-trifluoromethylphenyl piperazine (6.9 g, 0.03 mol), diisopropyl ethylamine (15.5 g, 0.12 mol), and potassium iodide (5.0 g, 0.03 mol), and then stir and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 7.7 g of the compound (I-75), with a yield of 61.5%. ESI-MS [M+H]$^+$: m/z 417.2. (Please refer to example 36 and 37 for procedures of reaction between compound I-75 and hydrochloric acid to form Hydrochloride salt II-75)

Example 76

Preparation of 1-(4-(4-(2-furyl) piperazin-1-yl)butyl)-1H-benzotriazole (Compound I-76)

Prepare 1-(4-chloro-butyl)-1H-benzotriazole as described in example 63.

1-(4-chlorobutyl)-1H-benzotriazole (7.55 g, 0.036 mol) was dissolved in 100 ml of acetonitrile and added with 4-(2-furyl) piperazine (4.6 g, 0.03 mol), diisopropyl ethylamine (15.5 g, 0.12 mol), and potassium iodide (5.0 g, 0.03 mol), and then stir and allow to react for 20 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 7.0 g of the compound (I-76), with a yield of 71.3%. ESI-MS [M+H]$^+$: m/z 325.2. (Please refer to example 36 and 37 for procedures of reaction between compound I-76 and hydrochloric acid to form Hydrochloride salt II-76)

Example 77

Preparation of 1-(4-(4-(4-pyridyl) piperazin-1-yl) butyl)-1H-benzotriazole (Compound I-77)

Prepare 1-(4-chloro-butyl)-1H-benzotriazole as described in example 63.

1-(4-chlorobutyl)-1H-benzotriazole (7.55 g, 0.036 mol) was dissolved in 100 ml of acetonitrile and added with 4-(4-pyridyl) piperazine (4.9 g, 0.03 mol), diisopropyl ethylamine (15.5 g, 0.12 mol), and potassium iodide (5.0 g, 0.03 mol), and then stir and allow to react for 20 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 6.6 g of the compound (I-77), with a yield of 65.3%. ESI-MS [M+H]$^+$: m/z 336.2. (Please refer to example 36 and 37 for procedures of reaction between compound I-77 and hydrochloric acid to form Hydrochloride salt II-77)

Example 78

Preparation of 1-(4-(4-cyclohexyl-piperazin-1-yl) butyl)-1H-benzotriazole (Compound I-78)

Prepare 1-(4-chloro-butyl)-1H-benzotriazole as described in example 63.

1-(4-chlorobutyl)-1H-benzotriazole (7.55 g, 0.036 mol) was dissolved in 100 ml of acetonitrile and added with 4-(1-cyclohexyl-yl) piperazine (5.1 g, 0.03 mol), diisopropyl ethylamine (15.5 g, 0.12 mol), and potassium iodide (5.0 g, 0.03 mol), and then stir and allow to react for 20 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 6.5 g of the compound (I-78), with a yield of 63.7%. ESI-MS [M+H]$^+$: m/z 341.2. (Please refer to example 36 and 37 for procedures of reaction between compound I-78 and hydrochloric acid to form Hydrochloride salt II-78)

Example 79

Preparation of 1-(4-(4-(1-naphthyl) piperazin-1-yl) butyl)-1H-benzotriazole (Compound I-79)

Prepare 1-(4-chloro-butyl)-1H-benzotriazole as described in example 63.

1-(4-chlorobutyl)-1H-benzotriazole (7.55 g, 0.036 mol) was dissolved in 100 ml of acetonitrile and added with 4-(1-naphthyl) piperazine (6.4 g, 0.03 mol), diisopropyl ethylamine (15.5 g, 0.12 mol), and potassium iodide (5.0 g, 0.03 mol), and then stirred, and allow to react for 20 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 6.9 g of the compound (I-79), with a yield of 60.1%. ESI-MS [M+H]$^+$: m/z 385.2. (Please refer to example 36 and 37 for procedures of reaction between compound I-79 and hydrochloric acid to form Hydrochloride salt II-79)

Example 80

Preparation of 1-(4-(4-(2-quinoxalinyl) piperazin-1-yl)butyl)-1H-benzotriazole (Compound I-80)

Prepare 1-(4-chloro-butyl)-1H-benzotriazole as described in example 63.

1-(4-chlorobutyl)-1H-benzotriazole (7.55 g, 0.036 mol) was dissolved in 100 ml of acetonitrile and added with 4-(2-quinoxaline-yl) piperazine (6.4 g, 0.03 mol), diisopropyl ethylamine (15.5 g, 0.12 mol), and potassium iodide (5.0 g, 0.03 mol), and then stirred, and allow to react for 20 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 7.3 g of the compound (I-80), with a yield of 62.7%. ESI-MS [M+H]$^+$: m/z 387.2. (Please refer to example 36 and 37 for procedures of reaction between compound I-80 and hydrochloric acid to form Hydrochloride salt II-80)

Example 81

Preparation of 1-(4-(4-(3-(6-fluoro-benzisothiazolyl)) piperazin-1-yl)butyl)-1H-benzotriazole (Compound I-81)

Prepare 1-(4-chloro-butyl)-1H-benzotriazole as described in example 63.

1-(4-chlorobutyl)-1H-benzimidazol (7.55 g, 0.036 mol) was dissolved in 100 ml of acetonitrile and added with 6-fluoro-3-(piperazin-4-yl)benzisothiazole (6.6 g, 0.05 mol), diisopropyl ethylamine (15.5 g, 0.12 mol), and potassium iodide (5.0 g, 0.03 mol), and allow to react for 20 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 8.2 g of the compound (I-81), with a yield of 66.5%. ESI-MS [M+H]$^+$: m/z 410.2. (Please refer to example 36 and 37 for procedures of reaction between compound I-81 and hydrochloric acid to form Hydrochloride salt II-81)

Example 82

Preparation of 1-(3-(4-(3-(6-fluoro-benzofuran-yl) piperazin-1-yl)propyl)-1H-benzotriazole (Compound I-82)

Prepare 1-(3-chloropropyl)-1H-benzotriazole as described in example 71.

1-(3-chloropropyl)-1H-benzotriazole (7.55 g, 0.036 mol) was dissolved in 100 ml of acetonitrile and added with 6-fluoro-3-(piperazin-4-yl)benzofuran (6.6 g, 0.05 mol), diisopropyl ethylamine (15.5 g, 0.12 mol), and potassium iodide (5.0 g, 0.03 mol), and then stir, and allow to react for 20 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 7.9 g of the compound (I-82), with a yield of 69.1%. ESI-MS [M+H]$^+$: m/z 379.2. (Please refer to example 36 and 37 for procedures of reaction between compound I-82 and hydrochloric acid to form Hydrochloride salt II-82)

Example 83

Preparation of 6-chloro-1-(4-(4-(3-trifluoromethyl-phenyl) piperazin-1-yl)butyl)-1H-benzotriazole (Compound I-83)

The 6-chloro-benzotriazole (15.3 g, 0.10 mol) was dissolved in 100 mL of 30 wt % sodium hydroxide aqueous solution and then was added with 4-chloro-bromobutane (34.3 g, 0.20 mol), tetrabutylammonium bromide (0.8 g, 0.0025 mol); it is then mixed and stirred for 5 minutes. Heat slowly to 60° C. and allow to react for 2 hours under stirring. The reaction solution was cooled to room temperature, and extracted with 100 mL of dichloromethane and the liquid was separated; and 100 mL of dichloromethane was then added to aqueous phase, and then the organic phases were combined and washed with 100 mL of saturated saline solution and the liquid was separated; and the organic phase was evaporated to obtain oily substance. The oily substance was then purified by chromatography separation using neutral $Al_2O_3$ to obtain 19.2 g of 6-chloro-1-(4-chlorobutyl)-1H-benzotriazole, with a yield of 79.0%.

6-chloro-1-(4-chlorobutyl)-1H-benzotriazole (8.75 g, 0.036 mol) was dissolved in 100 ml of acetonitrile and added with 3-trifluoromethylphenyl piperazine (6.9 g, 0.03 mol), diisopropyl ethylamine (15.5 g, 0.12 mol), and potassium iodide (5.0 g, 0.03 mol), and then stir, and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 8.5 g of the compound (I-83), with a yield of 64.7%. ESI-MS $[M+H]^+$: m/z 437.2. (Please refer to example 36 and 37 for procedures of reaction between compound I-83 and hydrochloric acid to form Hydrochloride salt II-83)

Example 84

Preparation of 6-cyano-1-(4-(4-(3-trifluoromethylphenyl) piperazin-1-yl)butyl)-1H-benzotriazole (Compound I-84)

The 6-cyano-benzotriazole (14.4 g, 0.10 mol) was dissolved in 100 mL of 30 wt % sodium hydroxide aqueous solution and then was added with 4-Chloro-bromobutane (34.3 g, 0.20 mol), tetrabutylammonium bromide (0.8 g, 0.0025 mol); it is then mixed and stirred for 5 minutes. Heat slowly to 60° C. and allow to react for 2 hours under stirring. The reaction solution was cooled to room temperature, and extracted with 100 mL of dichloromethane and the liquid was separated; and 100 mL of dichloromethane was then added to aqueous phase, and then the organic phases were combined and washed with 100 mL of saturated saline solution and the liquid was separated; and the organic phase was evaporated to obtain oily substance. The oily substance was then purified by chromatography separation using neutral $Al_2O_3$ and eluted using dichloromethane to obtain 17.8 g of 6-cyano-1-(4-chloro-butyl)-1H-benzotriazole, with a yield of 76.0%.

6-cyano-1-(4-chloro-butyl)-1H-benzotriazole (8.42 g, 0.036 mol) was dissolved in 100 ml of acetonitrile and added with 3-trifluoromethylphenyl piperazine (6.9 g, 0.03 mol), diisopropyl ethylamine (15.5 g, 0.12 mol), and potassium iodide (5.0 g, 0.03 mol), and then stir, and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 8.5 g of the compound (I-84), with a yield of 66.4%. ESI-MS $[M+H]^+$: m/z 428.2. (Please refer to example 36 and 37 for procedures of reaction between compound I-84 and hydrochloric acid to form Hydrochloride salt II-84)

Example 85

Preparation of 6-methoxycarbonyl-1-(4-(4-(3-trifluoromethylphenyl) piperazin-1-yl)butyl)-1H-benzotriazole (Compound I-85)

The 6-methoxycarbonyl-benzotriazole (17.7 g, 0.10 mol) was dissolved in 100 mL of 30 wt % sodium hydroxide aqueous solution and then was added with 4-Chloro-bromobutane (34.3 g, 0.20 mol), tetrabutylammonium bromide (0.8 g, 0.0025 mol); it is then mixed and stirred for 5 minutes. Heat slowly to 60° C. and allow to react for 2 hours under stirring. The reaction solution was cooled to room temperature, and extracted with 100 mL of dichloromethane and the liquid was separated; and 100 mL of dichloromethane was then added to aqueous phase, and then the organic phases were combined and washed with 100 mL of saturated saline solution and the liquid was separated; and the organic phase was evaporated to obtain oily substance. The oily substance was then purified by chromatography separation using neutral $Al_2O_3$ and eluted by dichloromethane to obtain 19.5 g of 6-methoxy-1-(4-chlorobutyl)-1H-benzotriazole, with a yield of 73.0%.

6-methoxy-1-(4-chlorobutyl)-1H-benzotriazole (9.61 g, 0.036 mol) was dissolved in 100 ml of acetonitrile and added with 3-trifluoromethylphenyl piperazine (6.9 g, 0.03 mol), diisopropyl ethylamine (15.5 g, 0.12 mol), and potassium iodide (5.0 g, 0.03 mol), and then stir, and allow to react for 15 hours under heating and reflux. The solution was then cooled to room temperature, filtered, and the filtrate then concentrated to obtain an oily substance which is purified by chromatographic separation using neutral $Al_2O_3$, and then eluted with dichloromethane to obtain 8.8 g of the compound (I-85), with a yield of 63.4%. ESI-MS $[M+H]^+$: m/z 461.2. (Please refer to example 36 and 37 for procedures of reaction between compound I-85 and hydrochloric acid to form Hydrochloride salt II-85)

Example 86

Preparation of 1-(4-(4-(3-(6-fluoro-benzisoxazolyl) piperazin-1-yl)propoxy)-1H-benzotriazole (Compound I-86)

1-hydroxybenzotriazole (0.01 mol) was dissolved in 10 mL of NMP, and a mixture containing 50% wt sodium hydride and solid wax was added in portions, and react for 0.5 hour under stirring. At the same time, dissolve 3-chlorobromopropane (0.015 mol) in 5 ml of NMP, and add the solution in the mixture solution above, and allow to react under room temperature for 12 hours under stirring. The reaction solution is then poured into 50 ml of water and extracted with ethyl acetate (3×50 mL); then the organic phases are combined and washed with 30 mL of water; Anhydrous magnesium sulfate was then used to dry the organic phase, which was then filtered and evaporated to dryness; the oily substance obtained was then purified by chromatography using neutral $Al_2O_3$ or separated and purified by preparative HPLC to obtain 1-(3-chloropropoxy) benzimidazole with a yield of 75.0%.

1-(3-chloropropoxy)benzotriazole (0.06 mol) was dissolved in 150 mL of acetonitrile. 4-(3-(6-fluoro-benzisoxazolyl))piperidine (0.05 mol), diisopropylethyl amine (0.2 mol), and potassium iodide (0.05 mol) were added thereto.

The resulting solution was stirred for 10 minutes at room temperature and react for 15 hours under heating and reflux. The resulting solution was cooled to room temperature, filtered, and the filtrate was concentrated to obtain an oily substance which was purified by chromatographic separation using neutral $Al_2O_3$, and eluted using dichloromethane/methanol to obtain 13.4 g of 1-(4-(4-(3-(6-fluoro-benzisoxazole-yl) piperazin-1-yl)propoxy)-1H-benzotriazole (I-86), with a yield of 67.6%. ESI-MS $[M+H]^+$: m/z 396.2. (Please refer to example 63 and 65 for procedures of reaction between compound I-86 and hydrochloric acid to form Hydrochloride salt II-86)

Example 87

Preparation of 6-fluoro-1-(4-(4-(3-(6-fluoro-benzisothiazolyl)piperazin-1-yl) propoxy)-1H-benzotriazole (Compound I-87)

6-fluoro-1-hydroxybenzotriazole (0.01 mol) was dissolved in 10 mL of NMP, and a mixture containing 50% wt sodium hydride and solid wax was added in portions, and react for 0.5 hour under stirring. At the same time, dissolve 3-chloro-bromopropane (0.015 mol) in 5 ml of NMP, and add the solution in the mixture solution above, and allow to react under room temperature for 12 hours under stirring. The reaction solution is then poured into 50 ml of water and extracted with ethyl acetate (3×50 mL); then the organic phases are combined and washed with 30 mL of water; Anhydrous magnesium sulfate was then used to dry the organic phase, which was then filtered and evaporated to dryness; the oily substance obtained was then purified by chromatography using neutral $Al_2O_3$ or separated and purified by preparative HPLC to obtain 6-fluoro-1-(3-chloropropoxy)benzotriazole with a yield of 75.0%.

6-fluoro-1-(3-chloropropoxy)benzotriazole (0.06 mol) was dissolved in 150 mL of acetonitrile. 4-(3-(6-fluoro-benzisothiazol-yl)) piperazine (0.05 mol), diisopropylethyl amine (0.2 mol), and potassium iodide (0.05 mol) were added thereto. The resulting solution was stirred for 10 minutes at room temperature and react for 15 hours under heating and reflux. The resulting solution was cooled to room temperature, filtered, and the filtrate was concentrated to obtain an oily substance which was purified by chromatographic separation using neutral $Al_2O_3$, and eluted using dichloromethane/methanol to obtain 14.1 g of 6-fluoro-1-(4-(4-(3-(6-fluoro-benzisothiazole-yl) piperazin-1-yl) propoxy)-1H-benzotriazole (I-87), with a yield of 65.6%. ESI-MS $[M+H]^+$: m/z 430.1. (Please refer to example 63 and 65 for procedures of reaction between compound I-87 and hydrochloric acid to form Hydrochloride salt II-87)

Example 88

Compound II-1 to II-87 have Vascular Smooth Muscle Relaxant Effect Against Spasmogens Agents Contraction in Rabbits 1. Study Animal:
Rabbits of either sex, weighing 2.0-3.0 kg, provided by the Experimental Animal Center of China Medical University.

2. Drugs and Reagents
Compound II-1 to II-87, i.e., the compounds I-1 to I-87 hydrochloride, were prepared using the method of an embodiment, and were used in the following test;
NaCl: Purchased from Tianjin Damao Chemical Reagent Factory, batch No.: 20120413;
KCl: Purchased from Tianjin Damao Chemical Reagent Factory, batch No.: 20111123;
$MgSO_4$: Purchased from Tianjin Damao Chemical Reagent Factory, batch No.: 20101029;
$CaCl_2$: Purchased from Tianjin Damao Chemical Reagent Factory, batch No.: 20110314;
$NaHCO_3$: Purchased from Tianjin Damao Chemical Reagent Factory, batch No.: 20120507;
Glucose: Purchased from Tianjin Damao Chemical Reagent Factory, batch No.: 20120512;
$KH_2PO_4$: Purchased from Tianjin Damao Chemical Reagent Factory, batch No.: 20110928;
NaCl injection: Purchased from Shenyang Zhiying Pharmaceutical Co. Ltd., batch number: 12021001;
Epinephrine Hydrochloride Injection: 1 mg/1 ml, purchased from GRANDPHARMA (CHINA) CO. LTD., batch number: 120105;
Norepinephrine Bitartrate Injection, 2 mg/1 ml, purchased from GRANDPHARMA (CHINA) CO. LTD., batch number: 120304;

3. Instruments:
HSS-1(B) thermostatic bath: Chengdu Instrument Factory;
RM6240B Multi-channel physiological signal acquisition and processing system: Chengdu Instrument Factory;
JZJ01 muscle tension transducer: Chengdu Instrument Factory;
YPJ01 pressure transducer: Chengdu Instrument Factory;
TG-328A Photoelectric Analytical Balance: Shanghai Balance Instrument;
T-500 electronic balance: G&G Measurement Plant;
Micropipette: Shanghai Rong Tai Biochemical Engineering Co., Ltd.
Electric heated thermstatic water bath: Tianjin Taisite Instrument Co., LTD.

4. Preparation of Nutrient Solution
Krebs-Henseleit (K—H) physiological solution: NaCl 6.92 (concentration units), KCl 0.35, $MgSO_4$ 0.29, $KH_2PO_4$ 0.16, $CaCl_2$ 0.28, $NaHCO_3$ 2.1, glucose 2.0 (g/L), pH 7.2.
Potassium solution: Remove NaCl and add in an equivalent mole amount of KCl to formulate a modified K—H solution, containing $K^+$ 60 mmol/L
Calcium-free K—H solution: Remove $CaCl_2$ from K—H solution, add an equal number of moles of KCl, and add $EDTA^{-2}Na^+$ 0.1 mmol/L, while the other components remain unchanged.
Calcium-free hyperkalemia solution: Remove $CaCl_2$ from hyperkalemia solution, add an equal number of moles of KCl, and add $EDTA^{-2}Na^+$ 0.1 mmol/L, while the other components remain unchanged.
Preparation of compound II-1 to II-87 solutions: Weigh a certain quality compound samples and dilute to concentrations ($10^{-10}$~$10^{-3}$ mol/L) with distilled water, standby.

5. Preparation of Rabbit Vascular Smooth Muscle Specimens
Cut the chest open quickly after stunning, strip out the descending aorta, then after removing the surrounding connective tissue and adipose tissue (if performed serotonin receptor antagonist experiments, endothelial cells should be removed using a smooth stainless steel bars), cut the vessels into 3-5 mm vascular ring, then pass the steel hook through the blood vessel ring, with one end is fixed to the vent hook and the other end connected to the tension transducer, then place the specimens into bath tube containing 20 mL of nutrient solution, and record tension change by tension transducer. Maintain tube temperature at 37±0.5° C., and pass bubbles (95% $O_2$+5% $CO_2$) into the solution as a speed of 1-2 bubbles/minute. Place an initial load of 1.5 g on the rings, and change nutrient every 20 minutes, then balance for 2 hours and start test after baseline readings are stabilized.

6. Test and Results 6.1 Compound II-1 to II-87 have Vascular Smooth Muscle Relaxant Effect Against Adrenaline Contraction in Rabbits After tension readings are stabilized, record a certain length of tension curve, and add spasmogens agent AD ($10^{-5}$ mol/L) to induce contraction; if a maximum contract is achieved, wash the specimens thoroughly, and change K—H solution every 20 minutes, and then balance for 60 minutes; after baseline readings are stabilized, induce contract with spasmogens agent again. When the maximum contract in the later induction is consistent with the former induction, add compound II-1 to II-34 solutions ($1\times10^{-10}$ to $1\times10^{-3}$ mol/L), II-35 to II-87 solutions ($1\times10^{-8}$-$1\times10^{-3}$ mol/L), and record the curves. Draw a dose-response curve using maximum relaxation response as 100%, relaxation percentage as ordinate and negative logarithms of the each concentration as abscissa. Wherein, compound II-36, II-37, II-65, II-63 and II-68 showed most significant relaxation effects as shown in FIGS. 1, 2, 10, 11 and 12.

As shown in FIGS. 1 and 2, compound II-36 and 37 have relaxant effect against contraction induced by AD, and the effect is dose-dependent to a certain level. And the –log $EC_{50}$ of compound II-36 is 5.73±0.03 compared to 6.01±0.05 of compound II-37.

As shown in FIG. 10, compound II-65 has relaxant effect against contraction induced by AD, and the effect is dose-dependent to a certain level. And the –log $EC_{50}$ of compound II-65 is 6.19±0.03; similarly, as shown in FIG. 11, compound II-63 has relaxant effect against contraction induced by AD, and the effect is dose-dependent to a certain level. And the –log $EC_{50}$ of compound II-65 is 6.01±0.02; also, as shown in FIG. 12, compound II-68 has relaxant effect against contraction induced by AD, and the effect is dose-dependent to a certain level. And the –log $EC_{50}$ of compound II-65 is 8.07±0.06;

The relaxant effect of compound II-1 to II-87 are shown in Table 1.

TABLE 1

Relaxant Effect of the Compounds on In Vitro Vascular Smooth Muscle of Rabbits Contraction induced by AD

| Compound | $-logEC_{50}$ |
| --- | --- |
| II-1 | 5.03 ± 0.02 |
| II-2 | 5.16 ± 0.03 |
| II-3 | 6.21 ± 0.04 |
| II-4 | 6.36 ± 0.03 |
| II-5 | 4.89 ± 0.02 |
| II-6 | 4.76 ± 0.03 |
| II-7 | 5.31 ± 0.04 |
| II-8 | 4.86 ± 0.03 |
| II-9 | 4.79 ± 0.02 |
| II-10 | 5.56 ± 0.05 |
| II-11 | 5.31 ± 0.06 |
| II-12 | 5.45 ± 0.04 |
| II-13 | 5.34 ± 0.03 |
| II-14 | 5.61 ± 0.05 |
| II-15 | 5.42 ± 0.04 |
| II-16 | 5.38 ± 0.03 |
| II-17 | 5.23 ± 0.05 |
| II-18 | 5.56 ± 0.04 |
| II-19 | 6.11 ± 0.07 |
| II-20 | 5.92 ± 0.05 |
| II-21 | 5.96 ± 0.04 |
| II-22 | 5.53 ± 0.07 |
| II-23 | 5.23 ± 0.06 |
| II-24 | 4.03 ± 0.05 |
| II-25 | 4.26 ± 0.04 |
| II-26 | 4.01 ± 0.03 |
| II-27 | 4.13 ± 0.05 |
| II-28 | 4.26 ± 0.06 |
| II-29 | 4.43 ± 0.05 |
| II-30 | 4.86 ± 0.04 |
| II-31 | 4.72 ± 0.03 |
| II-32 | 4.39 ± 0.05 |
| II-33 | 4.22 ± 0.06 |
| II-34 | 4.83 ± 0.05 |
| II-35 | 5.03 ± 0.04 |
| II-36 | 5.73 ± 0.03 |
| II-37 | 6.01 ± 0.05 |
| II-38 | 4.96 ± 0.03 |
| II-39 | 4.78 ± 0.04 |
| II-40 | 4.63 ± 0.06 |
| II-41 | 4.29 ± 0.05 |
| II-42 | 4.71 ± 0.04 |
| II-43 | 4.37 ± 0.03 |
| II-44 | 4.26 ± 0.05 |
| II-45 | 4.05 ± 0.04 |
| II-46 | 4.35 ± 0.06 |
| II-47 | 4.41 ± 0.05 |
| II-48 | 4.22 ± 0.04 |
| II-49 | 4.47 ± 0.04 |
| II-50 | 4.29 ± 0.03 |
| II-51 | 4.53 ± 0.03 |
| II-52 | 4.86 ± 0.06 |
| II-53 | 4.18 ± 0.04 |
| II-54 | 4.23 ± 0.05 |
| II-55 | 4.05 ± 0.03 |
| II-56 | 4.55 ± 0.04 |
| II-57 | 4.72 ± 0.03 |
| II-58 | 4.52 ± 0.04 |
| II-59 | 4.79 ± 0.05 |
| II-60 | 4.19 ± 0.04 |
| II-61 | 4.31 ± 0.04 |
| II-62 | 3.99 ± 0.03 |
| II-63 | 6.01 ± 0.02 |
| II-64 | 5.52 ± 0.03 |
| II-65 | 6.19 ± 0.03 |
| II-66 | 5.41 ± 0.03 |
| II-67 | 4.39 ± 0.04 |
| II-68 | 8.07 ± 0.06 |
| II-69 | 4.89 ± 0.05 |
| II-70 | 5.31 ± 0.04 |
| II-71 | 5.56 ± 0.03 |
| II-72 | 5.72 ± 0.05 |
| II-73 | 5.47 ± 0.04 |
| II-74 | 4.51 ± 0.05 |
| II-75 | 4.39 ± 0.04 |
| II-76 | 4.45 ± 0.04 |
| II-77 | 4.15 ± 0.03 |
| II-78 | 4.26 ± 0.06 |
| II-79 | 3.88 ± 0.04 |
| II-80 | 3.83 ± 0.05 |
| II-81 | 4.05 ± 0.03 |
| II-82 | 4.52 ± 0.03 |
| II-83 | 5.21 ± 0.04 |
| II-84 | 4.01 ± 0.04 |
| II-85 | 4.26 ± 0.03 |
| II-86 | 4.88 ± 0.04 |
| II-87 | 4.28 ± 0.05 |

6.2 Compound II-1 to ii-34 have Relaxant Effect on In Vitro Vascular Smooth Muscle Against Contraction Induced by Spasmogens Agents AD in Rabbits After tension readings are stabilized, record a certain length of tension curve, and add Adrenaline hydrochloride ($10^{-5}$ mol/L) to induce contraction; if a maximum contract is achieved, wash the specimens thoroughly, and change K—H solution every 20 minutes, and then balance for 60 minutes; after baseline readings are stabilized, induce contract with bitartrate noradrenaline (NA) again. When the maximum contract in the later induction is consistent with the former induction, add compound II-1 to II-34 solutions ($1\times10^{-10}$ to $1\times10^{-3}$ mol/L), and record the curves. The relaxant effect of compound II-1 to II-34 are shown in Table 2.

TABLE 2

Compound II-1 to II-34 have relaxant effect a on in-vitro vascular smooth muscle against contraction induced by AD in rabbits

| Compound | $-\log EC_{50}$ |
|---|---|
| II-1 | 5.11 ± 0.02 |
| II-2 | 5.27 ± 0.03 |
| II-3 | 6.32 ± 0.04 |
| II-4 | 6.45 ± 0.03 |
| II-5 | 4.67 ± 0.02 |
| II-6 | 4.55 ± 0.03 |
| II-7 | 5.21 ± 0.04 |
| II-8 | 4.77 ± 0.03 |
| II-9 | 4.53 ± 0.02 |
| II-10 | 5.36 ± 0.05 |
| II-11 | 5.15 ± 0.06 |
| II-12 | 5.26 ± 0.04 |
| II-13 | 5.04 ± 0.03 |
| II-14 | 5.73 ± 0.05 |
| II-15 | 5.22 ± 0.04 |
| II-16 | 5.35 ± 0.03 |
| II-17 | 5.31 ± 0.05 |
| II-18 | 5.73 ± 0.04 |
| II-19 | 6.07 ± 0.04 |
| II-20 | 5.81 ± 0.03 |
| II-21 | 5.73 ± 0.04 |
| II-22 | 5.31 ± 0.06 |
| II-23 | 5.09 ± 0.04 |
| II-24 | 4.31 ± 0.05 |
| II-25 | 4.04 ± 0.07 |
| II-26 | 4.19 ± 0.03 |
| II-27 | 4.43 ± 0.04 |
| II-28 | 4.06 ± 0.06 |
| II-29 | 4.23 ± 0.03 |
| II-30 | 4.66 ± 0.02 |
| II-31 | 4.52 ± 0.04 |
| II-32 | 4.44 ± 0.05 |
| II-33 | 4.34 ± 0.04 |
| II-34 | 4.53 ± 0.05 |

6.3 Compound II-1 to II-87 have Relaxant Effect a on In-Vitro Vascular Smooth Muscle Against Contraction Induced by Hyperkalemia Solution in Rabbits After tension readings are stabilized, record a certain length of tension curve, and add AD ($10^{-5}$ mol/L) to induce contraction; if a maximum contract is achieved, wash the specimens thoroughly, and change K—H solution every 20 minutes, and then balance for 60 minutes; after baseline readings are stabilized, induce contract with AD of a same concentration again. When the maximum contract in the later induction is consistent with the former induction, add compound II-1 to II-34 solutions ($1\times10^{-10}$ to $1\times10^{-3}$ mol/L), II-35 to II-87 solutions ($1\times10^{-8}$-$1\times10^{-3}$ mol/L), and record the curves. Draw a dose-response curve using maximum relaxation response as 100%, relaxation percentage as ordinate and negative logarithms of the each concentration as abscissa. Wherein, compound II-36 and 37 have a significant relaxant effect as shown in FIGS. 3 and 4. wherein, compound II-65 have a relatively significant relaxant effect as shown in FIG. 13; wherein compound II-63 also shows significant relaxant effect, and the dose-response curve is shown in FIG. 14.

As shown in FIGS. 3 and 4, compound II-36 and 37 have relaxant effect against contraction induced by hyperkalemia solution, and the effect is dose-dependent to a certain level. And the $-\log EC_{50}$ of compound II-36 is 5.34±0.02 compared to 5.49±0.05 of compound II-37.

As shown in FIG. 13, compound II-65 has relaxant effect against hyperkalemia solution contraction induced by AD, and the effect is dose-dependent to a certain level. And the $-\log EC_{50}$ of compound II-65 is 5.55±0.03; similarly, as shown in FIG. 14, compound II-63 has a relaxant effect against contraction induced by hyperkalemia solution, and the effect is dose-dependent to a certain level. And the $-\log EC_{50}$ of compound II-65 is 5.64±0.01; also, as shown in FIG. 15, compound II-68 has a relaxant effect against contraction induced by hyperkalemia solution, and the effect is dose-dependent to a certain level. And the $-\log EC_{50}$ of compound II-65 is 4.77±0.06;

The relaxant effect of compound II-1 to II-87 are shown in Table 3.

TABLE 3

Relaxant Effect of the Compounds against Contraction of In-Vitro Vascular Smooth Muscle of Rabbits induced by hyperkalemia solution

| Compound | $-\log EC_{50}$ |
|---|---|
| II-1 | 4.69 ± 0.02 |
| II-2 | 4.82 ± 0.03 |
| II-3 | 6.01 ± 0.04 |
| II-4 | 6.12 ± 0.03 |
| II-5 | 4.44 ± 0.02 |
| II-6 | 4.38 ± 0.03 |
| II-7 | 5.03 ± 0.04 |
| II-8 | 4.56 ± 0.03 |
| II-9 | 4.23 ± 0.02 |
| II-10 | 5.22 ± 0.05 |
| II-11 | 5.17 ± 0.06 |
| II-12 | 5.09 ± 0.04 |
| II-13 | 5.12 ± 0.03 |
| II-14 | 5.72 ± 0.05 |
| II-15 | 5.12 ± 0.04 |
| II-16 | 5.28 ± 0.03 |
| II-17 | 5.02 ± 0.05 |
| II-18 | 5.32 ± 0.04 |
| II-19 | 5.11 ± 0.03 |
| II-20 | 3.92 ± 0.02 |
| II-21 | 3.96 ± 0.03 |
| II-22 | 3.53 ± 0.02 |
| II-23 | 4.23 ± 0.04 |
| II-24 | 3.53 ± 0.03 |
| II-25 | 4.26 ± 0.04 |
| II-26 | 3.31 ± 0.03 |
| II-27 | 3.63 ± 0.04 |
| II-28 | 3.46 ± 0.03 |
| II-29 | 4.53 ± 0.03 |
| II-30 | 4.26 ± 0.04 |
| II-31 | 4.32 ± 0.02 |
| II-32 | 4.14 ± 0.05 |
| II-33 | 4.04 ± 0.03 |
| II-34 | 4.13 ± 0.04 |
| II-35 | 5.05 ± 0.03 |
| II-36 | 5.34 ± 0.02 |
| II-37 | 5.49 ± 0.05 |
| II-38 | 4.79 ± 0.05 |
| II-39 | 4.53 ± 0.03 |
| II-40 | 4.41 ± 0.04 |
| II-41 | 3.79 ± 0.03 |
| II-42 | 4.41 ± 0.05 |
| II-43 | 4.28 ± 0.03 |
| II-44 | 3.96 ± 0.05 |
| II-45 | 3.85 ± 0.04 |
| II-46 | 4.15 ± 0.06 |
| II-47 | 4.52 ± 0.05 |
| II-48 | 4.05 ± 0.04 |
| II-49 | 4.52 ± 0.05 |
| II-50 | 4.19 ± 0.03 |
| II-51 | 4.31 ± 0.04 |
| II-52 | 4.74 ± 0.06 |

TABLE 3-continued

Relaxant Effect of the Compounds against Contraction of In-Vitro Vascular Smooth Muscle of Rabbits induced by hyperkalemia solution

| Compound | $-\log EC_{50}$ |
|---|---|
| II-53 | 4.06 ± 0.03 |
| II-54 | 3.93 ± 0.02 |
| II-55 | 3.75 ± 0.03 |
| II-56 | 4.64 ± 0.04 |
| II-57 | 4.42 ± 0.05 |
| II-58 | 4.52 ± 0.04 |
| II-59 | 4.53 ± 0.03 |
| II-60 | 3.99 ± 0.05 |
| II-61 | 4.06 ± 0.04 |
| II-62 | 3.85 ± 0.04 |
| II-63 | 5.64 ± 0.01 |
| II-64 | 5.13 ± 0.03 |
| II-65 | 5.55 ± 0.03 |
| II-66 | 4.61 ± 0.03 |
| II-67 | 3.94 ± 0.04 |
| II-68 | 4.77 ± 0.06 |
| II-69 | 4.49 ± 0.05 |
| II-70 | 5.31 ± 0.04 |
| II-71 | 5.43 ± 0.03 |
| II-72 | 5.33 ± 0.04 |
| II-73 | 5.22 ± 0.04 |
| II-74 | 4.61 ± 0.05 |
| II-75 | 3.93 ± 0.04 |
| II-76 | 3.85 ± 0.04 |
| II-77 | 3.73 ± 0.03 |
| II-78 | 3.92 ± 0.02 |
| II-79 | 3.54 ± 0.03 |
| II-80 | 3.43 ± 0.04 |
| II-81 | 3.85 ± 0.03 |
| II-82 | 4.46 ± 0.03 |
| II-83 | 4.91 ± 0.04 |
| II-84 | 4.31 ± 0.03 |
| II-85 | 4.11 ± 0.02 |
| II-86 | 4.58 ± 0.04 |
| II-87 | 3.88 ± 0.02 |

Example 89

Study on Relaxing Mechanism of Compound II-36, II-65 and II-68 on Contraction of In-Vitro Vascular Smooth Muscle of Rabbits Induced by Hyperkalemia Solution 1. Study Animal:

Rabbits of either sex, weighing 2.0-3.0 kg, provided by the Experimental Animal Center of China Medical University.

2. Drugs and Reagents

Compound II-36, 65 and 68 are prepared as per examples.

NaCl: Purchased from Tianjin Damao Chemical Reagent Factory, batch No.: 20120413.

KCl: Purchased from Tianjin Damao Chemical Reagent Factory, batch No.: 20111123.

MgSO$_4$: Purchased from Tianjin Damao Chemical Reagent Factory, batch No.: 20101029.

CaCl$_2$: Purchased from Tianjin Damao Chemical Reagent Factory, batch No.: 20110314.

NaHCO$_3$: Purchased from Tianjin Damao Chemical Reagent Factory, batch No.: 20120507.

Glucose: Purchased from Tianjin Damao Chemical Reagent Factory, batch No.: 20120512.

KH$_2$PO$_4$: Purchased from Tianjin Damao Chemical Reagent Factory, batch No.: 20110928.

NaCl injection: Purchased from Shenyang Zhiying Pharmaceutical Co. Ltd., batch number: 12021001.

Epinephrine Hydrochloride Injection: 1 mg/1 ml, purchased from GRANDPHARMA (CHINA) CO. LTD., batch number: 120105;

Norepinephrine Bitartrate Injection, 2 mg/1 ml, purchased from GRANDPHARMA (CHINA) CO. LTD., batch number: 120304;

Doxazosin Mesylate: Suizhou jiake pharmaceutical and chemical industry co. ltd., batch number: 20110305.

Amlodipine Besylate Tablets: Purchased from pfizer: 5 mg/table, batch number: 1205018.

Epinephrine Hydrochloride Injection: 1 mg/1 ml, purchased from GRANDPHARMA (CHINA) CO. LTD., batch number: 120105;

(R)-Phenylephrine Hydrochloride, TCI (Shanghai) Development Co., Ltd., batch number: GJ01-TESP.

Serotonin Creatinine Sulfate Monohydrate (5-HT), Tokyo Kasei Kogyo Co., Ltd. (TCI), batch number: AZ01-TBKD.

Heparin sodium: Wanbang Biopharmaceuticals: 2 ml/12500 Units, batch number: 101115.

Urethane: Shanghai Chemical Reagent Co. Ltd., SinoPharm, batch number: C30191228.

EDTA, Tianjin Damao Chemical Reagent Factory, batch No.: 20050809.

3. Instruments:

HSS-1(B) thermostatic bath: Chengdu Instrument Factory;

RM6240B Multi-channel physiological signal acquisition and processing system: Chengdu Instrument Factory;

JZJ01 muscle tension transducer: Chengdu Instrument Factory;

YPJ01 pressure transducer: Chengdu Instrument Factory;

TG-328A Photoelectric Analytical Balance: Shanghai Balance Instrument;

T-500 electronic balance: G&G Measurement Plant;

Micropipette: Shanghai Rong Tai Biochemical Engineering Co., Ltd.

Electric heated thermstatic water bath: Tianjin Taisite Instrument Co., LTD.

4. Preparation of Nutrient Solution

Krebs-Henseleit (K—H) physiological solution: NaCl 6.92 (concentration units), KCl 0.35, MgSO4 0.29, KH$_2$PO$_4$ 0.16, CaCl$_2$ 0.28, NaHCO$_3$ 2.1, glucose 2.0 (g/L), pH 7.2.

Potassium solution: Remove NaCl and add in an equivalent mole amount of KCl to formulate a modified K—H solution, containing K+60 mmol/L Calcium-free K—H solution: Remove CaCl$_2$ from K—H solution, add an equal number of moles of KCl, and add EDTA$^{-2}$Na$^+$ 0.1 mmol/L, while the other components remain unchanged.

Calcium-free hyperkalemia solution: Remove CaCl$_2$ from hyperkalemia solution, add an equal number of moles of KCl, and add EDTA$^{-2}$Na$^+$ 0.1 mmol/L, while the other components remain unchanged.

Preparation of compound II-36, 65 and 68 solutions: Weigh a certain quality compound samples and dilute to concentrations ($10^{-10}$ to 10-4 mol/L) with distilled water, standby.

5. Preparation of Rabbit Vascular Smooth Muscle Specimens

Cut the chest open quickly after stunning, strip out the descending aorta, then after removing the surrounding connective tissue and adipose tissue (if performed serotonin receptor antagonist experiments, endothelial cells should be removed using a smooth stainless steel bars), cut the vessels into 3-5 mm vascular ring, then pass the steel hook through the blood vessel ring, with one end is fixed to the vent hook and the other end connected to the tension transducer, then place the specimens into bath tube containing 20 mL of nutrient solution, and record tension change by tension transducer. Maintain tube temperature at 37±0.5° C., and pass bubbles (95% $O_2$+5% $CO_2$) into the solution as a speed of 1-2 bubbles/minute. Place an initial load of 1.5 g on the rings, and change nutrient every 20 minutes, then balance for 2 hours and start test after baseline readings are stabilized.

6. Test and Results 6.1 Antagonistic Action of Compound II-36, II-65 and II-68 on a Receptor Agonist of Vascular Smooth Muscle 6.1.1 Effect of Compound II-36 on Dose-Response Curve of Norepinephrine Cumulative Contraction After the tension is stabilized, record a certain length of the curve, and add NA ($10^{-8}$-$10^{-4}$ mol/L) to the tube until a maximum response is achieved, and then record the curve. Then wash the specimen with K—H solution repeatedly, balance for 1 h, add compound II-36 ($3\times10^{-7}$ mol/L), and 20 minutes later, add NA following a same procedure. Mark NA contraction as ordinate using maximum response as 100% base. The negative logarithm of NA concentrations are used as abscissa to create dose-response curve; after compound II-36 ($3\times10^{-7}$ mol/L) is added, NA dose-response curve is significantly moved to the right, while maximum response is barely changed; t test on dose-response of different concentrations showed that most of the P values are less than 0.01, showing significant difference. The antagonism parameter ($pA_2$ values, a parameter showing the strength of antagonism, is a negative logarithm of the antagonist molar concentration required to keep the response at a same level when concentration of agonist is doubled) of compound II-36 is 7.37±0.08 on NA contraction on rabbit aorta. The larger the $PA_2$ value, the stronger the antagonist effect. It is calculated based on the values of the attached figures by software.

6.1.2 Curves of Effect Against Accumulation Contraction of Norepinephrine Contraction by Positive Control Drug Doxazosin After the tension is stabilized, record a certain length of the curve, and add NA ($10^{-8}$-$10^{-4}$ mol/L) to the tube until a maximum response is achieved, and then record the curve. Then wash the specimens repeatedly with K—H solution, and refresh K—H solution every 20 minutes, and balance for 60 minutes to allow baseline values are stabilized; then add doxazosin ($10^{-7}$ mol/L) and after 15 minutes, add NA in the same way ($10^{-8}$-$6\times10^{-5}$ mol/L). Mark NA contraction as ordinate using maximum response as 100% base. The negative logarithm of NA concentrations are used as abscissa to create dose-response curve; after doxazosin ($10^{-7}$ mol/L) is added, NA dose-response curve is significantly moved to the right, while maximum response is barely changed; t test on dose-response of different concentrations showed that most of the P values are less than 0.01, showing significant difference. The $PA_2$ value of positive control doxazosin is 7.52±0.04 against NA contraction of rabbit aorta.

Compared to positive control doxazosin, the $PA_2$ value of compound II-36 against NA showed no significant difference (P>0.05), indicating the similarity on antagonist effect between compound II-36 and doxazosin against a receptor agonist.

6.1.3 Effect of Compound II-65 on Dose-Response Curve of Norepinephrine Cumulative Contraction After the tension is stabilized, record a certain length of the curve, and add NA ($3\times10^{-7}$-$6\times10^{-5}$ mol/L) to the tube until a maximum response is achieved, and then record the curve. Then wash the specimen with K—H solution repeatedly, balance for 1 h, add compound II-65 ($3\times10^{-6}$ mol/L), and 20 minutes later, add NA ($3\times10^{-7}$-$3\times10^{-4}$ mol/L) following a same procedure. Mark NA contraction as ordinate using maximum response as 100% base. The negative logarithm of NA concentrations are used as abscissa to create dose-response curve; after compound II-65 ($3\times10^{-6}$ mol/L) is added, NA dose-response curve is significantly moved to the right, while maximum response is barely changed; t test on dose-response of different concentrations showed that most of the P values are less than 0.01, showing significant difference. $PA_2$ value of compound II-65 is 6.02±0.13 against NA contraction effect on rabbit aorta.

6.1.4 Curves of Effect Against Accumulation Contraction of Norepinephrine Contraction by Positive Control Drug Doxazosin After above procedures, wash the specimen repeatedly with K—H solution, balance for 1 hour, add doxazosin ($10^{-7}$ mol/L), and add NA in the same way after 15 minutes. Mark NA contraction as ordinate using maximum response as 100% base. The negative logarithm of NA concentrations ($3\times10^{-7}$-$3\times10^{-4}$ mol/L) are used as abscissa to create dose-response curve; after doxazosin ($10^{-7}$ mol/L) is added, NA dose-response curve is significantly moved to the right, while maximum response is barely changed; t test on dose-response of different concentrations showed that most of the P values are less than 0.01, showing significant difference. The $PA_2$ value of positive control doxazosin is 7.16±0.24 against NA contraction of rabbit aorta.

Compared to positive control doxazosin, t test indicates that the $PA_2$ value of compound II-65 against NA showed no significant difference (P<0.01), indicating significant difference on antagonist effect between compound II-65 (weaker) and doxazosin against a receptor agonist.

6.1.5 Curves of Accumulative Effect Against Norepinephrine Contraction by Compound II-68

After the tension is stabilized, record a certain length of the curve, and add Phenylephrine ($10^{-6}$-$6\times10^{-3}$ mol/L) to the tube until a maximum response is achieved, and then record the curve. Then wash the specimen with K—H solution repeatedly, balance for 1 h, add compound II-68 ($3\times10^{-8}$ mol/L), and 20 minutes later, add Phenylephrine following a same procedure. Mark Phenylephrine contraction as ordinate using maximum response as 100% base. The negative logarithm of Phenylephrine concentrations are used as abscissa to create dose-response curve; after compound II-68 ($3\times10^{-8}$ mol/L) is added, NA dose-response curve is significantly moved to the right, while maximum response is barely changed; t test on dose-response of different concentrations showed that most of the P values are less than 0.01, showing significant difference. $PA_2$ value of compound II-68 is 8.45±0.03 against Phenylephrine contraction effect on rabbit aorta.

6.2 Antagonistic Action of Compound II-36, II-65 and II-68 on a Receptor Agonist of $Ca^{2+}$ Channel of Vascular Smooth Muscle 6.2.1 Curves of Accumulative Effect Against $CaCl_2$ Contraction by Compound II-36

After the tension is stabilized, wash the specimen three times and incubate with Ca-free K—H solution for 40 minutes; depolarize with Ca-free hyperkalemia solution for 20 minutes, and then add $CaCl_2$ ($10^{-6}$-$10^{-2}$ mol/L) to the tube until a maximum response is achieved, and then record the curve. Then wash with K—H solution repeatedly, and replace with fresh K—H solution every 20 minutes; after balancing for 60 minutes and the baseline values are stabilized, wash the specimen again three times, and incubate with Ca-free K—H solution for 40 minutes; depolarize with Ca-free hyperkalemia solution for 20 minutes, and then add compound II-36 ($3\times10^{-6}$ mol/L) to the tube, and incubate for 20 minutes; then add $CaCl_2$ ($10^{-6}$-$10^{-2}$ mol/L) until a maximum response is achieved, and then record the curve. Mark CaCl$_2$ contraction as ordinate using maximum response as 100% base. The negative logarithm of CaCl$_2$ concentrations are used as abscissa to create dose-response curve; after compound II-36 (3×10$^{-6}$ mol/L) is added, CaCl$_2$ dose-response curve is significantly moved to the right as shown in FIG. 7, while maximum response is barely changed; t test on dose-response of different concentrations showed that most of the P values are less than 0.01, showing significant difference. PA$_2$ value of compound II-36 is 5.61±0.04 against CaCl$_2$ contraction effect on rabbit aorta.

6.2.2 Curves of Effect Against Accumulation Contraction of CaCl$_2$ Contraction by Positive Control Drug Amlodipine After the tension is stabilized, wash the specimen three times and incubate with Ca-free K—H solution for 40 minutes; depolarize with Ca-free hyperkalemia solution for 20 minutes, and then add CaCl2 (10$^{-6}$-10$^{-2}$ mol/L) to the tube until a maximum response is achieved, and then record the curve. Then wash with K—H solution repeatedly, and replace with fresh K—H solution every 20 minutes; after balancing for 60 minutes and the baseline values are stabilized, wash the specimen again three times, and incubate with Ca-free K—H solution for 40 minutes; depolarize with Ca-free hyperkalemia solution for 20 minutes, and then add amlodipine (10$^{-7}$ mol/L) to the tube, and incubate for 15 minutes; then add CaCl$_2$ (10$^{-6}$-10$^{-2}$ mol/L) until a maximum response is achieved, and then record the curve. Mark CaCl$_2$ contraction as ordinate using maximum response as 100% base. The negative logarithm of CaCl$_2$ concentrations are used as abscissa to create dose-response curve; after amlodipine (10$^{-7}$ mol/L) is added, CaCl$_2$ dose-response curve is significantly moved to the right as shown in FIG. 8, while maximum response is barely changed; t test on dose-response of different concentrations showed that most of the P values are less than 0.01, showing significant difference. PA$_2$ value of amlodipine is 6.99±0.05 against CaCl$_2$ contraction effect on rabbit aorta.

6.2.3 Curves of Accumulative Effect Against CaCl$_2$ Contraction by Compound II-65 and 68

After the tension is stabilized, wash the specimen three times and incubate with Ca-free K—H solution for 40 minutes; depolarize with Ca-free hyperkalemia solution for 20 minutes, and then add CaCl$_2$ (10$^{-5}$-3×10$^{-2}$ mol/L) to the tube until a maximum response is achieved, and then record the curve. Then wash with K—H solution repeatedly, and replace with fresh K—H solution every 20 minutes; after balancing for 60 minutes and the baseline values are stabilized, wash the specimen again three times, and incubate with Ca-free K—H solution for 40 minutes; depolarize with Ca-free hyperkalemia solution for 20 minutes, and then add compound II-65 or II-68 (10$^{-5}$ mol/L) to the tube, and incubate for 20 minutes; then add CaCl$_2$ (10$^{-5}$-3×10$^{-1}$ mol/L) until a maximum response is achieved, and then record the curve. Mark CaCl$_2$ contraction as ordinate using maximum response as 100% base. The negative logarithm of CaCl$_2$ concentrations are used as abscissa to create dose-response curve; after compound II-65 or II-68 (10$^{-5}$ mol/L) is added, CaCl$_2$ dose-response curve is significantly moved to the right, while maximum response is barely changed; t test on dose-response of different concentrations showed that most of the P values are less than 0.01, showing significant difference. PA$_2$ value of compound II-65 is 6.56±0.032 against CaCl$_2$ contraction effect on rabbit aorta; PA$_2$ value of compound II-68 is 5.36±0.26 against CaCl$_2$ contraction effect on rabbit aorta.

6.2.4 Curves of Effect Against Accumulation Contraction of CaCl$_2$ Contraction by Positive Control Drug Amlodipine Based on above procedures, wash the specimen with K—H solution repeatedly, and replace with fresh K—H solution every 20 minutes; after balancing for 60 minutes and the baseline values are stabilized, wash the specimen again three times, and incubate with Ca-free K—H solution for 40 minutes; depolarize with Ca-free hyperkalemia solution for 20 minutes, and then add amlodipine (10$^{-7}$ mol/L) to the tube, and incubate for 15 minutes; then add CaCl$_2$ (10$^{-5}$-3×10$^{-2}$ mol/L) until a maximum response is achieved, and then record the curve. Mark CaCl$_2$ contraction as ordinate using maximum response as 100% base. The negative logarithm of CaCl$_2$ concentrations are used as abscissa to create dose-response curve; after amlodipine (10$^{-7}$ mol/L) is added, CaCl$_2$ dose-response curve is significantly moved to the right as shown in FIG. 17, while maximum response is barely changed; t test on dose-response of different concentrations showed that most of the P values are less than 0.01, showing significant difference. PA$_2$ value of amlodipine is 7.15±0.288 against CaCl$_2$ contraction effect on rabbit aorta.

6.3 Antagonistic Action of Compound II-36, II-65 and II-68 on 5-HT Receptor Agonist of Vascular Smooth Muscle After the tension is stabilized, record a certain length of the curve, and add 5-HT (10$^{-7}$-3×10$^{-4}$ mol/L) to the tube until a maximum response is achieved, and then record the curve. Then wash the specimen with K—H solution repeatedly, balance for 1.5 h, add compound II-36 (3×10$^{-6}$ mol/L), and 20 minutes later, add 5-HT following a same procedure. Mark 5-HT contraction as ordinate using maximum response as 100% base. The negative logarithm of 5-HT concentrations are used as abscissa to create dose-response curve; after compound II-36 (3×10$^{-6}$ mol/L) is added, 5-HT dose-response curve is significantly moved to the right as shown in FIG. 9, while maximum response is barely changed; t test on dose-response of different concentrations showed that most of the P values are less than 0.01, showing significant difference. PA$_2$ value of compound II-36 is 5.71±0.08 against 5-HT contraction effect on rabbit aorta.

After the tension is stabilized, record a certain length of the curve, and add 5-HT (10$^{-8}$-3×10$^{-4}$ mol/L) to the tube until a maximum response is achieved, and then record the curve. Then wash the specimen with K—H solution repeatedly, balance for 1.5 h, add compound II-65 (3×10$^{-6}$ mol/L), and 20 minutes later, add 5-HT following a same procedure. Mark 5-HT contraction as ordinate using maximum response as 100% base. The negative logarithm of 5-HT concentrations are used as abscissa to create dose-response curve; after compound II-65 (3×10$^{-6}$ mol/L) is added, 5-HT dose-response curve is significantly moved to the right as shown in FIG. 18, while maximum response is barely changed; t test on dose-response of different concentrations showed that most of the P values are less than 0.01, showing significant difference. PA$_2$ value of compound II-65 is 6.726±0.089 against 5-HT contraction effect on rabbit aorta.

After the tension is stabilized, record a certain length of the curve, and add 5-HT (10$^{-8}$-3×10$^{-4}$ mol/L) to the tube until a maximum response is achieved, and then record the curve. Then wash the specimen with K—H solution repeatedly, balance for 1.5 h, add compound II-68 (10$^{-7}$ mol/L), and 20 minutes later, add 5-HT following a same procedure. Mark 5-HT contraction as ordinate using maximum response as 100% base. The negative logarithm of 5-HT concentrations are used as abscissa to create dose-response curve; after compound II-68 (10$^{-7}$ mol/L) is added, 5-HT dose-response curve is significantly moved to the right as shown in FIG. 21, while maximum response is barely changed; t test on dose-response of different concentrations showed that most of the P values are less than 0.01, showing significant difference. $PA_2$ value of compound II-68 is 8.86±0.14 against 5-HT contraction effect on rabbit aorta.

Studies on smooth muscle relaxant effect of compound II-36 showed that, it showed competitive antagonistic effect against Phenylephrine, $Ca^{2+}$ and 5-HT, and move the dose-response curve of these agonist to the right, but does not reduce maximum response, indicating competitive antagonist effect; the $PA_2$ values of compound II-36 against Phenylephrine, $Ca^{2+}$ and 5-HT are 7.37±0.08 (Doxazosin, 7.52±0.04), 5.61±0.04 (amlodipine 6.99±0.05) and 5.71±0.08, respectively (As shown in FIGS. 3, 4, 5, 6 and 7). The results showed that compound II-36 relax blood vessels by blocking $\alpha_1$ receptors, $Ca^{2+}$ channel and vascular $5-HT_{2A}$ receptor.

Summary: In-vitro animal studies showed that all of compound II-63, II-65 and II-68 showed significant blood vessel relaxing effect. Wherein, compound II-65 showed a relative strong effect on $\alpha_1$ receptors, have $PA_2$ value of 6.02±0.13 against NA, 7.16±0.24 against doxazosin, and 6.56±0.032 against $CaCl_2$; $PA_2$ value of amlodipine is 7.15±0.288 against $CaCl_2$; compound II-65 showed a relative strong effect against $5-HT_{2A}$ receptors with a $PA_2$ value of 6.726±0.089; compound II-68 showed a $PA_2$ value of 8.45±0.03 against Phenylephrine, with a $PA_2$ value of 5.36±0.26 against $CaCl_2$ and 8.86±0.14 against 5-HT. Study results showed that both compound II-65 and II-68 are vasodilating active molecules with multi novel targets; they can be used to prepare vasodilating drugs, especially new antihypertensive drugs.

Example 90

Acute Toxicity Test on Compounds II-36
Use Kunming mice (provided by the China Medical University Experimental Animal Center), half male and half female, weighing 18-22 g, and conduct acute toxicity test on compound (II-2) using simplified probability unit method; $LD_{50}$ of oral administration was 361.88 mg/kg (95% confidence interval: 302.96-420.80 mg/kg).

Example 91

Bone Marrow Micronucleus Test on Mice with Compound II-36
Use 10 Kunming mice (provided by the China Medical University Experimental Animal Center), half male and half female, and provide oral administration with compound II-36 at a dose of 120 mg/kg/day based on weight. After four days of continuous administration, perform bone marrow micronucleus test on the 5th day.

Positive contro, Cyclophosphamide 60 mg/kg/day; negative control, saline solution 0.1 ml/10 g/day. After four days of continuous administration, perform bone marrow micronucleus test on the 5th day.

The mice were sacrificed by cervical dislocation, and quickly stripped out of the femur and sternum;

blood and muscles were removed, epiphysis was cleaned; then sternum bone marrow was transfer with a hemostat squeeze onto clean slides with drops of calf serum or wash the femoral the marrow with fetal calf serum directly onto clean slides; after mixing, adjust slides well; then put the adjusted and aired slide into a staining jar filled with methanol, and allow to fix for 15 minutes; and then take it out and place in air until dry out; then, use freshly prepared Giemsa application solution (one sample of Giemsa stock solution and nine samples of phosphate buffer pH 6.8), stained for 10 minutes to wash away slide dye with small stream of water, and then observe under a microscope after it is dried.

Study results showed: In compound II-36 group, 2.0±0.333‰ of the 1000 polychromatic erythrocytes were found with micronucleus, while the percentage are 1‰ and 12‰ in blank control group and cyclophosphamide group, respectively. It showed that result is negative in bone marrow micronucleus test with compound II-36.

Example 92

Effect of Compound II-36 on Blood Pressure of SD Rats
Four SD rats were anesthetized with urethane (1.25 mg/kg); after vital signs were stable, measure blood pressure through carotid artery cannulation. After blood pressure is stabilized, compound II-36 was administered orally (4.0 mg/kg, body weight), and blood pressure changes with time were recorded; study results are shown in Table 4, 5 and 6.

TABLE 4

Effect of compound II-36 on diastolic blood pressure (DBP, mmHg) of Urethane-anesthetized rats (n = 4)

| Group | Dose (mg/kg) | Time after administration | | | | | | | | |
|---|---|---|---|---|---|---|---|---|---|---|
| | | 0 | 15 | 30 | 60 | 90 | 120 | 150 | 180 | 210 |
| Compound II-36 | 4.0 | 75.92 ± 26.19 | 62.21 ± 19.99** | 61.84 ± 24.65** | 58.04 ± 18.49** | 53.86 ± 20.22** | 69.10 ± 27.71** | 70.79 ± 27.81* | 71.08 ± 29.22* | 75.26 ± 33.42 |

Note:
*P < 0.05,
**P < 0.01

TABLE 5

Effect of compound II-36 on Systolic blood pressure (SBP, mmHg) of Urethane-anesthetized rats (n = 4)

| Group | Dose (mg/kg) | Time after administration | | | | | | | | |
|---|---|---|---|---|---|---|---|---|---|---|
| | | 0 | 15 | 30 | 60 | 90 | 120 | 150 | 180 | 210 |
| Compound II-36 | 4.0 | 122.66 ± 20.73 | 95.77 ± 16.29** | 99.88 ± 22.77** | 102.22 ± 16.29** | 98.71± 13.68** | 111.16 ± 20.37** | 111.82 ± 15.75** | 112.34 ± 15.26** | 115.12 ± 18.81* |

Note:
*P < 0.05,
**P < 0.01

TABLE 6

Effect of compound II-36 on mean arterial pressure (MAP, mmHg) of Urethane-anesthetized rats (n = 4)

| Group | Dose (mg/kg) | Time after administration | | | | | | | | |
|---|---|---|---|---|---|---|---|---|---|---|
| | | 0 | 15 | 30 | 60 | 90 | 120 | 150 | 180 | 210 |
| Compound II-36 | 4.0 | 91.50 ± 24.15 | 73.40 ± 17.80** | 74.52 ± 23.67** | 72.77 ± 17.52** | 68.81 ± 17.92** | 83.12 ± 25.17** | 84.47 ± 23.17** | 84.83 ± 24.50** | 88.54 ± 28.23* |

Note:
*P < 0.05,
**P < 0.01

Study results showed: Compound II-36 showed significant hypotensive effect on Urethane-anesthetized rats (1.25 mg/kg), which recovered to the level before administration after 3.5 hours.

Summary: In-vitro animal studies showed that all of compound II-36 showed significant vascular smooth muscle relaxant effect. Compound II-36 showed a comparative antagonistic effect on adrenaline a receptor; the $PA_2$ value of its antagonistic effect against noradrenaline is 7.37±0.08, the $PA_2$ value of doxazosin against NA is 7.52±0.04, the $PA_2$ value of compound II-36 is 5.61±0.04 against $CaCl_2$ and 5.71±0.08 against 5-HT. In-vivo test with rats showed, the compound II-36 has a significant antihypertensive effect, well oral absorption, low toxicity, high therapeutic index, negative results in bone marrow micronucleus test, and can be sued as a new multi-target vasodilating drug, with potential value a new antihypertensive drug, especially.

The invention claimed is:

1. A compound of the following formula (I) or pharmaceutically acceptable salt thereof:

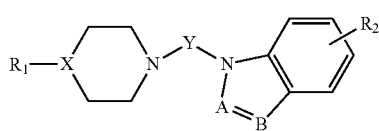
(I)

wherein:
$R_1$ represents an aromatic group which is mono- or polysubstituted with $R_3$, wherein the aromatic group is phenyl or benzisothiazolyl;
$R_3$ is H, Cl, $CF_3$, or $CH_3$; when $R_3$ are groups for polysubstitution, each $R_3$ is independently selected from the group consisting of the above-mentioned groups;
A, B and X each represents N;
$R_2$ is H; and
Y represents butylene group.

2. The compound of claim 1, wherein the pharmaceutically acceptable salt is hydrochloride salt, hydrobromide salt, sulfate salt, trifluoroacetate salt, methanesulfonate salt, tartrate salt, malate salt, succinate salt, maleate salt, citrate salt, phosphate salt, lactate salt, pyruvate salt, acetate salt, fumarate salt, oxaloacetate salt, ethanesulfonate salt, oxalate salt, besylate salt or isethionate salt.

3. The compound of claim 1, wherein the aromatic group is phenyl.

4. The compound of claim 1, wherein $R_3$ is $CF_3$.

5. The compound of claim 1, selected from:
I-63  1-(4-(4-(3-chlorophenyl)piperazin-1-yl)butyl)-1H-benzotriazole,
I-65  1-(4-(4-(3-trifluoromethylphenyl)piperazin-1-yl)butyl)-1H-benzotriazole,
I-68  3-(4-(4-(1H-benzotriazol-1-yl)butyl)piperazin-1-yl)benzisothiazole, and
I-81  1-(4-(4-(3-(6-fluorobenzisothiazolyl)))piperazin-1-yl)butyl)-1H-benzotriazole.

6. A method for preparing the compound of claim 1, comprising:
scheme (I)
wherein a compound

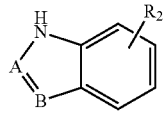 and a compound 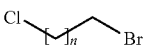

are reacted in a solvent in the presence of an inorganic base and a phase transfer catalyst, in a first reaction step, to yield a compound

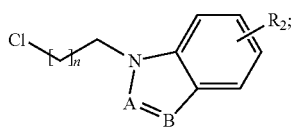

and then under reflux, the resulting compound is reacted with

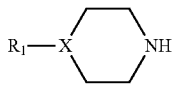

in a solvent in the presence of an organic base, in a second reaction step, to yield a compound

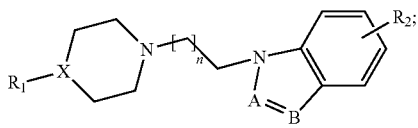

wherein A, B, X, $R^1$, and $R^2$ are as defined in claim 1, and wherein n is 3.

7. A pharmaceutical composition comprising the compound or pharmaceutically acceptable salt thereof according to claim 1, optionally together with one or more pharmaceutically acceptable excipients or other active substances having effect of relaxing vascular smooth muscle spasm.

8. The compound of claim 5, selected from:
I-63  1-(4-(4-(3-chlorophenyl)piperazin-1-yl)butyl)-1H-benzotriazole,
I-65  1-(4-(4-(3-trifluoromethylphenyl)piperazin-1-yl)butyl)-1H-benzotriazole, and
I-68  3-(4-(4-(1H-benzotriazol-1-yl)butyl)piperazin-1-yl) benzisothiazole.

9. The method of claim 6, wherein in scheme (I), in the first reaction step:
the inorganic base is sodium hydride, sodium hydroxide, sodium methoxide, sodium ethoxide, sodium carbonate, sodium hydrogencarbonate, potassium hydride, potassium hydroxide, potassium methoxide, potassium ethoxide, potassium carbonate or potassium bicarbonate;
the phase transfer catalyst is tetrabutylammonium bromide, tetrabutylammonium chloride, tetrabutyl ammonium hydrogen sulfate or 1,4,7,10,13,16-hexaoxacyclooctadecane;
the solvent is water except when sodium hydride is used, N-methylpyrrolidone (NMP), N,N-dimethylformamide (DMF), or a mixture of two or more thereof;
reaction temperature is 10-150° C.; and
reaction time is 0.5-20 hours.

10. The method of claim 6, wherein in scheme (I), in the second reaction step:
potassium iodide is present;
the organic base is diisopropylethylamine, diethylamine, triethylamine, pyridine, t-butylamine, cyclopropylamine, di-n-butylamine, diisopropylamine, or 1,2-dimethylpropylamine;
the solvent is acetonitrile, DMF, dimethylsulfoxide (DMSO) or methyl ethyl ketone, or a mixture of two or more thereof; and
reaction time is 1-30 hours.

* * * * *

UNITED STATES PATENT AND TRADEMARK OFFICE
CERTIFICATE OF CORRECTION

PATENT NO.         : 9,802,929 B2
APPLICATION NO.    : 14/647378
DATED              : October 31, 2017
INVENTOR(S)        : Yan Zhou It is certified that error appears in the above-identified patent and that said Letters Patent is hereby corrected as shown below:

In the Specification

Column 29, Line 2: "impartial block on a1 receptors" should be --impartial block on α1 receptors--.

Column 29, Line 9: "the remaining a1 receptors still" should be --the remaining α1 receptors still--.

Column 76, Line 60: "Compound II-1 to ii-34 have" should be --Compound II-1 to II-34 have--.

Column 81, Line 8: "on a Receptor Agonist" should be --on α Receptor Agonist--.

Column 82, Line 29: "against a receptor agonist" should be --against α receptor agonist--.

Column 82, Line 50: "on a Receptor Agonist" should be --on α Receptor Agonist--.

Column 88, Line 35: "adrenaline a receptor" should be --adrenaline α receptor--.

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*

UNITED STATES PATENT AND TRADEMARK OFFICE
CERTIFICATE OF CORRECTION

PATENT NO. : 9,802,929 B2
APPLICATION NO. : 14/647378
DATED : October 31, 2017
INVENTOR(S) : Yan Zhou et al.

It is certified that error appears in the above-identified patent and that said Letters Patent is hereby corrected as shown below:

On the Title Page

Item (72), is corrected to add PENG WANG, Shenzhen (CN)

Signed and Sealed this
Thirteenth Day of August, 2019

Andrei Iancu
*Director of the United States Patent and Trademark Office*